US012702381B2

(12) United States Patent
Jin et al.

(10) Patent No.: US 12,702,381 B2
(45) Date of Patent: Aug. 11, 2026

(54) ULTRASOUND IMAGING DEVICE INCLUDING TOUCH SCREEN AND CONTROL METHOD THEREOF

(71) Applicant: Samsung Medison Co., Ltd., Hongcheon-gun (KR)

(72) Inventors: Gilju Jin, Seoul (KR); Deokbeom Suh, Seoul (KR); Mijeoung Ahn, Seoul (KR)

(73) Assignee: SAMSUNG MEDISON CO., LTD., Hongcheon-Gun (KR)

( * ) Notice: Subject to any disclaimer, the term of this patent is extended or adjusted under 35 U.S.C. 154(b) by 23 days.

(21) Appl. No.: 18/596,090

(22) Filed: Mar. 5, 2024

(65) Prior Publication Data

US 2024/0335181 A1 Oct. 10, 2024

(30) Foreign Application Priority Data

Apr. 10, 2023 (KR) ........................ 10-2023-0047116
May 31, 2023 (KR) ........................ 10-2023-0070488
Dec. 1, 2023 (KR) ........................ 10-2023-0172768

(51) Int. Cl.
*A61B 8/00* (2006.01)
*A61B 8/08* (2006.01)

(52) U.S. Cl.
CPC ............ *A61B 8/463* (2013.01); *A61B 8/4427* (2013.01); *A61B 8/469* (2013.01); *A61B 8/488* (2013.01); *A61B 8/5207* (2013.01)

(58) Field of Classification Search
CPC ....... A61B 8/463; A61B 8/4427; A61B 8/469; A61B 8/488; A61B 8/5207; A61B 8/465; G06F 3/04845
See application file for complete search history.

(56) References Cited

U.S. PATENT DOCUMENTS 8,836,703 B2 9/2014 Venon et al.
10,416,867 B2 9/2019 Ohashi et al.
(Continued)

FOREIGN PATENT DOCUMENTS

CN 111870326 A * 11/2020 ......... A61B 17/3403
JP 2018-142331 A 9/2018
(Continued)

OTHER PUBLICATIONS

CN-111870326 machine translation (Year: 2020).*
(Continued)

*Primary Examiner* — Alexei Bykhovski
(74) *Attorney, Agent, or Firm* — Morgan Lewis & Bockius LLP

(57) ABSTRACT

A control method of an ultrasound imaging device includes displaying an ultrasound image in a display area of a touch screen, displaying a first indicator to overlap on the ultrasound image, obtaining a first touch input of moving the ultrasound image in the display area while a position of the first indicator is fixed in the display area, determining a position of the first indicator to be a first position, in response to a first position determination input of determining the position of the first indicator so as to place the first indicator at the first position on the ultrasound image, and moving the ultrasound image, in response to a second touch input of moving the ultrasound image in the display area while the position of the first indicator is determined to be the first position.

20 Claims, 28 Drawing Sheets

(56) References Cited

U.S. PATENT DOCUMENTS

| | | | | |
|---|---|---|---|---|
| 10,420,533 | B2 | 9/2019 | Kim et al. | |
| 2003/0199766 | A1* | 10/2003 | Kato | A61B 8/462 600/443 |
| 2010/0171764 | A1 | 7/2010 | Feng et al. | |
| 2013/0088519 | A1 | 4/2013 | Cristescu et al. | |
| 2017/0090675 | A1 | 3/2017 | Lee et al. | |
| 2017/0209125 | A1 | 7/2017 | Rai | |
| 2023/0320699 | A1* | 10/2023 | Lee | G16H 50/30 715/768 |

FOREIGN PATENT DOCUMENTS

| | | | | |
|---|---|---|---|---|
| KR | 20110062727 | A * | 6/2011 | G01N 29/00 |
| KR | 10-2293915 | B1 | 8/2021 | |

OTHER PUBLICATIONS

The KR-20110062727-A machine translation (Year: 2011).*
The Extended European Search Report dated Jul. 31, 2024 issued in European Patent Application No. 24157410.2.
Notice of Allowance dated Nov. 6, 2025 issued in the corresponding European Patent Application No. 24157410.2. (Note: US 2003-0199766 A1 previously cited.).

* cited by examiner

Figure 1A:
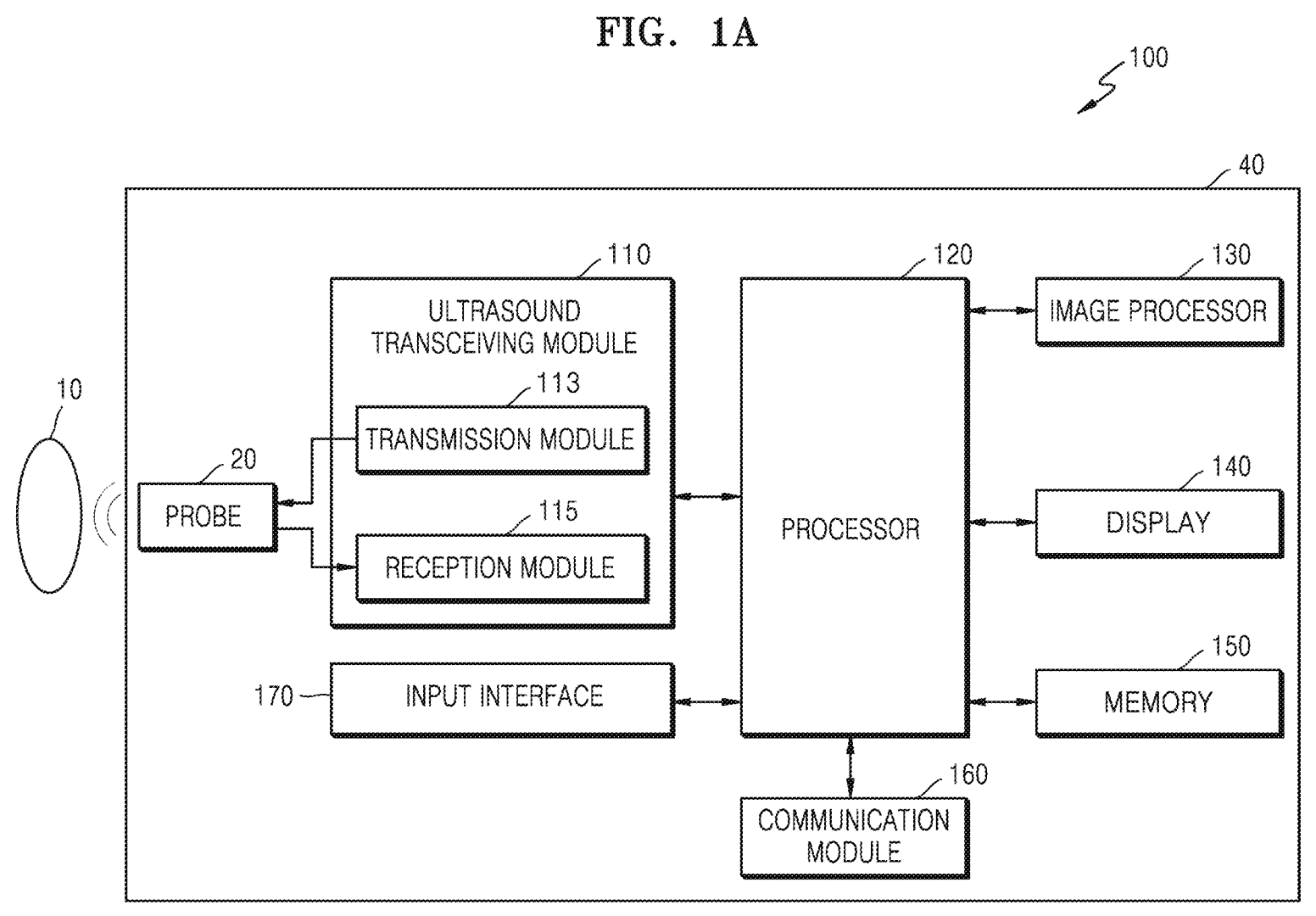

130 IMAGE PROCESSOR

140 DISPLAY

150 MEMORY

120 PROCESSOR

160 COMMUNICATION MODULE

110 ULTRASOUND TRANSCEIVING MODULE

113 TRANSMISSION MODULE

115 RECEPTION MODULE

170 INPUT INTERFACE

20 PROBE

10

Figure 1B:
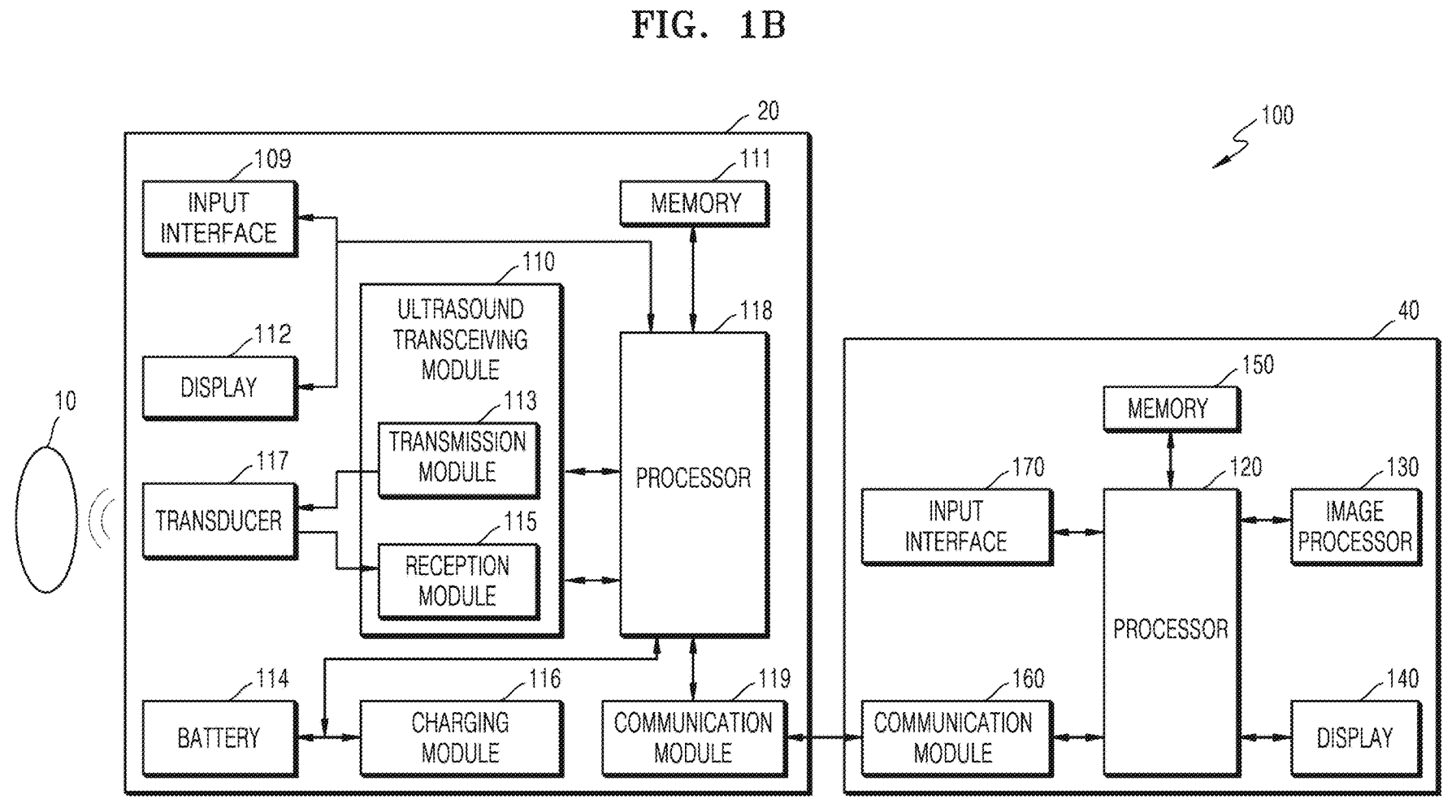

FIG. 1B 100
20
111 MEMORY
118 PROCESSOR
119 COMMUNICATION MODULE
110 ULTRASOUND TRANSCEIVING MODULE
113 TRANSMISSION MODULE
115 RECEPTION MODULE
116 CHARGING MODULE
109 INPUT INTERFACE
112 DISPLAY
117 TRANSDUCER
114 BATTERY
10
40
150 MEMORY
120 PROCESSOR
130 IMAGE PROCESSOR
140 DISPLAY
170 INPUT INTERFACE
160 COMMUNICATION MODULE 40
141
ABC GEN/CA1-7S/14.0cm/31Hz
TIs 0.1/TIb 0.1/MI 1.4
[2D]
Gen
Gn 53
DR 96
FA 4
P 90%
420
410
406
451
ZOOMING-IN OF ULTRASOUND IMAGE
510
530
501
CONFIRM

MOVEMENT OF ULTRASOUND IMAGE
DETERMINATION OF INDICATOR POSITION
CONFIRM
CONFIRM
141
40
510
451
505
501
651
ABC GEN/CA1-7S/14.0cm/31Hz
Tis 0.1/Tib 0.1/MI 1.4
[2D]
Gen
Gn 53
DR 96
FA 4
P 90%

MOVEMENT OF ULTRASOUND IMAGE
DETERMINATION OF INDICATOR POSITION
CONFIRM
CONFIRM
40
141
510
651a
661a
452
505
501
651b
652
ABC GEN/CA1-7S/14.0cm/31Hz
Tis 0.1/Tib 0.1/MI 1.4
[2D]
Gen
Gn 53
DR 96
FA 4
P 90%

SELECTION OF FIRST INDICATOR
ZOOMING-IN OF ULTRASOUND IMAGE
CONFIRM
40
141
420
1001
1002
1011
1012
1020
1050
1051
501
[2D]
Gen
Gn 53
DR 96
FA 4
P 90%

MOVEMENT OF ULTRASOUND IMAGE
40
141
1002
420
1020
1011
505
501
CONFIRM
ABC GEN/CA1-7S/14.0cm/31Hz
Tis 0.1/Tib 0.1/MI 1.4
[2D]
Gen
Gn 53
DR 96
FA 4
P 90%
1021a
1021b
1022a
1022b
1030a
1030b

SELECTION OF DOPPLER IMAGE MODE
MOVEMENT OF ULTRASOUND IMAGE
141
40
ABC GEN/CA1-7S/14.0cm/31Hz TIs 0.1/TIb 0.1/MI 1.4
[2D]
Gen
Gn 53
DR 96
FA 4
P 90%
1201
1202
1211
1212
1213
405

1400
1410
1420
1430
1451

ULTRASOUND IMAGING DEVICE INCLUDING TOUCH SCREEN AND CONTROL METHOD THEREOF

CROSS-REFERENCE TO RELATED APPLICATION

This application is based on and claims priority under 35 U.S.C. § 119 to Korean Patent Application Nos. 10-2023-0047116, filed on Apr. 10, 2023, 10-2023-0070488, filed on May 31, 2023, and 10-2023-0172768, filed on Dec. 1, 2023 in the Korean Intellectual Property Office, the disclosures of which are incorporated by reference herein in their entirety.

BACKGROUND

1. Field

The disclosure relates to an ultrasound imaging device including a touch screen and a control method of the ultrasound imaging device. In particular, the disclosure relates to an ultrasound imaging device configured to determine a position of an indicator in an ultrasound image, and a control method of the ultrasound imaging device.

2. Description of the Related Art

Recently, various medical imaging devices for imaging and obtaining information about tissues and organs of the human body have been widely used for the purposes of early diagnosis and treatment of diseases. Representative examples of the medical imaging devices may include an ultrasound imaging device, a computed tomography (CT) apparatus, and a magnetic resonance imaging (MRI) apparatus.

An ultrasound imaging device irradiates an ultrasound signal generated from a transducer of a probe to an object, receives information from a signal reflected from the object, and noninvasively obtains at least one image of a region (e.g., soft tissue or blood flow) inside the object. The ultrasound imaging device is used for medical purposes, such as observation of an inside part of an object, detection of foreign substances, injury measurement, etc. As the ultrasound imaging device has higher stability than other imaging devices using X-rays, is capable of displaying an image in real time, and is free from radiation exposure, the ultrasound imaging device is widely used along with other imaging devices.

SUMMARY

Additional aspects will be set forth in part in the description which follows and, in part, will be apparent from the description, or may be learned by practice of the presented embodiments of the disclosure.

According to an embodiment, a control method of an ultrasound imaging device includes displaying an ultrasound image in a display area of a touch screen. In an embodiment, the control method may include displaying a first indicator to overlap on the ultrasound image. In an embodiment, the control method may include obtaining a first touch input of moving the ultrasound image in the display area while a position of the first indicator is fixed in the display area. In an embodiment, the control method may include determining a position of the first indicator to be a first position, in response to a first position determination input of determining the position of the first indicator so as to place the first indicator at the first position on the ultrasound image. In an embodiment, the control method may include moving the ultrasound image, in response to a second touch input of moving the ultrasound image in the display area while the position of the first indicator is determined to be the first position.

According to an embodiment, an ultrasound imaging device includes a touch screen, a memory storing one or more instructions, and at least one processor configured to execute the one or more instructions stored in the memory. In an embodiment, the at least one processor may be configured to execute the one or more instructions to display an ultrasound image in a display area of the touch screen. In an embodiment, the at least one processor may be configured to execute the one or more instructions to display a first indicator to overlap on the ultrasound image. In an embodiment, the at least one processor may be configured to execute the one or more instructions to obtain a first touch input of moving the ultrasound image in the display area while a position of the first indicator is fixed. In an embodiment, the at least one processor may be configured to execute the one or more instructions to determine a position of the first indicator to be a first position, in response to a first position determination input of determining the position of the first indicator so as to place the first indicator at the first position on the ultrasound image. In an embodiment, the at least one processor may be configured to execute the one or more instructions to move the ultrasound image, in response to a second touch input of moving the ultrasound image in the display area while the position of the first indicator is determined to be the first position.

According to an embodiment, a computer-readable recording medium having recorded thereon a program for performing, on a computer, at least one of the control methods of an ultrasound imaging device is provided.

BRIEF DESCRIPTION OF THE DRAWINGS

The disclosure will become apparent and more readily appreciated from the following description, taken in conjunction with the accompanying drawings wherein like reference numerals denote like structural elements.

The above and other aspects, features, and advantages of certain embodiments of the disclosure will be more apparent from the following description taken in conjunction with the accompanying drawings, in which:

FIGS. 1A and 1B are block diagrams illustrating a configuration of an ultrasound imaging system, according to an embodiment;

FIGS. 7A and 7B are diagrams for describing that an ultrasound imaging device according to an embodiment performs preset measurement, based on a position of an indicator;

FIG. 8 is a diagram for describing that an ultrasound imaging device adjusts an angle measurement line, according to an embodiment;

DETAILED DESCRIPTION

Figure 2A:
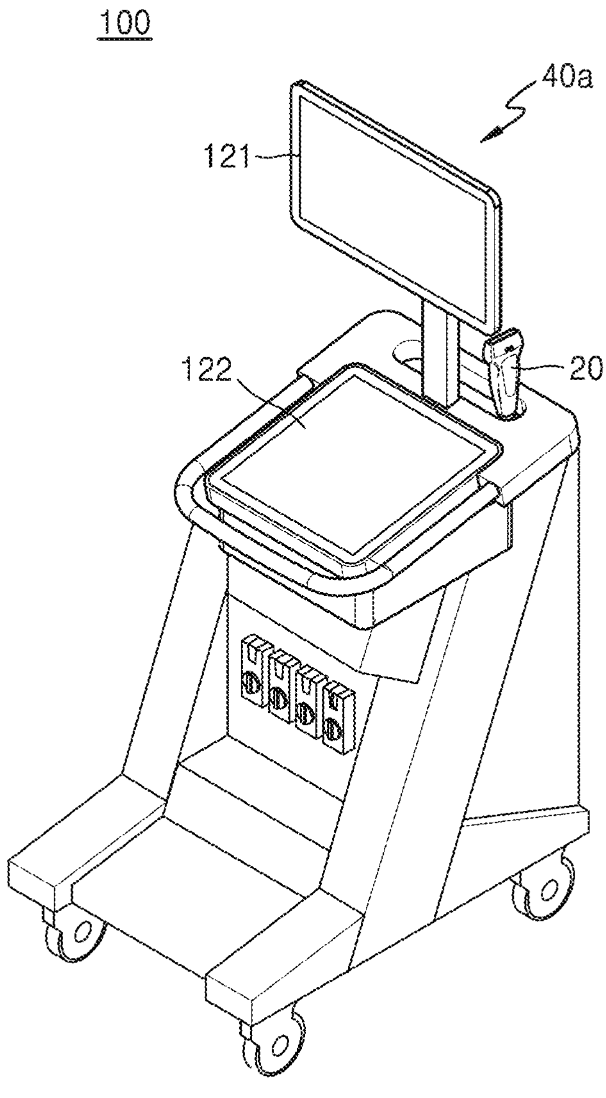
FIGS. 2A, 2B, 2C, and 2D are diagrams illustrating ultrasound imaging devices according to an embodiment.

The principles of embodiments will now be described and embodiments thereof will now be provided to clearly define the scope of claims of the disclosure and for one of ordinary skill in the art to be able to perform the embodiments. The embodiments be embodied in many different forms.

Throughout the specification, like reference numerals denote like elements. Not all elements of the embodiments are described in the specification, and general features in the art or redundant features among the embodiments are omitted. Throughout the specification, a term such as "module" or "unit" may be implemented as one of or a combination of at least two of software, hardware, and firmware, and in some embodiments, a plurality of modules or a plurality of units may be implemented as one element, or a module or a unit may include a plurality of elements.

A singular form of a noun corresponding to an item may include the item or a plurality of the items, unless the context clearly indicates otherwise.

In the disclosure, each of such phrases as "A or B," "at least one of A and B," "at least one of A or B," "A, B, or C," "at least one of A, B, and C," and "at least one of A, B, or C," may include any one of, or all possible combinations of the items enumerated together in a corresponding one of the phrases.

The term "and/or" includes any and all combinations of one or more of the associated listed elements.

The terms as "1st" and "2nd," or "first" and "second" may be used to simply distinguish a corresponding element from another, and does not limit the elements in other aspect (e.g., importance or order).

Also, the terms "front surface", "rear surface", "top surface", "bottom surface", "side surface", "left side", "right side", "upper", "lower" etc. used in the disclosure are defined based on drawings, and a shape and a location of each element are not limited due to the terms.

The terms such as "including", "comprising" or "having," etc., are intended to indicate the existence of the features, numbers, steps, actions, elements, parts, or combinations thereof disclosed in the disclosure, and are not intended to preclude the possibility that one or more other features, numbers, steps, actions, elements, parts, or combinations thereof may exist or may be added.

It will be understood that when an element is referred to as being "connected to", "coupled to", "supported by" or "in contact with" another element, it can be directly connected to, coupled to, supported by, or in contact with the other element, or it can be indirectly connected to, coupled to, supported by, or in contact with the other element via a third element.

It will be understood that when an element is referred to as being "on" or "over" another element, the element may contact the other element, or intervening elements may be present.

Hereinafter, an ultrasonic device according to various embodiments will now be described in detail with reference to attached drawings. In description with reference to attached drawings, elements that are the same or are in correspondence are rendered the same reference numeral, and redundant explanations are omitted.

In the disclosure, an image may include a medical image obtained by a medical imaging apparatus such as magnetic resonance imaging (MRI) apparatus, a computed tomography (CT) apparatus, an ultrasound imaging device, or an X-ray imaging apparatus.

In the disclosure, an "object" may be a target to be imaged and may include a human, an animal, or a part of a human or animal. For example, an object may include a body part (e.g., an organ) or a phantom.

In the disclosure, an "ultrasound image" refers to an image of an object generated or processed based on an ultrasound signal transmitted to the object and reflected therefrom.

Hereinafter, embodiments will be described in detail with reference to the drawings.

FIGS. 1A and 1B are block diagrams illustrating a configuration of an ultrasound imaging system 100, according to an embodiment.

Referring to FIGS. 1A and 1B, the ultrasound imaging system 100 may include a probe 20 and an ultrasound imaging device 40.

The ultrasound imaging device 40 may be implemented not only as a cart type but also as a portable type. Examples of a portable ultrasound imaging device may include, but are not limited to, a smart phone, a laptop computer, a personal digital assistant (PDA), and a tablet personal computer (PC) that include a probe and an application. The ultrasound imaging device 40 may be integrally implemented with a probe.

The probe 20 may include a wired probe connected to the ultrasound imaging device 40 by wire so as to communicate with the ultrasound imaging device 40 by wire, a wireless probe connected to the ultrasound imaging device 40 by wirelessly so as to communicate with the ultrasound imaging device 40 by wirelessly, and/or a hybrid probe connected to the ultrasound imaging device 40 by wire or wirelessly so as to communicate with the ultrasound imaging device 40 by wire or wirelessly.

According to various embodiments, as illustrated in FIG. 1A, the ultrasound imaging device 40 may include an ultrasound transceiving module 110, and as illustrated in FIG. 1B, the probe 20 may include the ultrasound transceiving module 110. According to various embodiments, it is possible that each of the ultrasound imaging device 40 and the probe 20 includes the ultrasound transceiving module 110.

According to various embodiments, the probe 20 may further include at least one or a combination of an image processor 130, a display 140, or an input interface 170. In the disclosure, descriptions of the ultrasound transceiving module 110, the image processor 130, the display 140, or the input interface 170 may be applied to the ultrasound transceiving module 110, the image processor 130, the display 140, or the input interface 170, which is included in the probe 20.

FIG. 1A is a block diagram illustrating the configuration of the ultrasound imaging system 100 of a case in which the probe 20 is the wired probe or the hybrid probe.

The probe 20 may include a plurality of transducers. The plurality of transducers may be aligned in a preset array to be implemented as a transducer array. The transducer array may correspond to a one-dimensional (1D) array or a two-dimensional (2D) array. The plurality of transducers may transmit an ultrasound signal to an object 10, according to a transmission signal applied from a transmission module 113. The plurality of transducers may generate a reception signal by receiving an ultrasound signal (an echo signal) reflected from the object 10. Also, the probe 20 may be integrally implemented with the ultrasound imaging device 40, or may be implemented as a separate unit connected to the ultrasound imaging device 40 by wire. Also, according to an implementation, the ultrasound imaging device 40 may be connected to one or more probes 20.

When the probe 20 is the wired probe or the hybrid probe, the probe 20 may include a cable and a connector which are connectable to a connector of the ultrasound imaging device 40.

According to an embodiment, the probe 20 may be implemented as a 2D probe. When the probe 20 is implemented as the 2D probe, the plurality of transducers included in the probe 20 may be two-dimensionally aligned to form a 2D transducer array.

For example, the 2D transducer array may include a plurality of subarrays in a first direction and a second direction different from the first direction, each of the subarrays including a plurality of transducers aligned in the first direction.

Also, when the probe 20 according to an embodiment is implemented as the 2D probe, the ultrasound transceiving module 110 may include at least one of an analog beamformer or a digital beamformer. Also, according to an embodiment, the 2D probe may include at least one or a combination of the analog beamformer or the digital beamformer, according to an implementation.

In consideration of positions and focal points of the plurality of transducers included in the probe 20, a processor 120 controls the transmission module 113 to generate transmission signals to be respectively applied to the plurality of transducers.

The processor 120 may control a reception module 115 to generate ultrasound data by performing analog-to-digital conversion on reception signals received from the probe 20, and summing the reception signals converted to digital signals, in consideration of the positions and focal points of the plurality of transducers.

When the probe 20 is implemented as the 2D probe, the processor 120 may calculate a time delay value for digital beamforming for each of the plurality of subarrays included in the 2D transducer array. Also, the processor 120 may calculate a time delay value for analog beamforming for each of transducers included in any one of the plurality of subarrays. The processor 120 may control the analog beamformer and the digital beamformer to generate a transmission signal to be applied to each of the plurality of transducers, according to the time delay values for analog beamforming and the time delay values for digital beamforming. Also, the processor 120 may control the analog beamformer to sum signals received from the plurality of transducers for each subarray, according to the time delay values for analog beamforming. Also, the processor 120 may control the ultrasound transceiving module 110 to perform analog-to-digital conversion on a result of summing the signals for each subarray. Also, the processor 120 may control the digital beamformer to generate ultrasound data by summing the signals converted to digital signals, according to the time delay values for digital beamforming.

The image processor 130 generates or processes an ultrasound image by using the generated ultrasound data.

The display 140 may display the generated ultrasound image, and various pieces of information processed by the ultrasound imaging device 40 or the probe 20. According to an implementation, the probe 20 or the ultrasound imaging device 40 may include one or more displays 140. Also, the display 140 may include a touch panel or a touch screen. Also, the display 140 may include a flexible display.

The processor 120 may control all operations of the ultrasound imaging device 40, and may control operations of elements of the ultrasound imaging device 40. The processor 120 may perform or control various operations or functions of the ultrasound imaging device 40 by executing a program or instructions stored in a memory 150. Also, the processor 120 may control operations of the ultrasound imaging device 40 by receiving a control signal from the input interface 170 or an external device.

The ultrasound imaging device 40 may include a communication module 160 and may be connected to an external device (e.g., the probe 20, a server, a medical device, or a portable device (e.g., a smart phone, a tablet PC, a wearable device, etc.)) via the communication module 160.

The communication module 160 may include one or more elements configured to enable communication with the external device. The communication module 160 may include, for example, at least one of a short-range communication module, a wired communication module, or a wireless communication module.

The communication module 160 may receive a control signal or data from the external device. The processor 120 may control an operation of the ultrasound imaging device 40, according to the control signal received via the communication module 160. Also, the processor 120 may transmit a control signal to the external device via the communication module 160, thereby controlling the external device according to the control signal. The external device may operate according to a control signal received from the ultrasound imaging device 40, or may process data received from the ultrasound imaging device 40.

A program or an application related to the ultrasound imaging device 40 may be installed in the external device. The program or the application installed in the external device may control the ultrasound imaging device 40, or may operate according to a control signal or data received from the ultrasound imaging device 40.

The external device may receive or download the program or the application related to the ultrasound imaging device 40 from the ultrasound imaging device 40, the probe 20, or a server, and may install and execute the program or the application in the external device. The ultrasound imaging device 40, the probe 20, or the server which provides the program or the application may include a recording medium that stores an instruction, a command, an installation file, an execution file, related data, or the like of the program or the application. The external device having the program or the application installed therein may be sold.

The memory 150 may store various pieces of data or programs for operating and controlling the ultrasound imaging device 40, input/output ultrasound data, ultrasound images, and the like.

The input interface 170 may receive a user input for controlling the ultrasound imaging device 40. For example, the user input may include, but is not limited to, an input of manipulating a button, a keypad, a mouse, a trackball, a jog switch, a knop, or the like, an input of touching a touch pad or a touch screen, a voice input, a motion input, a biometric information input (e.g., iris recognition or fingerprint recognition), and the like.

FIG. 1B is a control block diagram of the ultrasound imaging system 100 of a case in which the probe 20 is the wireless probe or the hybrid probe.

According to various embodiments, the ultrasound imaging device 40 of FIG. 1B may be substituted with the ultrasound imaging device 40 described with reference to FIG. 1A.

According to various embodiments, the probe 20 of FIG. 1A may be substituted with the probe 20 to be described with reference to FIG. 1B.

The probe 20 may include a display 112, the transmission module 113, a battery 114, a transducer 117, a charging module 116, a reception module 115, an input interface 109, a processor 118, and a communication module 119. FIG. 1B illustrates that the probe 20 includes all of the transmission module 113 and the reception module 115, but, according to an implementation, the probe 20 may include only a portion of configurations of the transmission module 113 and the reception module 115, and a portion of the configurations of the transmission module 113 and the reception module 115 may be included in the ultrasound imaging device 40. Also, according to an embodiment, the probe 20 may further include the image processor 130.

The transducer 115 may include a plurality of transducers. The plurality of transducers may be aligned in a preset array to be implemented as a transducer array. The transducer array may correspond to a 1 D array or a 2D array. The plurality of transducers may transmit an ultrasound signal to an object 10, according to a transmission signal applied from a transmission module 113. The plurality of transducers may form or generate an electric reception signal by receiving an ultrasound signal reflected from the object 10.

The charging module 116 may charge the battery 114. The charging module 116 may receive power from an external source. According to an embodiment, the charging module 116 may wirelessly receive power. Also, according to an embodiment, the charging module 116 may receive power by wire. The charging module 116 may deliver the received power to the battery 114.

In consideration of positions and focal points of the plurality of transducers, the processor 118 controls the transmission module 113 to generate or form transmission signals to be respectively applied to the plurality of transducers.

The processor 118 controls the reception module 115 to generate ultrasound data by performing analog-to-digital conversion on reception signals received from the transducer 117, and summing the reception signals converted to digital signals, in consideration of the positions and focal points of the plurality of transducers. According to an embodiment, when the probe 20 includes the image processor 130, an ultrasound image may be generated by using the generated ultrasound data.

When the probe 20 is implemented as the 2D probe, the processor 118 may calculate a time delay value for digital beamforming for each of the plurality of subarrays included in the 2D transducer array. Also, the processor 118 may calculate a time delay value for analog beamforming for each of transducers included in any one of the plurality of subarrays. The processor 118 may control a analog beamformer and a digital beamformer to generate a transmission signal to be applied to each of the plurality of transducers, according to the time delay values for analog beamforming and the time delay values for digital beamforming. Also, the processor 118 may control the analog beamformer to sum signals received from the plurality of transducers for each subarray, according to the time delay values for analog beamforming. Also, the processor 118 may control the ultrasound transceiving module 110 to perform analog-to-digital conversion on a result of summing the signals for each subarray. Also, the processor 118 may control the digital beamformer to generate ultrasound data by summing the signals converted to digital signals, according to the time delay values for digital beamforming.

The processor 118 may control all operations of the probe 20, and may control operations of elements of the probe 20. The processor 118 may perform or control various operations or functions of the probe 20 by executing a program or instructions stored in a memory 111. Also, the processor 118 may control operations of the probe 20 by receiving a control signal from the input interface 109 of the probe 20 or an external device (e.g.: the ultrasound imaging device 40). Also, the processor 118 may control operations of the probe 20 by receiving a control signal from the input interface 109 or the external device. The input interface 109 may receive a user input for controlling the probe 20. For example, the user input may include, but is not limited to, an input of manipulating a button, a keypad, a mouse, a trackball, a jog switch, a knop, or the like, an input of touching a touch pad or a touch screen, a voice input, a motion input, a biometric information input (e.g., iris recognition or fingerprint recognition), and the like.

The display 112 may display an ultrasound image generated by the probe 20, an ultrasound image generated by processing ultrasound data generated in the probe 20, an ultrasound image received from the ultrasound imaging device 40, or various pieces of information processed by the ultrasound imaging system 100. Also, the display 112 may further display state information of the probe 20. The state information of the probe 20 may include at least one of device information of the probe 20, battery state information of the probe 20, frequency band information of the probe 20, output information of the probe 20, information indicating normality or abnormality of the probe 20, setting information of the probe 20, or temperature information of the probe 20.

According to an implementation, the probe 20 may include one or more displays 112. Also, the display 112 may include a touch panel or a touch screen. Also, the display 112 may include a flexible display.

The communication module 119 may wirelessly transmit the generated ultrasound data or the ultrasound image to the ultrasound imaging device 40 a wireless network. Also, the communication module 119 may receive a control signal and data from the ultrasound imaging device 40.

The ultrasound imaging device 40 may receive the ultrasound data or the ultrasound image from the probe 20.

In an embodiment, when the probe 20 includes the image processor 130 capable of generating an ultrasound image by using ultrasound data, the probe 20 may transmit ultrasound data, or an ultrasound image generated by the image processor 130 to the ultrasound imaging device 40.

In an embodiment, when the probe 20 does not include the image processor 130 capable of generating an ultrasound image by using ultrasound data, the probe 20 may transmit ultrasound data to the ultrasound imaging device 40. Ultrasound data may include ultrasound raw data, and an ultrasound image may indicate ultrasound image data.

The ultrasound imaging device 40 may include the processor 120, the image processor 130, the display 140, the memory 150, the communication module 160, and the input interface 170.

The image processor 130 generates or processes an ultrasound image by using ultrasound data received from the probe 20.

The display 140 may display an ultrasound image received from the probe 20, an ultrasound image generated by processing ultrasound data received from the probe 20, or various pieces of information processed by the ultrasound imaging system 100. According to an implementation, the ultrasound imaging device 40 may include one or more displays 140. Also, the display 140 may include a touch panel or a touch screen. Also, the display 140 may include a flexible display.

The processor 120 may control all operations of the ultrasound imaging device 40, and may control operations of elements of the ultrasound imaging device 40. The processor 120 may perform or control various operations or functions of the ultrasound imaging device 40 by executing a program or an application stored in a memory 150. Also, the processor 120 may control operations of the ultrasound imaging device 40 by receiving a control signal from the input interface 170 or an external device.

The ultrasound imaging device 40 may include the communication module 160 and may be connected to an external device (e.g., the probe 20, a server, a medical device, or a portable device (e.g., a smart phone, a tablet PC, a wearable device, etc.)) via the communication module 160.

The communication module 160 may include one or more elements configured to enable communication with the external device. The communication module 160 may include, for example, at least one of a short-range communication module, a wired communication module, or a wireless communication module.

The communication module 160 of the ultrasound imaging device 40 and the communication module 119 of the probe 20 may communicate by using a network or may communicate by using a short-range wireless communication method. For example, the communication module 160 of the ultrasound imaging device 40 and the communication module 119 of the probe 20 may communicate by using at least one of wireless data communication methods including wireless local area network (LAN), Wi-Fi, Bluetooth, ZigBee, Wi-Fi direct (WFD), infrared data association (IrDA), Bluetooth low energy (BLE), near field communication (NFC), wireless broadband Internet (WiBro), world interoperability for microwave access (WiMAX), shared wireless access protocol (SWAP), wireless gigabit alliance (WiGig), radio frequency (RF) communication, or 60-GHz mmWave short-range communication.

To this end, the communication module 160 of the ultrasound imaging device 40 and the communication module 119 of the probe 20 may each include at least one of a wireless LAN communication module, a Wi-Fi communication module, a Bluetooth communication module, a ZigBee communication module, a WFD communication module, an IrDA communication module, a BLE communication module, an NFC communication module, a WiBro communication module, a WiMAX communication module, a SWAP communication module, a WiGig communication module, a RF communication module, or a 60-GHz mmWave short-range communication module.

In an embodiment, the probe 20 may transmit device information (e.g.: identification (ID) information) of the probe 20 to the ultrasound imaging device 40 by using a first communication method (e.g.: BLE), and may be wirelessly paired with the ultrasound imaging device 40. Also, the probe 20 may transmit ultrasound data and/or an ultrasound image to the paired ultrasound imaging device 40.

The device information of the probe 20 may include various pieces of information related to a serial number, a model name, or a battery state of the probe 20.

The ultrasound imaging device 40 may receive the device information (e.g.: ID information) of the probe 20 from the probe 20 by using the first communication method (e.g.: BLE), and may be wirelessly paired with the probe 20. Also, the ultrasound imaging device 40 may transmit an activation signal to the paired probe 20, and may receive ultrasound data and/or an ultrasound image from the probe 20. Here, the activation signal may include a signal for controlling an operation of the probe 20.

In an embodiment, the probe 20 may transmit the device information (e.g.: ID information) of the probe 20 to the ultrasound imaging device 40 by using the first communication method (e.g.: BLE), and may be wirelessly paired with the ultrasound imaging device 40. Also, the probe 20 may transmit ultrasound data and/or an ultrasound image to the ultrasound imaging device 40 paired by the first communication method, by using a second communication method (e.g.: 60-GHz mmWave, Wi-Fi).

The ultrasound imaging device 40 may receive the device information (e.g.: ID information) of the probe 20 from the probe 20 by using the first communication method (e.g.: BLE), and may be wirelessly paired with the probe 20. Also, the ultrasound imaging device 40 may transmit an activation signal to the paired probe 20, and may receive ultrasound data and/or an ultrasound image from the probe 20 by using the second communication method (e.g.: 60-GHz mmWave, Wi-Fi).

According to an embodiment, the first communication method used to pair the probe 20 with the ultrasound imaging device 40 may have a frequency band lower than a frequency band of the second communication method used for the probe 20 to transmit ultrasound data and/or an ultrasound image to the ultrasound imaging device 40.

The display 140 of the ultrasound imaging device 40 may display user interfaces (UIs) indicating the device information of the probe 20. For example, the display 140 may display ID information of the probe 20, a pairing method indicating a method of pairing with the probe 20, a data communication state between the probe 20 and the ultrasound imaging device 40, a method of performing data communication with the ultrasound imaging device 40, a UI indicating a battery state of the probe 20, or the like.

When the probe 20 includes the display 112, the display 112 of the probe 20 may display a UI indicating the device information of the probe 20. For example, the display 112 may display ID information of the probe 20, a pairing method indicating a method of pairing with the probe 20, a data communication state between the probe 20 and the ultrasound imaging device 40, a method of performing data communication with the ultrasound imaging device 40, a UI indicating a battery state of the probe 20, or the like.

The communication module 160 may receive a control signal or data from the external device. The processor 120 may control an operation of the ultrasound imaging device 40, according to the control signal received via the communication module 160.

Also, the processor 120 may transmit a control signal to the external device via the communication module 160, thereby controlling the external device according to the control signal. The external device may operate according to a control signal received from the ultrasound imaging device 40, or may process data received from the ultrasound imaging device 40.

The external device may receive or download the program or the application related to the ultrasound imaging device 40 from the ultrasound imaging device 40, the probe 20, or a server, and may install and execute the program or the application in the external device. The ultrasound imaging device 40, the probe 20, or the server which provides the program or the application may include a recording medium that stores an instruction, a command, an installation file, an execution file, related data, or the like of the program or the application. The external device having the program or the application installed therein may be sold.

The memory 150 may store various pieces of data or programs for operating and controlling the ultrasound imaging device 40, input/output ultrasound data, ultrasound images, and the like.

Examples of the ultrasound imaging system 100 according to an embodiment will now be described with reference to FIGS. 2A, 2B, 2C, and 2D.

FIGS. 2A, 2B, 2C, and 2D are diagrams illustrating ultrasound imaging devices according to an embodiment.

Figure 2B:
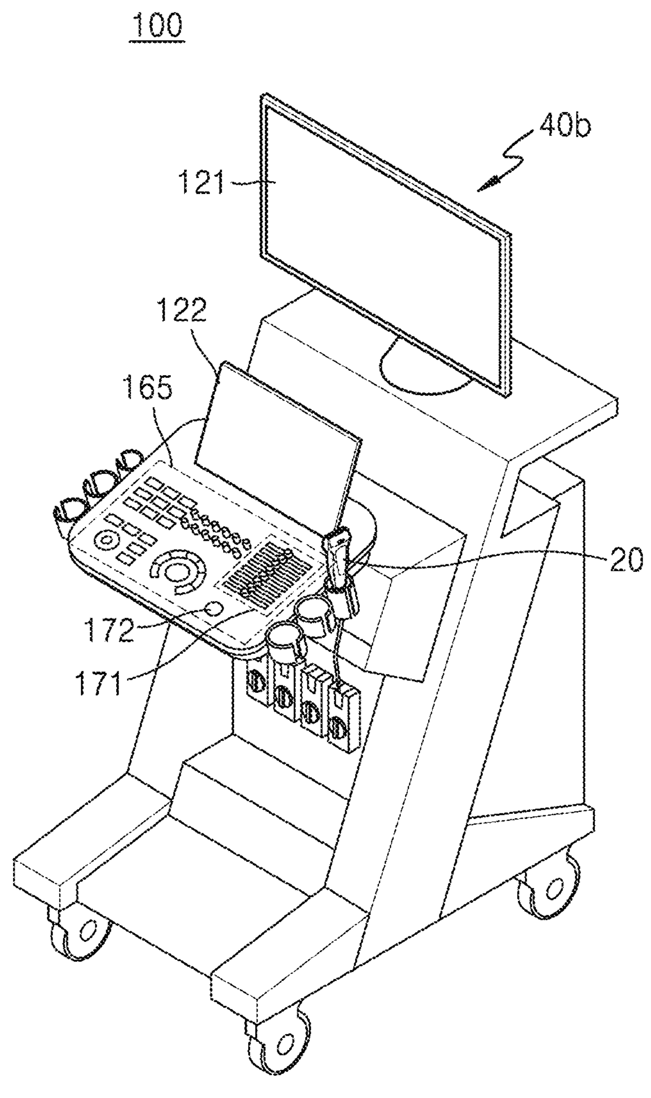

Referring to FIGS. 2A and 2B, each of ultrasound imaging devices 40*a* and 40*b* may include a main display 121 and a sub-display 122. Each of the main display 121 and the sub-display 122 may correspond to the display 140 of FIGS. 1A and 1B. At least one of the main display 121 or the sub-display 122 may be implemented as a touch screen. At least one of the main display 121 or the sub-display 122 may display an ultrasound image, or various pieces of information processed by the ultrasound imaging device 40*a* or 40*b*. Also, at least one of the main display 121 or the sub-display 122 is implemented as a touch screen and provides a graphical user interface (GUI), thereby receiving an input of data for controlling the ultrasound imaging device 40*a* or 40*b* from a user. For example, the main display 121 may display an ultrasound image, and the sub-display 122 may display a control panel in a GUI form so as to control a display of the ultrasound image. The sub-display 122 may receive an input of data for controlling a display of an image, via the control panel displayed in the GUI form. For example, a time gain compensation (TGC) button, a lateral gain compensation (LGC) button, a Freeze button, a trackball, a jog switch, a knop, or the like may be provided in the GUI form in the sub-display 122.

The ultrasound imaging device 40*a* or 40*b* may control a display of an ultrasound image displayed on the main display 121, by using input control data. Also, the ultrasound imaging device 40*a* or 40*b* may be connected to the probe 20 by wire or wirelessly, thereby transmitting or receiving an ultrasound signal to or from an object.

Referring to FIG. 2B, the ultrasound imaging device 40*b* may further include a control panel 165 as well as the main display 121 and the sub-display 122. The control panel 165 may include a button, a trackball, a jog switch, a knop, or the like, and may receive an input of data for controlling the ultrasound imaging device 40*b* from a user. For example, the control panel 165 may include a TGC button 171, a Freeze button 172, or the like. The TGC button 171 is a button for setting a TGC value for each depth of an ultrasound image. Also, when the ultrasound imaging device 40*b* detects an input to the Freeze button 172 while an ultrasound image is being scanned, the ultrasound imaging device 40*b* may maintain a state in which a frame image of a time point corresponding thereto is displayed, may capture the frame image of the time point, or may store the frame image of the time point.

The button, the trackball, the jog switch, the knop, or the like included in the control panel 165 may be provided in a GUI to the main display 121 or the sub-display 122. Also, the ultrasound imaging device 40*a* or 40*b* may be connected to the probe 20, thereby transmitting or receiving an ultrasound signal to or from an object.

Also, the ultrasound imaging device 40*a* or 40*b* may include an input/output interface of various types including as a speaker, a light-emitting diode (LED), a vibration device, or the like. For example, the ultrasound imaging device 40*a* or 40*b* may output, via the input/output interface, various pieces of information in the form of a graphic, sound, a vibration, or the like. Also, the ultrasound imaging device 40*a* or 40*b* may output, via the input/output interface, various notifications or data.

Figure 2C:
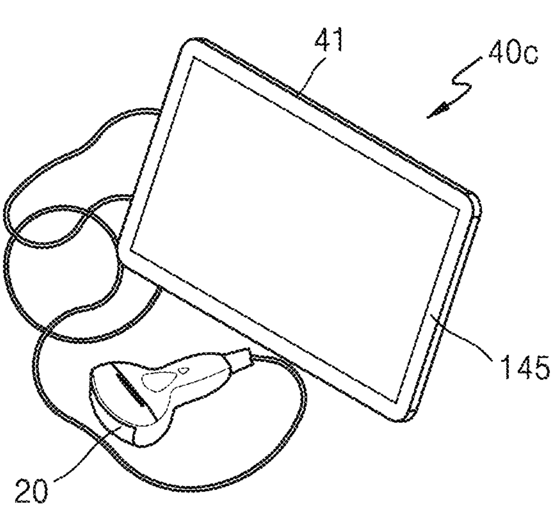
Figure 2D:
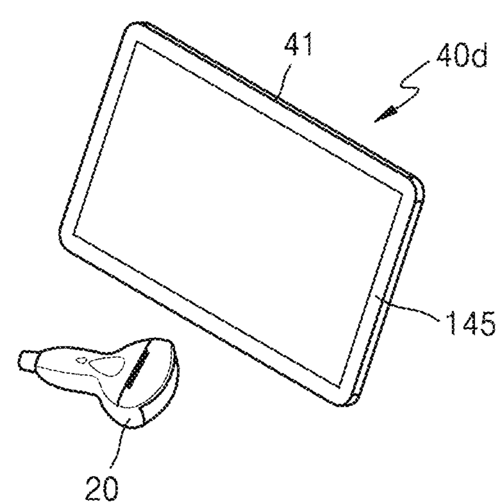

Referring to FIGS. 2C and 2D, the ultrasound imaging device 40*a* or 40*b* may be implemented to be portable. Examples of a portable ultrasound imaging device 40*c* or 40*d* may include, but are not limited to, a smart phone, a laptop computer, a PDA, a tablet PC, or the like which includes a probe and an application.

The portable ultrasound imaging device 40*c* may include a main body 41. Referring to FIG. 2C, the probe 20 may be connected by wire to one side of the main body 41. To this end, the main body 41 may include a connection terminal to which a cable connected to the probe 20 is detachable. The probe 20 may include a cable including a connection terminal that is connectable to the main body 41.

Referring to FIG. 2D, the probe 20 may be wirelessly connected to the ultrasound imaging device 40*d*. The main body 41 may include an input/output interface (e.g.: a touch screen). The input/output interface may display an ultrasound image, various pieces of information processed by an ultrasound imaging device, a GUI, or the like.

The ultrasound imaging device 40*d* and the probe 20 may establish communication or be paired with each other by using short-range wireless communication. For example, the ultrasound imaging device 40*d* and the probe 20 may perform communication by using Bluetooth, BLE, Wi-Fi, WFD, or the like.

The ultrasound imaging device 40*c* or 40*d* may control the probe 20 and output information related to the probe 20, by executing a program or an application related to the probe 20. The ultrasound imaging device 40*c* or 40*d* in communication with a preset server may perform an operation related to the probe 20. The probe 20 may be registered in the ultrasound imaging device 40*c* or 40*d* or may be registered in the preset server. The ultrasound imaging device 40*c* or 40*d* may communicate with the registered probe 20, and may perform an operation related to the probe 20.

Also, the ultrasound imaging device 40*c* or 40*d* may include an input/output interface of various types including as a speaker, a LED, a vibration device, or the like. For example, the ultrasound imaging device 40*c* or 40*d* may output, via the input/output interface, various pieces of information in the form of a graphic, sound, a vibration, or the like. Also, the ultrasound imaging device 40*c* or 40*d* may output, via the input/output interface, various notifications or data.

According to an embodiment, the ultrasound imaging device 40*a*, 40*b*, 40*c*, or 40*d* may process an ultrasound image or may obtain auxiliary information from the ultrasound image, by using an artificial intelligence (AI) model. According to an embodiment, the ultrasound imaging device 40*a*, 40*b*, 40*c*, or 40*d* may generate an ultrasound image or perform processing such as correction, image-quality enhancement, encoding, decoding, or the like on an ultrasound image, by using the AI model. Also, according to an embodiment, the ultrasound imaging device 40*a*, 40*b*, 40*c*, or 40*d* may perform, from an ultrasound image, a definition of a reference line, obtainment of anatomical information, obtainment of lesion information, surface extraction, a boundary definition, length measurement, area measurement, volume measurement, annotation generation, or the like, by using the AI model.

The AI model may be arranged in the ultrasound imaging device 40*a*, 40*b*, 40*c*, or 40*d* or may be arranged in a server.

The AI model may be implemented by using various artificial neural networks or deep neural networks. Also, the AI model may be trained and generated by using various machine learning algorithms or deep learning algorithms. The AI model may be implemented by using a model including a convolutional neural network (CNN), a recurrent neural network (RNN), a generative adversarial network (GAN), a long short-term memory (LSTM), or the like.

Figure 2E:
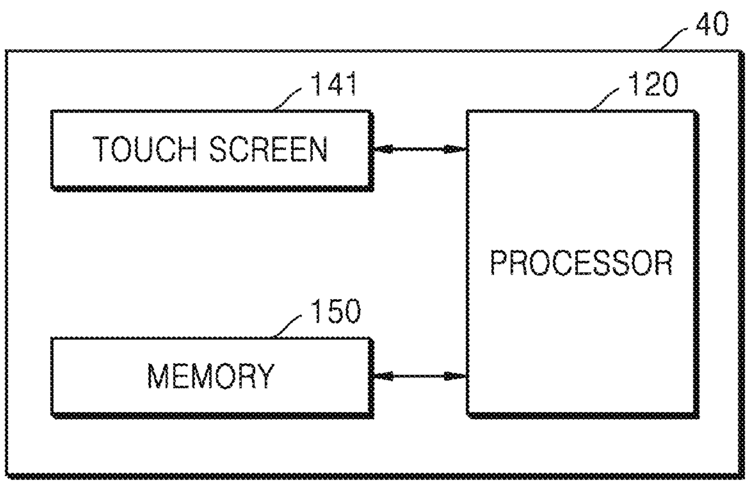
FIG. 2E is a diagram illustrating a detailed configuration of an ultrasound imaging device according to an embodiment.

FIG. 2E is a block diagram illustrating a configuration of an ultrasound imaging device according to an embodiment. According to various embodiments, the ultrasound imaging device 40 shown in FIG. 2E may be substituted with the ultrasound imaging device 40 described with reference to FIGS. 1A and 1B.

Referring to FIG. 2E, the ultrasound imaging device 40 may include the processor 120, a touch screen 141, and the memory 150. The ultrasound imaging device 40, the processor 120, and the memory 150 may be electrically and/or physically connected to each other.

Elements shown in FIG. 2E are merely an embodiment, and elements included in the ultrasound imaging device 40 are not limited to those shown in FIG. 2E. The ultrasound imaging device 40 according to an embodiment may not include some of the elements shown in FIG. 2E, or may further include elements not shown in FIG. 2E. Also, redundant descriptions of the elements shown in FIG. 2E are not provided.

The touch screen 141 may indicate an element configured to receive a touch input of a user. In an embodiment, the touch screen 141 may be implemented as a touch screen, or may correspond to the display 140 of FIGS. 1A and 1B which includes a touch screen configured to receive a touch input of a user. In an embodiment, the touch screen 141 may display an ultrasound image and an indicator, based on a control by the processor 120. In an embodiment, the touch screen 141 may receive a touch input of a user with respect to at least one of the ultrasound image or the indicator which are displayed on the touch screen 141.

In an embodiment, instructions or program codes for performing functions or operations of the ultrasound imaging device 40 may be stored in the memory 150. In an embodiment, at least one instruction, an algorithm, a data structure, program codes, and an application program which are stored in the memory 150 may be implemented with any programming or scripting language such as C, C++, Java, assembler, or the like.

In an embodiment, the memory 400 may include at least one of a flash memory-type memory, a hard disk-type memory, a multimedia card micro-type memory, a card-type memory (e.g., secure digital (SD) or extreme digital (XD) memory), a random access memory (RAM), a static random access memory (SRAM), a read-only memory (ROM), an electrically erasable programmable read-only memory (EEPROM), a programmable read-only memory (PROM), a mask ROM, flash ROM, a hard disk drive (HDD), or a solid state drive (SSD).

The processor 120 may execute one or more instructions of the program stored in the memory 150. In an embodiment, the processor 120 may include a hardware element configured to perform calculation, logic and input/output computation, and signal processing. In an embodiment, the processor 120 may include at least one of, but is not limited to, a central processing unit, a microprocessor, a graphics processing unit, application specific integrated circuits (ASICs), digital signal processors (DSPs), digital signal processing devices (DSPDs), programmable logic devices (PLDs), or field programmable gate arrays (FPGAs).

In an embodiment, the processor 120 may execute the one or more instructions to display an ultrasound image in a display area of the touch screen 141.

In an embodiment, the processor 120 may execute the one or more instructions to display a first indicator to overlap on an ultrasound image.

In an embodiment, the processor 120 may execute the one or more instructions to obtain a user input of selecting a measurement mode. In an embodiment, the processor 120 may execute the one or more instructions to display a first indicator to overlap on an ultrasound image, the first indicator corresponding to the selected measurement mode.

In an embodiment, the processor 120 may execute the one or more instructions to display the ultrasound image indicating a zoomed-in area around the first indicator overlapped on the ultrasound image.

In an embodiment, the processor 120 may execute the one or more instructions to obtain, while a position of the first indicator is fixed, a first touch input of moving the ultrasound image on the display area.

In an embodiment, the processor 120 may execute the one or more instructions to determine the position of the first indicator to be a first position, in response to a first position determination input of determining the position of the first indicator so as to place the first indicator at the first position on the ultrasound image.

In an embodiment, the processor 120 may execute the one or more instructions to display a second indicator to overlap on the ultrasound image. In an embodiment, the processor 120 may execute the one or more instructions to move the display area of the ultrasound image, in response to a second touch input of moving the ultrasound image in the display area while the position of the first indicator is determined to be the first position.

In an embodiment, the processor 120 may execute the one or more instructions to display the second indicator to overlap on the ultrasound image. In an embodiment, the processor 120 may execute the one or more instructions to move the ultrasound image while a position of the second indicator is fixed in the display area in response to the second touch input.

In an embodiment, the processor 120 may execute the one or more instructions to determine the position of the second indicator to be a second position, in response to a second position determination input of determining the position of the second indicator so as to place the second indicator at the second position on the ultrasound image.

In an embodiment, when the position of the first indicator is determined to be the first position on the ultrasound image, the processor 120 may execute the one or more instructions to display the ultrasound image indicating a zoomed-in area around the second indicator overlapped on the ultrasound image.

In an embodiment, the processor 120 may execute the one or more instructions to move the ultrasound image while the position of the second indicator is fixed in the display area in response to the second touch input.

In an embodiment, the processor 120 may execute the one or more instructions to display a line to overlap on the displayed ultrasound image, the line connecting between the first indicator and the second indicator.

In an embodiment, the processor 120 may execute the one or more instructions to fix the first indicator at the first position and may move the first indicator with the ultrasound image.

In an embodiment, the first indicator may execute the one or more instructions to include an indicator configured to determine at least one of a position of a scan line of a Doppler image included in the ultrasound image or a position of a sample volume gate of the Doppler image.

In an embodiment, the processor 120 may execute the one or more instructions to display a third indicator to overlap on the ultrasound image, the third indicator being configured to determine an angle of a sample volume gate according to a stream line corresponding to a blood flow of an object in the Doppler image. In an embodiment, the processor 120 may execute the one or more instructions to rotate the third indicator, while the display area of the ultrasound image is fixed, in response to a third touch input of changing the angle of the sample volume gate.

In this manner, the ultrasound imaging device 40 according to an embodiment may determine a position of an indicator, based on a display area of an ultrasound image being moved. Accordingly, user convenience may be improved by preventing that the indicator is blocked by a user's hand, etc. during a touch input process and thus an undesired position on the ultrasound image is determined to be a position of the indicator.

An operation of the processor 120 according to an embodiment may be understood as an operation of the ultrasound imaging device 40 to be described below. In other words, the processor 120 may perform operations and functions of the ultrasound imaging device 40 which are to be described below according to various embodiments with reference to drawings.

Figure 3:
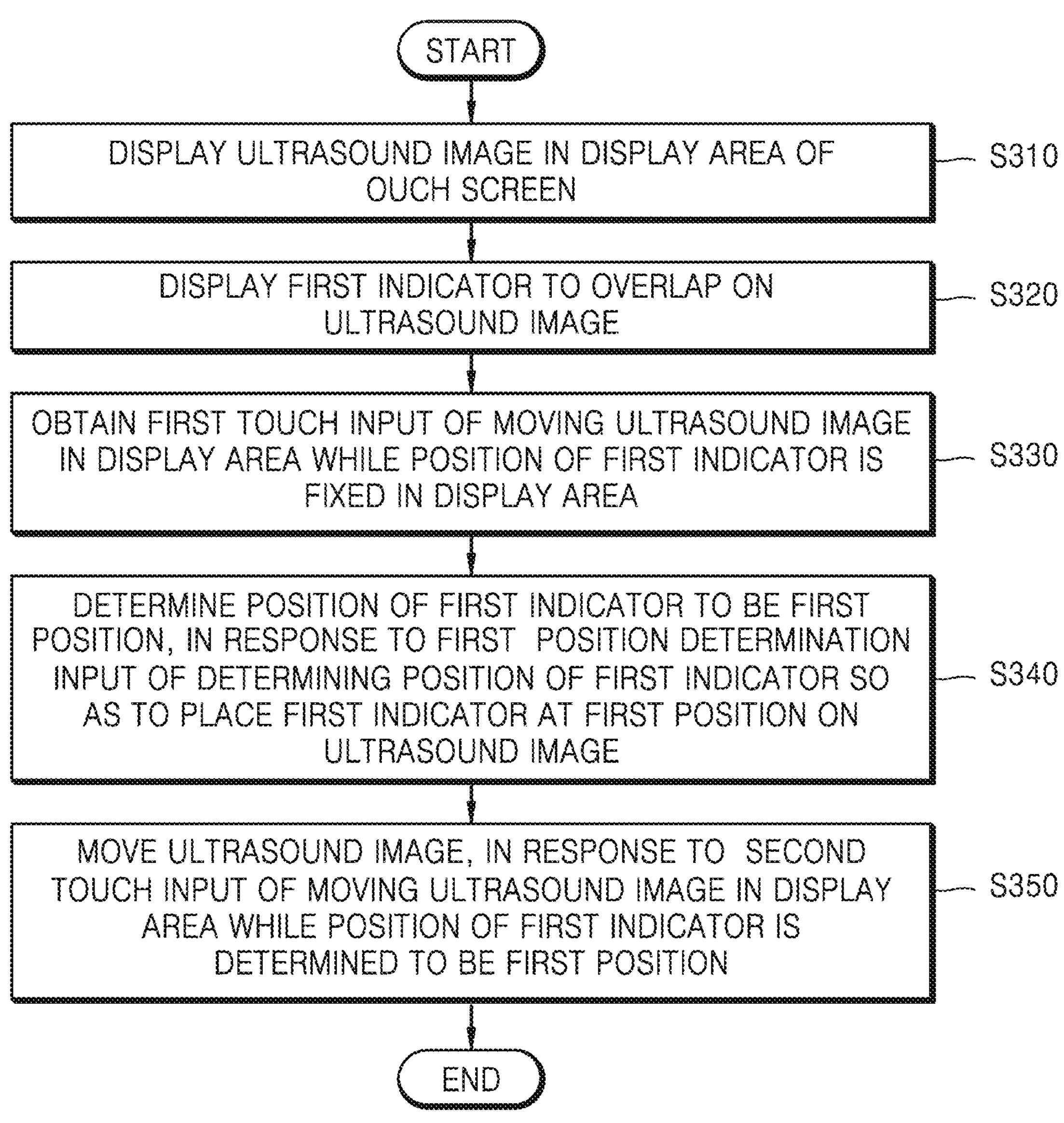
FIG. 3 is a flowchart for describing a control method of an ultrasound imaging device according to an embodiment.

FIG. 3 is a flowchart for describing a control method of the ultrasound imaging device 40, according to an embodiment. The control method of the ultrasound imaging device 40 to be described with reference to FIG. 3 may be substituted with a control method of the ultrasound imaging device 40 described with reference to FIGS. 1A and 1B.

In operation S310, the ultrasound imaging device 40 may display an ultrasound image in a display area of the touch screen 141. In an embodiment, the ultrasound imaging device 40 may receive the ultrasound image from the probe 20, and may display the received ultrasound image in the display area of the touch screen 141. Here, the display area may include a preset area of the touch screen 141 in which an ultrasound image is displayed. In other words, the ultrasound imaging device 40 may display a part or an entirety of the ultrasound image via the display area that is the preset area of the touch screen 141.

In an embodiment, the ultrasound image may include a real-time ultrasound image. The real-time ultrasound image may indicate an ultrasound image being displayed in real time via the ultrasound imaging device 40 while the ultrasound imaging device 40 receives the ultrasound image from the probe 20.

In an embodiment, the ultrasound imaging device 40 or the probe 20 may obtain, via the input interface 170 or the touch screen 141, a user input of adjusting an ultrasound parameter for the real-time ultrasound image, while the real-time ultrasound image is displayed. The ultrasound parameter may include information used to adjust a resolution, an image quality, and a display area of the ultrasound image. For example, the ultrasound parameter may include, but is not limited to, at least one of a depth, a position of a focus, TGC, LGC or a gain of the ultrasound image. In an embodiment, the ultrasound imaging device 40 may receive an ultrasound image corresponding to the adjusted ultrasound parameter from the probe 20, and may display the received ultrasound image.

In an embodiment, the ultrasound image may include a pre-stored ultrasound image. The pre-stored ultrasound image may indicate an image that is received by the ultrasound imaging device 40 or the probe 20 from an external electronic device and is stored in the memory 150.

In an embodiment, the pre-stored ultrasound image may include an ultrasound image generated from ultrasound raw data stored in the memory 150. In an embodiment, the ultrasound imaging device 40 may obtain a user input of adjusting an ultrasound parameter for the pre-stored ultrasound image, via the input interface 170 or the touch screen 141. In an embodiment, the ultrasound imaging device 40 may generate an ultrasound image corresponding to the adjusted ultrasound parameter from the ultrasound raw data stored in the memory 150, and may display the generated ultrasound image.

In operation S320, the ultrasound imaging device 40 may display a first indicator to overlap on the ultrasound image. In an embodiment, an indicator may include a GUI that is displayed to overlap in an area of the touch screen 141 in which the ultrasound image is displayed. In an embodiment, the indicator may be displayed on the touch screen 141 so as to be distinguished from the ultrasound image by including a boundary and/or an edge or including a color and/or a contrast contrasting with the ultrasound image. In an embodiment, the ultrasound imaging device 40 may display both at least one indication line and the indicator to overlap on the ultrasound image, the least one indication line for identifying or specifying a position of the indicator displayed on the touch screen 141 or the ultrasound image.

In an embodiment, the ultrasound imaging device 40 may obtain a user input of selecting a measurement mode. In an embodiment, the measurement mode may indicate an operation or a function of the ultrasound imaging device 40 which performs, on an ultrasound image, preset measurement with respect to the ultrasound image. In an embodiment, the user input of selecting the measurement mode may include a user input of selecting one of a plurality of preset measurements with respect to the ultrasound image. For example, the plurality of preset measurements may include length measurement, angle measurement, width measurement, or the like with respect to an object of the ultrasound image, but the disclosure is not limited thereto. In an embodiment, a plurality of indicators respectively for performing the plurality of preset measurements may be preset, and the ultrasound imaging device 40 may display an indicator to overlap on an ultrasound image, the indicator corresponding to a measurement mode selected based on a user input.

In an embodiment, the ultrasound imaging device 40 may display the first indicator at a preset position on the touch screen 141, thereby determining a position at which the first indicator overlaps on an ultrasound image. For example, the ultrasound imaging device 40 may display the first indicator to be positioned at a very center of an ultrasound image displayed in a very center display area on the touch screen 141. However, the disclosure is not limited to the example above, and the first indicator may be displayed at a random position on the touch screen 141.

In an embodiment, the ultrasound imaging device 40 may apply an ultrasound image to an AI model, thereby determining a position at which the first indicator overlaps on an ultrasound image. In an embodiment, the AI model may include a model trained to output, by receiving an input of at least one of an ultrasound image or a selected measurement mode, a position at which the first indicator overlaps on the ultrasound image. In an embodiment, the ultrasound imaging device 40 may display, on the touch screen 141, the first indicator to overlap at the position on the ultrasound image which is obtained from the AI model.

In operation S330, the ultrasound imaging device 40 may obtain a first touch input of moving the ultrasound image in the display area while a position of the first indicator is fixed in the display area.

In an embodiment, the ultrasound imaging device 40 may move the ultrasound image in the display area while the position of the first indicator is fixed in response to the first touch input. Here, that an ultrasound image is moved may include that an area of the ultrasound image displayed in a display area is changed from a first area to a second area. In other words, the ultrasound imaging device 40 may move the ultrasound image in the display area by changing the area of the ultrasound image displayed in the display area from the first area to the second area.

In an embodiment, an entire area of the ultrasound image may be displayed in the display area. In this case, as the ultrasound imaging device 40 moves the ultrasound image in response to the first touch input of moving the ultrasound image in the display area, a certain area of the entire area of the ultrasound image displayed in the display area may be excluded, and the ultrasound imaging device 40 may display, in the display area, the ultrasound image to which a new area that was not included in the ultrasound image displayed in the display area is added.

In an embodiment, a certain area of an ultrasound image may be displayed via the touch screen 141. For example, when the area is zoomed-in in an entire area of the ultrasound image, the ultrasound image indicating the zoomed-in area may be displayed in the display area, and other areas excluding the zoomed-in area in the ultrasound image may not displayed in the display area. In this case, as the ultrasound imaging device 40 moves the ultrasound image in response to the first touch input of moving the ultrasound image in the display area, the ultrasound imaging device 40 may display, in the display area, the ultrasound image indicating a zoomed-in area excluding an area from a zoomed-in area of the ultrasound image displayed in the display area, and including an area (or an entirety) of other areas of the zoomed-in area, and thus, may move the ultrasound image. However, the disclosure is not limited to the example above, and the ultrasound image indicating a zoomed-in area from which an entirety of a zoomed-in area is excluded and which includes an area (or an entirety) of other areas may be displayed.

In an embodiment, the ultrasound imaging device 40 may obtain a touch input for an ultrasound image via the touch screen 141. In an embodiment, the touch input for an ultrasound image may include at least one of a touch input being input to the display area or a touch input being input to an area other than the display area on the touch screen 141. For example, the touch input for an ultrasound image may include, but is not limited to, a drag input, a pinch input, a swipe input, a rotation input, a long-press input, or a double-tap input, which is input via the touch screen 141.

In an embodiment, the first touch input from among the touch input for an ultrasound image may include a touch input for moving the ultrasound image displayed in the display area. For example, the first touch input may include, but is not limited to, a drag input of moving the ultrasound image to the left or moving the ultrasound image to the right. In an embodiment, the ultrasound imaging device 40 may move the ultrasound image, based on a user input obtained via the input interface 170.

In an embodiment, when the first touch input is obtained, the ultrasound imaging device 40 may move the ultrasound image, in response to the obtained first touch input. In an embodiment, the ultrasound imaging device 40 may determine a movement direction and a movement distance, based on the first touch input. In an embodiment, the ultrasound imaging device 40 may determine an area of the ultrasound image which is displayed in the display area as the ultrasound image is moved based on the determined movement direction and movement distance.

In an embodiment, the ultrasound imaging device 40 may move the ultrasound image while a position of the first indicator is fixed in the display area. In other words, while the first indicator is fixed at a preset position in the display area, the ultrasound image displayed in the display area may be moved. In this case, as the ultrasound image is moved, the position at which the first indicator overlaps on the ultrasound image may be changed.

In an embodiment, the ultrasound imaging device 40 may display the ultrasound image indicating a zoomed-in area around the first indicator overlapped on the ultrasound image. In an embodiment, before the ultrasound imaging device 40 displays the first indicator to overlap on the ultrasound image in operation S320, the ultrasound imaging device 40 may determine the position at which the first indicator overlaps on the ultrasound image, and may display the first indicator with the ultrasound image indicating a zoomed-in area around the determined position.

In an embodiment, in operation S320, the ultrasound imaging device 40 may display the first indicator to overlap on the ultrasound image, and may display the ultrasound image indicating a zoomed-in area around the first indicator overlapped on the ultrasound image, in response to a user input of zooming in the ultrasound image. Here, for convenience of descriptions of the disclosure, an ultrasound image indicating a zoomed-in area of the ultrasound image may be referred to as a zoomed-in ultrasound image. In an embodiment, the ultrasound imaging device 40 may display the first indicator to overlap on the zoomed-in ultrasound image.

In an embodiment, a touch input of zooming in an ultrasound image from among the touch input for an ultrasound image may include a touch input of zooming in an ultrasound image displayed in the display area. For example, the touch input may include a pinch zoom input of zooming in an ultrasound image, but the disclosure is not limited thereto. In an embodiment, the ultrasound imaging device 40 may zoom in an ultrasound image, based on a user input obtained via the input interface 170.

In an embodiment, the ultrasound imaging device 40 may determine a zoomed-in area around the first indicator overlapped on an ultrasound image, based on the touch input of zooming in the ultrasound image. In an embodiment, a ratio by which an area around the first indicator overlapped on the ultrasound image is zoomed-in may be preset or may be determined based on a level of the touch input of zooming in the ultrasound image. In an embodiment, when the zoomed-in area is determined, the ultrasound imaging device 40 may display, in the display area, an ultrasound image indicating the determined zoomed-in area. In an embodiment, the ultrasound imaging device 40 may display the first indicator to overlap on the zoomed-in area around, at the position at which the first indicator overlaps on the ultrasound image before zooming in.

In an embodiment, the ultrasound imaging device 40 may display the ultrasound image indicating an area around the indicator overlapped on the ultrasound image, the area being zoomed in by read zoom or write zoom.

The read zoom may be referred to as digital zoom, and may indicate that the ultrasound image of which area is magnified by zooming in the displayed ultrasound image is displayed. In other words, when the ultrasound imaging device 40 zooms in an ultrasound image by read zoom, the ultrasound imaging device 40 does not obtain a new ultrasound image so as to display a zoomed-in ultrasound image, and may display the zoomed-in ultrasound image, by zooming in an area of the ultrasound image that is previously displayed.

The write zoom may be referred to as optical zoom, and may indicate that a zoomed-in ultrasound image is obtained, instead of a pre-displayed ultrasound image, and the obtained zoomed-in ultrasound image is displayed. Accordingly, the ultrasound imaging device 40 may adjust an ultrasound parameter, based on information about a zoomed-in area around the indicator overlapped on an ultrasound image, may obtain a new ultrasound image, based on the adjusted ultrasound parameter, and thus, may display a zoomed-in ultrasound image in the display area.

In an embodiment, in order to perform write zoom, the ultrasound imaging device 40 configured to display a real-time ultrasound image may provide information of an adjusted parameter to the probe 20, and may obtain a new ultrasound image from the probe 20. In an embodiment, in order to perform write zoom, the ultrasound imaging device 40 configured to display a pre-stored ultrasound image may generate a new ultrasound image, based on the adjusted parameter and ultrasound image raw data.

In operation S340, the ultrasound imaging device 40 may determine a position of the first indicator to be a first position, in response to a first position determination input of determining the position of the first indicator so as to place the first indicator at the first position on the ultrasound image.

In an embodiment, the first position determination input may include a user input of determining a position of the indicator. For example, the ultrasound imaging device 40 may display a UI for determining the position of the indicator on the touch screen 141, and may obtain a touch input of selecting the displayed UI as the user input of determining the position of the indicator, but the disclosure is not limited thereto. In an embodiment, the ultrasound imaging device 40 may obtain, as the first position determination input, a user input obtained via the input interface 170.

In an embodiment, the first position determination input may include an output of an AI model configured to determine a position of an indicator. In an embodiment, the ultrasound imaging device 40 may apply the first indicator and an ultrasound image displayed on the touch screen 141 to the AI model, thereby obtaining the first position determination input. In an embodiment, the AI model may include a model trained to output the first position determination input by receiving an input of the first indicator and the ultrasound image displayed on the touch screen 141. In an embodiment, the ultrasound imaging device 40 may obtain a first position determination input from the AI model, based on the first indicator and an ultrasound image displayed on the touch screen 141 as a display area of the ultrasound image is moved, and may determine a position of the first indicator to be a first position on the ultrasound image.

In an embodiment, when the first position determination input is obtained, the ultrasound imaging device 40 may identify a position at which the first indicator overlaps on the ultrasound image in a time point of obtaining the first position determination input, and may determine the position of the first indicator to be the identified position.

In an embodiment, when the position of the first indicator is determined to be the first position on the ultrasound image, the ultrasound imaging device 40 may place the first indicator at the first position on the ultrasound image. In an embodiment, that an indicator is placed may mean that the indicator is fixed at a determined position and is displayed with an ultrasound image. In other words, before the first indicator is placed at the first position on the ultrasound image, when the ultrasound image is moved, a position at which the first indicator is fixed in the display area and overlaps on the ultrasound image may be changed. On the other hand, after the first indicator is placed at the first position on the ultrasound image, even when the ultrasound image is moved, the first indicator is fixed at the first position on the ultrasound image and thus a position at which the first indicator overlaps on the ultrasound image may not be changed. Accordingly, the first indicator placed at the first position on the ultrasound image may be fixed at the first position and be moved together with the ultrasound image.

In an embodiment, before a position of an indicator is determined, the indicator placed on an ultrasound image may have a different color or a different shape from an indicator fixed and displayed in a display area. For example, an indicator displayed with a yellow color may turn to a red color after the indicator is placed and overlaps on an ultrasound image. However, the disclosure is not limited thereto, and the indicator to be placed on the ultrasound image may be changed in its color and shape or in only a color after it is placed on the ultrasound image.

In operation S350, the ultrasound imaging device 40 may move the ultrasound image, in response to a second touch input of moving the ultrasound image in the display area while the position of the first indicator is determined to be the first position. In an embodiment, the second touch input and movement of the ultrasound image may correspond to the first touch input and movement of the ultrasound image described in operation S330, and thus, redundant descriptions are not provided here.

In an embodiment, the ultrasound imaging device 40 may display a second indicator to overlap on the ultrasound image. In an embodiment, when the position of the first indicator is determined to be the first position on the ultrasound image, the ultrasound imaging device 40 may display the second indicator to overlap on the ultrasound image.

In an embodiment, a method by which the ultrasound imaging device 40 displays the second indicator to overlap on an ultrasound image may correspond to a method by which the ultrasound imaging device 40 displays the first indicator to overlap on an ultrasound image described in operation S320, and thus, redundant descriptions are not provided here. In an embodiment, the second indicator may have the same shape and/or the same color as the first indicator, and a method by which the ultrasound imaging device 40 determines a position at which the second indicator overlaps on an ultrasound image may correspond to a method by which the ultrasound imaging device 40 determines a position at which the first indicator overlaps on an ultrasound image described in operation S320, and thus, redundant descriptions are not provided here.

In an embodiment, when the position of the first indicator is determined to be the first position on the ultrasound image, the ultrasound imaging device 40 may display an ultrasound image indicating a zoomed-in area around the second indicator overlapped on the ultrasound image. In an embodiment, a zoom ratio of the ultrasound image which indicates the zoomed-in area around the second indicator overlapped on the ultrasound image may be equal to a zoom ratio of the ultrasound image which indicates the zoomed-in area around the first indicator overlapped on the ultrasound image.

In an embodiment, the ultrasound imaging device 40 may move the ultrasound image, in response to a second touch input of moving the ultrasound image while a position of the second indicator is fixed in the display area. In an embodiment, an operation of the ultrasound imaging device 40 for moving the ultrasound image while the position of the second indicator is fixed in the display area may correspond to an operation of the ultrasound imaging device 40 for moving the ultrasound image while the position of the first indicator is fixed in the display area, and thus, redundant descriptions are not provided here.

In an embodiment, the ultrasound imaging device 40 may determine the position of the second indicator to be a second position, in response to a second position determination input of determining the position of the second indicator so as to place the second indicator at the second position on the ultrasound image. An operation of the ultrasound imaging device 40 for determining the position of the second indicator to be the second position on the ultrasound image may correspond to an operation of determining the position of the first indicator to be the first position, and thus, redundant descriptions are not provided here.

In an embodiment, when the position of the second indicator is determined to be the second position on the ultrasound image, the ultrasound imaging device 40 may place the second indicator at the second position on the ultrasound image. In other words, before the second indicator is placed at the second position on the ultrasound image, when the ultrasound image is moved, a position at which the second indicator is fixed in the display area and overlaps on the ultrasound image may be changed. On the other hand, after the second indicator is placed at the second position on the ultrasound image, even when the display area of the ultrasound image is moved, the second indicator is fixed at the second position on the ultrasound image and thus a position at which the second indicator overlaps on the ultrasound image may not be changed. Accordingly, the second indicator placed at the second position on the ultrasound image may be fixed at the second position and be moved together with the ultrasound image.

In an embodiment, after the first indicator is placed at the first position on the ultrasound image, the ultrasound imaging device 40 may move the ultrasound image while the position of the second indicator is fixed in the display area.

In an embodiment, the ultrasound imaging device 40 may fix the first indicator at the first position and may move the first indicator together with the ultrasound image. That is, when the ultrasound image is moved, the first indicator is fixed at the first position on the ultrasound image and is moved together with the ultrasound image, but the second indicator of which position is not determined may be fixed and displayed in the display area.

In an embodiment, when the first position is not included in an ultrasound image displayed in the display area as the display area of the ultrasound image is moved, the first indicator may not be displayed in the display area and only the second indicator may be fixed at a position in the display area and be displayed. In this case, even when the first indicator is not displayed in the display area, the first indicator may be continuously fixed at the first position on the ultrasound image. Afterward, when the first position is included in the ultrasound image displayed in the display area as the ultrasound image is moved, the first indicator may be fixed at the first position on the ultrasound image and be displayed in the display area. In an embodiment, an ultrasound imaging device may display a plurality of indicators including a first indicator and a second indicator to overlap on an ultrasound image, and may determine respective positions of the plurality of indicators. Descriptions thereof will be provided below with reference to FIG. 9.

In an embodiment, the ultrasound imaging device 40 may display a line to overlap on an ultrasound image, the line connecting between the first indicator and the second indicator. In an embodiment, the line that connects between the first indicator and the second indicator may be a straight line that connects between the first indicator and the second indicator with a shortest length or may be a curved line with a preset shape, but the disclosure is not limited thereto.

In an embodiment, a shape of the line that connects between the first indicator and the second indicator may be formed to correspond to present measurement with respect to the ultrasound image. For example, when a measurement mode of measuring a length is selected, the ultrasound imaging device 40 may display a line that connects between the first indicator and the second indicator with a shortest length, and when a measurement mode of measuring an area is selected, the ultrasound imaging device 40 may display a curved line that connects between the first indicator and the second indicator, but the disclosure is not limited thereto.

In an embodiment, after the first indicator is placed at the first position, when the ultrasound image is moved while the position of the second indicator is fixed in the display area, the line that connects between the first indicator and the second indicator may be adjusted based on the position of the first indicator and the position of the second indicator. For example, as the display area of the ultrasound image is moved, a position of the first indicator fixed at the first position on the ultrasound image and a position of the second indicator fixed in the display area, the positions being relative to each other, may be changed. Accordingly, at least one of a length of the line connecting between the first indicator and the second indicator, a shape of the line, or an angle with respect to a preset axis of the ultrasound image may be changed in response to movement of the ultrasound image.

In an embodiment, the ultrasound imaging device 40 may perform preset measurement on an ultrasound image, based on a position of an indicator placed on the ultrasound image. In an embodiment, the ultrasound imaging device 40 may identify the position of the indicator on the ultrasound image, and may obtain anatomical information or lesion information which is related to the identified position. In an embodiment, the ultrasound imaging device 40 may identify positions of at least two indicators placed on an ultrasound image, and may obtain, based on the identified positions, at least one of a length, an area, or an angle, which is of the object 10 in the ultrasound image.

In an embodiment, the indicator may include an indicator configured to determine at least one of a position of a scan line of a Doppler image included in the ultrasound image or a position of a sample volume gate of the Doppler image. The Doppler image may indicate that information of a direction and velocity of a blood flow of the object 10 is obtained based on the Doppler effect due to movement of ultrasound wavelength, and the obtained information is displayed in a visual form on an ultrasound image.

In an embodiment, the ultrasound imaging device 40 may display a third indicator to overlap on the ultrasound image, the third indicator being configured to determine an angle of the sample volume gate according to a stream line corresponding to a blood flow of an object in the Doppler image.

In an embodiment, the ultrasound imaging device 40 may rotate the third indicator, while the ultrasound image is fixed, in response to a third touch input of changing the angle of the sample volume gate.

In an embodiment, the ultrasound imaging device 40 may obtain a Doppler image, based on a position of an indicator configured to determine at least one of a position of a scan line of the Doppler image in an ultrasound image or a position of a sample volume gate of the Doppler image. Detailed descriptions thereof will be provided below with reference to FIGS. 12 to 14.

In an embodiment, the ultrasound imaging device 40 may display a zoomed-in area around the position of the indicator placed on the ultrasound image as a display area of the ultrasound image, and may display a result of preset measurement obtained based on the position of the indicator placed on the ultrasound image.

In an embodiment, the second touch input of moving the ultrasound image may include a user input of performing preset measurement, based on the position of the first indicator on the ultrasound image. In an embodiment, when the ultrasound imaging device 40 obtains the second touch input, the ultrasound imaging device 40 may move the ultrasound image, and thus, may display an ultrasound image indicating a zoomed-in area around the position of the first indicator and may display an obtained result of the preset measurement.

In an embodiment, when the preset measurement is performed based on positions of a plurality of indicators on an ultrasound image, the ultrasound imaging device 40 may move the ultrasound image, and thus, may display an ultrasound image indicating an area including all of the positions of the plurality of indicators on the ultrasound image, and may display an obtained result of the preset measurement.

Figure 4A:
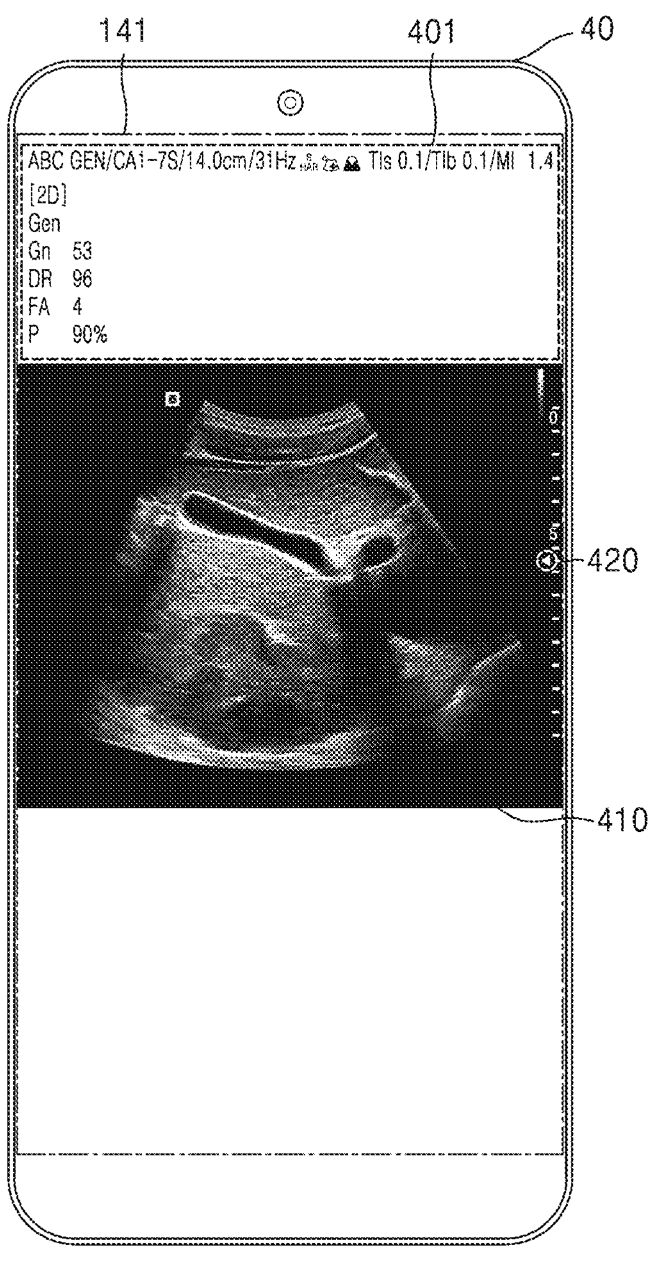
FIGS. 4A and 4B are diagrams for describing that an ultrasound imaging device according to an embodiment displays an ultrasound image and an indicator.
Figure 4B:
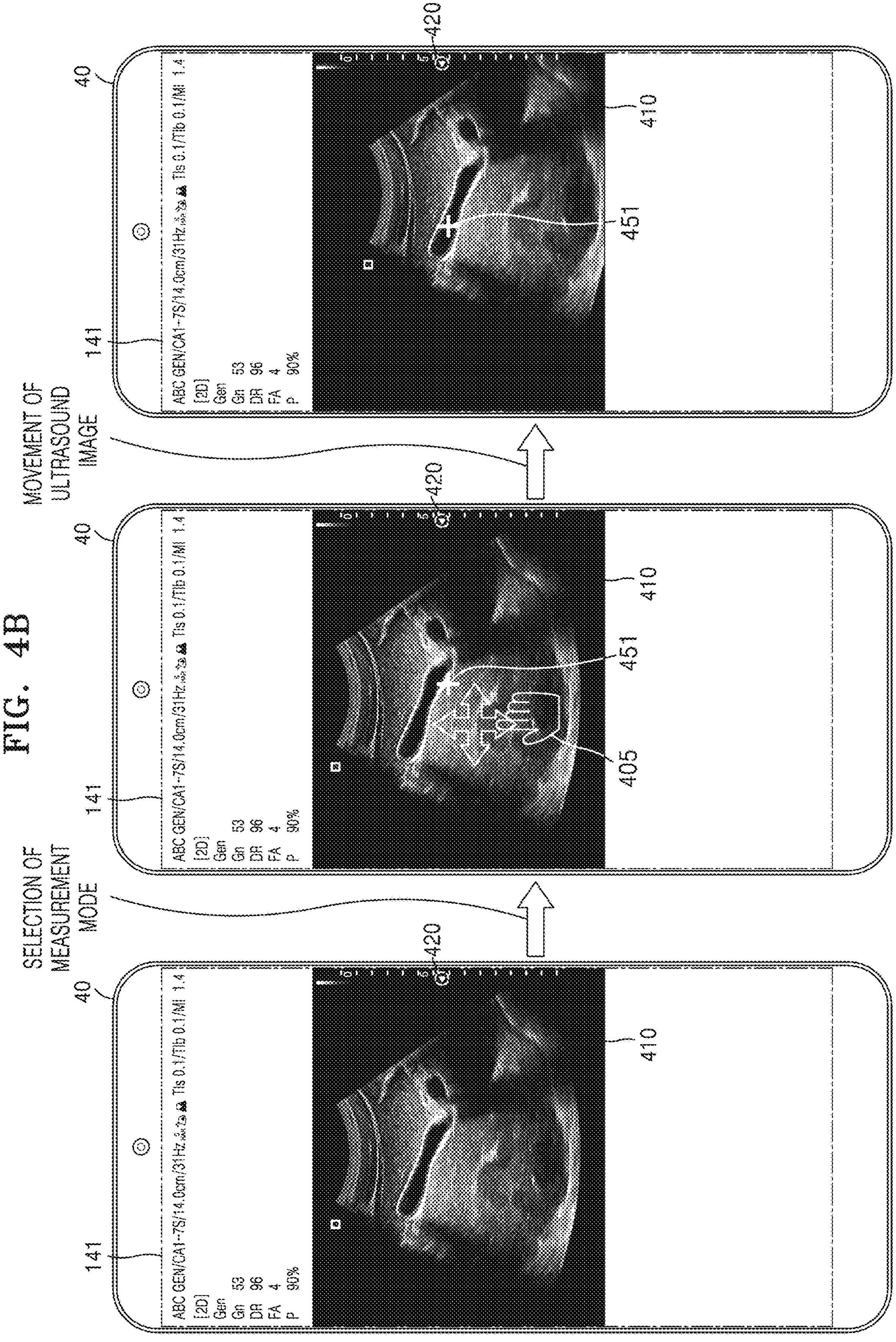

FIGS. 4A and 4B are diagrams for describing that the ultrasound imaging device 40 according to an embodiment displays an ultrasound image and an indicator.

Referring to FIG. 4A, the ultrasound imaging device 40 may display an ultrasound image in a display area 410 of the touch screen 141. In an embodiment, the ultrasound imaging device 40 may display all of a text UI 401, a focal point indicator 420, and the ultrasound image on the touch screen 141.

The text UI 401 may be displayed in the form of a text of information related to the ultrasound image. For example, the text UI 401 may include at least one of patient information, information of a type and protocol of a checkup, information of ultrasound parameters, information of a measurement result, or information of a date and time, but the disclosure is not limited thereto.

The focal point indicator 420 may include information indicating at which point of the ultrasound image displayed in the display area 410 a position of a focal point is. The focal point may indicate a point to which a signal transmitted from the probe 20 is focused in the object 10. An area around the position of the focal point in the object 10 may have an increased resolution and an increased contrast, compared to other areas on the ultrasound image, and thus, a structure of the object 10 may be further clearly displayed.

In an embodiment, the ultrasound imaging device 40 may adjust the position of the focal point. When the position of the focal point is adjusted, the ultrasound imaging device 40 may obtain, by controlling the ultrasound transceiving module 110, an ultrasound image corresponding to the adjusted position of the focal point, and may display the ultrasound image in the display area 410.

In an embodiment, when an ultrasound image includes a real-time ultrasound image, and a position of the focal point is adjusted, the ultrasound imaging device 40 may transmit, by controlling the ultrasound transceiving module 110, information of the adjusted position of the focal point on the ultrasound image to the probe 20. The probe 20 may adjust a signal transmitted from the probe 20 to be focused on a point of the object 10 which corresponds to the adjusted position of the focal point, based on the received information, and may generate an ultrasound image, based on a signal adjusted based on a signal reflected from the object 10. The probe 20 may transmit the ultrasound image generated based on the adjusted signal to the ultrasound imaging device 40, and the ultrasound imaging device 40 may display, in the display area 410, the ultrasound image received from the probe 20.

In an embodiment, when an ultrasound image includes a pre-stored ultrasound image generated from ultrasound image raw data, the ultrasound imaging device 40 may generate, upon adjustment of the position of the focal point, an ultrasound image based on the adjusted point of the focal point from the ultrasound image raw data, by controlling the reception module 115. The ultrasound imaging device 40 may display, in the display area 410, the generated ultrasound image based on the adjusted point of the focal point.

In an embodiment, the ultrasound imaging device 40 may display the position of the focal point indicator 420 to correspond to a position of a focal point on an ultrasound image. In an embodiment, the focal point indicator 420 may include information indicating in which depth of an ultrasound image the position of the focal point is, by being displayed with an indicator indicating information of a depth of the ultrasound image, on the touch screen 141. In an embodiment, the ultrasound imaging device 40 may configure a plurality of focal points, and may display a plurality of the focal point indicators 420 to respectively correspond to positions of the plurality of focal points on the ultrasound image.

Referring to FIG. 4B, the ultrasound imaging device 40 may display an ultrasound image in the display area 410 of the touch screen 141. The ultrasound image of FIG. 4B may correspond to an ultrasound image of FIG. 4A.

In an embodiment, the ultrasound imaging device 40 may obtain a user input of selecting a measurement mode. For example, the ultrasound imaging device 40 may obtain a user input of selecting a measurement mode for obtaining information of at least one of a length, an area, or an angle, which is related to an ultrasound image, but the disclosure is not limited thereto.

In an embodiment, when the ultrasound imaging device 40 obtains the user input of selecting a measurement mode, the ultrasound imaging device 40 may display a first indicator 451 to overlap on a displayed ultrasound image, the first indicator 451 corresponding to the selected measurement mode.

In an embodiment, the ultrasound imaging device 40 may display the first indicator 451 to overlap on the ultrasound image so as to allow the first indicator 451 to be placed at a position of a focal point on the current ultrasound image.

In an embodiment, the ultrasound imaging device 40 may adjust a position of a focal point on an ultrasound image to be a position of the first indicator 451 at which the first indicator 451 overlaps on a first ultrasound image, and may display the focal point indicator 420 to correspond to the adjusted position of the focal point.

In an embodiment, the ultrasound imaging device 40 may move, in response to a touch input 405 of moving an ultrasound image, the ultrasound image in the display area 410, while the position of the first indicator 451 is fixed in the display area 410. In an embodiment, the ultrasound imaging device 40 may display the moved ultrasound image and the first indicator 451 in the display area 410. In this case, as the ultrasound image is moved in the display area 410, an ultrasound image from which an area of an ultrasound image which is previously displayed is excluded and to which a new area is added may be displayed in the display area 410.

In an embodiment, the ultrasound imaging device 40 may adjust, based on an ultrasound image being moved, a position of a focal point on the ultrasound image to a position at which the first indicator 451 overlaps on the moved ultrasound image. In this case, the position of the focal point is adjusted as the ultrasound image is moved, but a position of the focal point indicator 420 may be constantly fixed as a position of the first indicator 451 is fixed in the display area 410.

Figure 5:
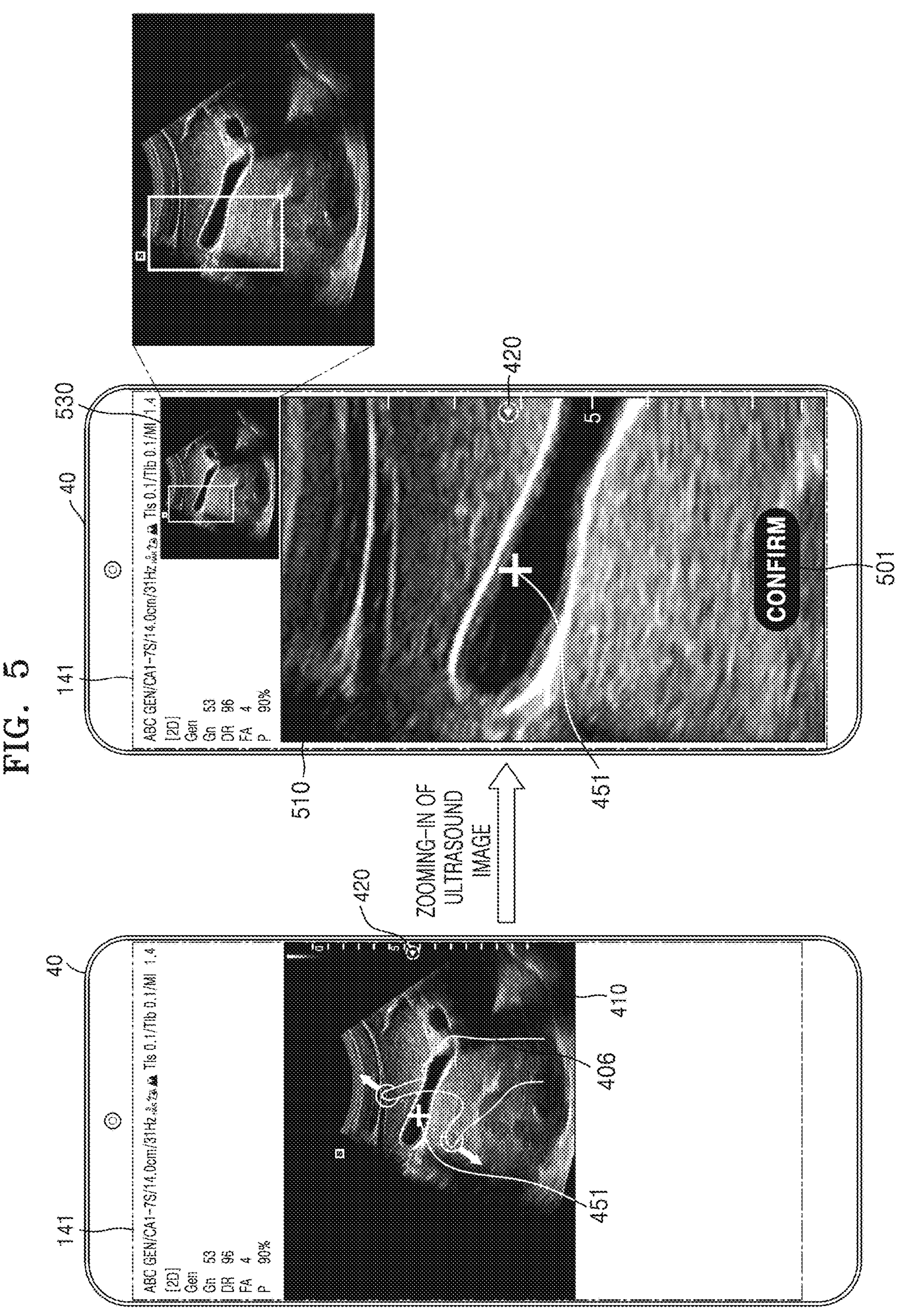
FIG. 5 is a diagram for describing that an ultrasound imaging device displays a zoomed-in ultrasound image and an indicator, according to an embodiment.

FIG. 5 is a diagram for describing that the ultrasound imaging device 40 displays a zoomed-in ultrasound image and an indicator, according to an embodiment. Referring to FIG. 5, the ultrasound imaging device 40 may display an ultrasound image and the first indicator 451 in the display area 410 of the touch screen 141.

In an embodiment, the ultrasound imaging device 40 may display, in a display area 510 of the touch screen 141, a zoomed-in ultrasound image indicating a zoomed-in area around the first indicator 451, in response to a user input of zooming in an ultrasound image. In an embodiment, the display area 510 in which the zoomed-in ultrasound image is displayed may have a size different from that of the display area 410 in which an ultrasound image that is not zoomed-in is displayed, but the disclosure is not limited thereto. In an embodiment, the ultrasound imaging device 40 may display a minimap UI 530, a position determination UI 501, and the zoomed-in ultrasound image on the touch screen 141.

The position determination UI 501 may indicate a UI for obtaining a user input of determining a position of the first indicator 451 displayed in the display area 510 so as to allow the first indicator 451 to be placed on an ultrasound image. In an embodiment, the ultrasound imaging device 40 may obtain a user input of selecting the position determination UI 501 as the user input of determining a position of the first indicator 451. However, the disclosure is not limited thereto, and the ultrasound imaging device 40 may obtain, via the input interface 170, a user input of determining a position of the first indicator 451.

In an embodiment, the ultrasound imaging device 40 may determine, in response to a user input of determining a position of the first indicator 451, the position of the first indicator 451 to be a first position at which the first indicator 451 overlaps on the zoomed-in ultrasound image displayed in the display area 510. In an embodiment, the position determination UI 501 may be displayed on the touch screen 141 of FIG. 4B, and when the ultrasound imaging device 40 obtains a user input of selecting the position determination UI 501 displayed on the touch screen 141, the ultrasound imaging device 40 may determine the position of the first indicator 451 to be a first position at which the first indicator 451 overlaps on an ultrasound image displayed in the display area 410.

The minimap UI 530 may mean a UI indicating a position of the zoomed-in ultrasound image which is from among an entire ultrasound image and is displayed in the display area 510. In an embodiment, when the zoomed-in ultrasound image is moved in the display area 510, the ultrasound imaging device 40 may display the minimap UI 530 on the touch screen 141 so as to indicate a position of the moved zoomed-in ultrasound image.

In an embodiment, the ultrasound imaging device 40 may display the first indicator 451 at a preset location of the display area 510. For example, the ultrasound imaging device 40 may display the first indicator 451 to be positioned at a very center of the touch screen 141 or a very center of the display area 510, but the disclosure is not limited thereto.

In an embodiment, the ultrasound imaging device 40 may adjust the position of the focal point to be a position at which the first indicator 451 overlaps on the zoomed-in ultrasound image displayed in the display area 510, and may display, on the touch screen 141, the focal point indicator 420 to correspond to the adjusted point of the focal point.

Figure 6A:
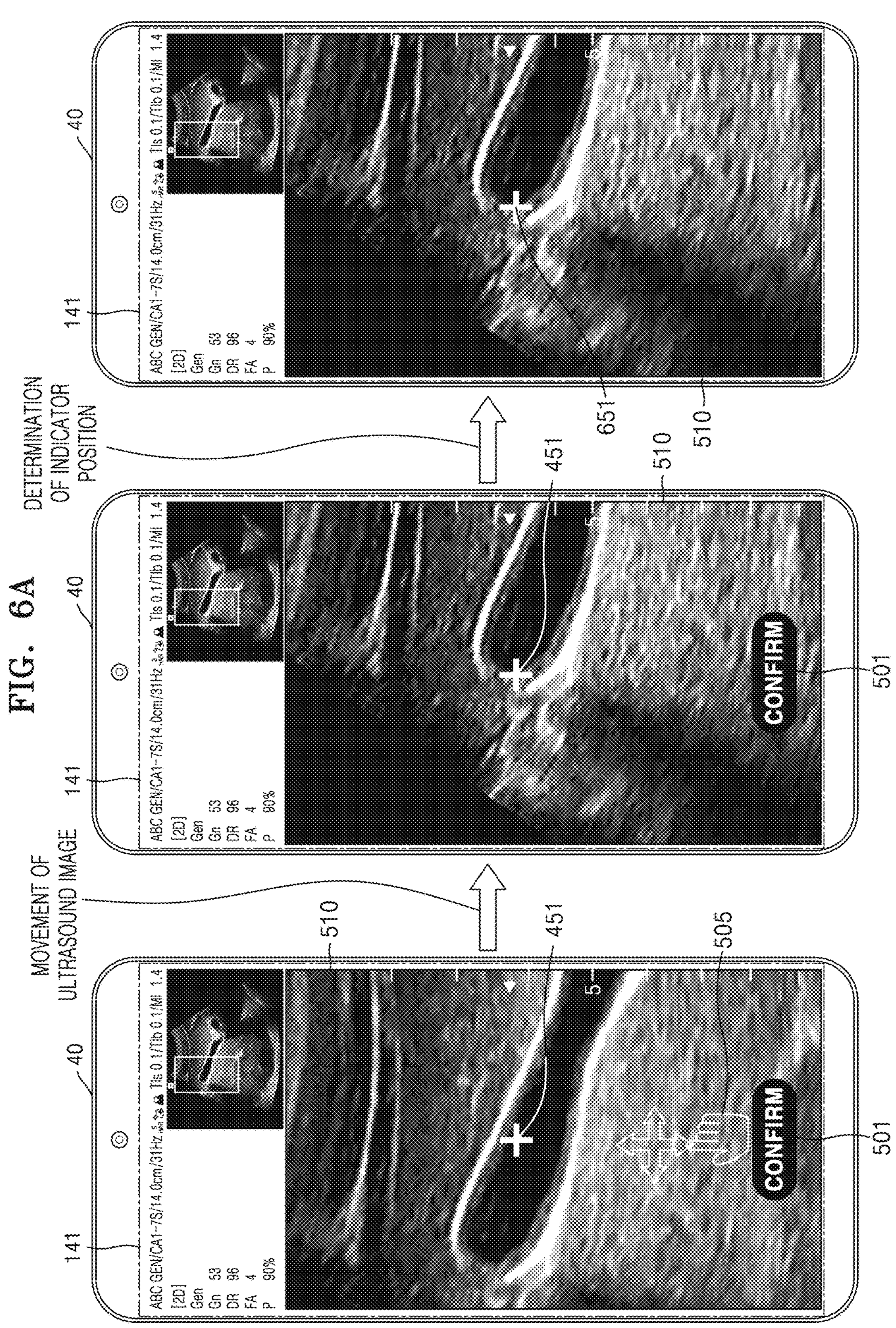
FIGS. 6A and 6B are diagrams for describing that an ultrasound imaging device determines a position of an indicator, according to an embodiment.
Figure 6B:
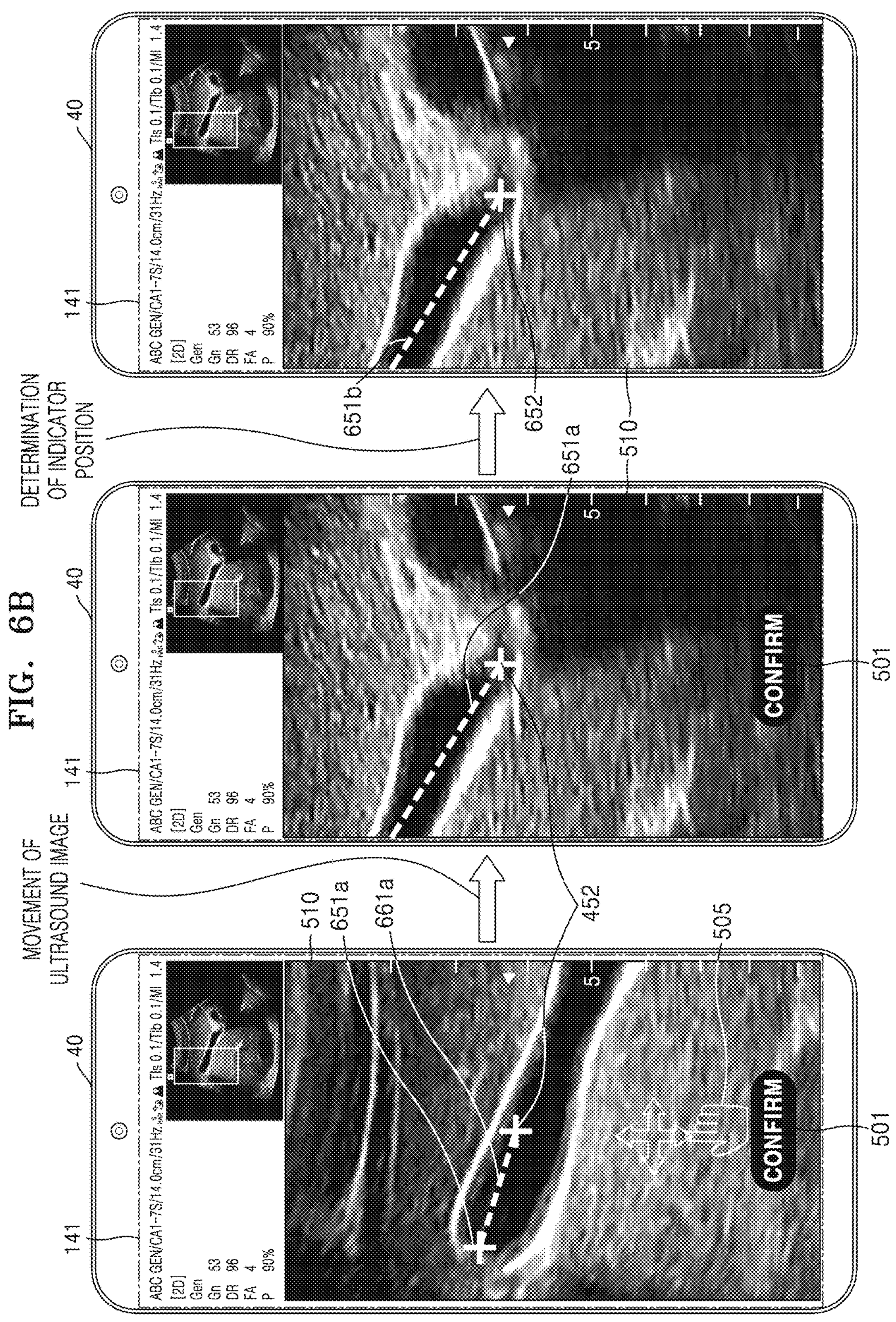

FIGS. 6A and 6B are diagrams for describing that the ultrasound imaging device 40 determines a position of an indicator, according to an embodiment.

Referring to FIG. 6A, the ultrasound imaging device 40 may display a zoomed-in ultrasound image and the first indicator 451 in the display area 510 of the touch screen 141.

In an embodiment, the ultrasound imaging device 40 may move the zoomed-in ultrasound image, in response to a first touch input 505 of moving the zoomed-in ultrasound image in the display area 510, while a position of the first indicator 451 is fixed in the display area 510. In an embodiment, as the zoomed-in ultrasound image is moved, the ultrasound imaging device 40 may display the moved zoomed-in ultrasound image and the first indicator 451 in the display area 510.

In an embodiment, when a user input of selecting the position determination UI 501 is obtained, the ultrasound imaging device 40 may determine a position of the first indicator 451 to be a first position at which the first indicator 451 overlaps on the moved zoomed-in ultrasound image. In an embodiment, when the position of the first indicator 451 is determined to the first position on the moved zoomed-in ultrasound image, the ultrasound imaging device 40 may place a first indicator 651 at the first position. In an embodiment, as the first indicator 651 placed at the first position has a different color or a different shape from the first indicator 451 that is fixed and displayed in the display area 510 before a position thereof is determined, a user may easily distinguish between the first indicator 651 of which position is determined and the first indicator 451 of which position is not determined. In this case, when the zoomed-in ultrasound image displayed in the display area 510 is moved, the first indicator 651 placed at the first position may be fixed at the first position and may be moved together with the zoomed-in ultrasound image. Accordingly, a position at which the first indicator 651 overlaps on an ultrasound image may not be moved.

Referring to FIG. 6B, the ultrasound imaging device 40 may display a zoomed-in ultrasound image and a second indicator 452 in the display area 510 of the touch screen 141. In an embodiment, the second indicator 452 may have the same shape and color as the first indicator 451.

In an embodiment, when a user input of adding a position of an indicator is obtained or a position of the first indicator 451 in FIG. 6A is determined to be a first position on an ultrasound image, the ultrasound imaging device 40 may display the moved zoomed-in ultrasound image and the second indicator 452 in the display area 510.

In an embodiment, the moved zoomed-in ultrasound image may be the zoomed-in ultrasound image displayed in the display area 510 of FIG. 5 or may be the ultrasound image indicating the zoomed-in area around a position at which the second indicator 452 overlaps on the zoomed-in ultrasound image.

In an embodiment, the ultrasound imaging device 40 may move the zoomed-in ultrasound image, in response to the first touch input 505 of moving the zoomed-in ultrasound image in the display area 510, while a position of the second indicator 452 is fixed in the display area 510. In an embodiment, as the zoomed-in ultrasound image is moved in the display area 510, the ultrasound imaging device 40 may display the moved zoomed-in ultrasound image and a third indicator 453 in the display area 510. In this case, when the zoomed-in ultrasound image is moved, the first indicator 651 placed at the first position is fixed at the first position and is moved together with the zoomed-in ultrasound image, but, the second indicator 452 of which position is not determined may be fixed and displayed in the display area 510.

In an embodiment, when a user input of selecting the position determination UI 501 is obtained, the ultrasound imaging device 40 may determine a position of the second indicator 452 to be a second position at which the second indicator 452 overlaps on the zoomed-in ultrasound image. In an embodiment, when the position of the second indicator 452 is determined to be the second position, the ultrasound imaging device 40 may place a second indicator 652 at the second position in the display area 410. In an embodiment, as the second indicator 652 placed at the second position has a different color or a different shape from the second indicator 452 that is fixed and displayed in the display area 510 before a position thereof is determined, a user may easily distinguish between the second indicator 652 of which position is determined and the second indicator 452 of which position is not determined.

In an embodiment, the ultrasound imaging device 40 may display a line 661 a to overlap on the zoomed-in ultrasound image, the line 661*a* connecting between the first indicator 651 placed at the first position and the second indicator 452. In an embodiment, based on the zoomed-in ultrasound image being moved in the display area 510, the line 661 a connecting between the first indicator 651 placed at the first position and the second indicator 452 may be changed in its length and position overlapping with the zoomed-in ultrasound image. For example, when the zoomed-in ultrasound image is moved in the display area 510, the first indicator 651 placed at the first position may be fixed at the first position and be moved together with the zoomed-in ultrasound image, and the second indicator 452 of which position is not determined may be fixed and displayed in the display area 510.

In other words, one end of the line 661*a* connecting between the first indicator 651 placed at the first position and the second indicator 452 may be fixed at the first position on the zoomed-in ultrasound image that has been moved, and the other end may be fixed in the display area 510. Accordingly, at least one of a length of the line 661*a* connecting between the first indicator 651 placed at the first position and the second indicator 452, a shape of the line 661*a*, or an angle with respect to a preset axis of an ultrasound image may be changed in response to the zoomed-in ultrasound image being moved in the display area 510.

In an embodiment, when the position of the second indicator 452 is determined to be a second position, the ultrasound imaging device 40 may display a line 661*b* to overlap on the zoomed-in ultrasound image, the line 661*b* connecting between the first indicator 651 placed at the first position and the second indicator 652 placed at the second position.

In an embodiment, even when the zoomed-in ultrasound image is moved in the display area 510, the line 661*b* connecting between the first indicator 651 placed at the first position and the second indicator 652 placed at the second position may be fixed at a disposed position on an ultrasound image and may be moved together with the ultrasound image. In other words, even when a display area of an ultrasound image is moved, the line 661*b* connecting between the first indicator 651 placed at the first position and the second indicator 652 placed at the second position may maintain its length and angle with respect to a horizontal axis or a vertical axis on the touch screen 141.

In this manner, the ultrasound imaging device 40 according to an embodiment may move an ultrasound image in a manner that the ultrasound imaging device 40 places and fixes an indicator of which position is determined at the determined position on the ultrasound image, and fixes an indicator of which position is not determined in the display area 510. In this case, as a line connecting between the indicator of which position is determined and the indicator of which position is not determined is changed in real time in its length, shape, angle, or the like due to a display area of an ultrasound image being moved, and is displayed to overlap on the ultrasound image, a user may easily and visually recognize information of a result of measurement performed by the user on the ultrasound image.

Figure 7A:
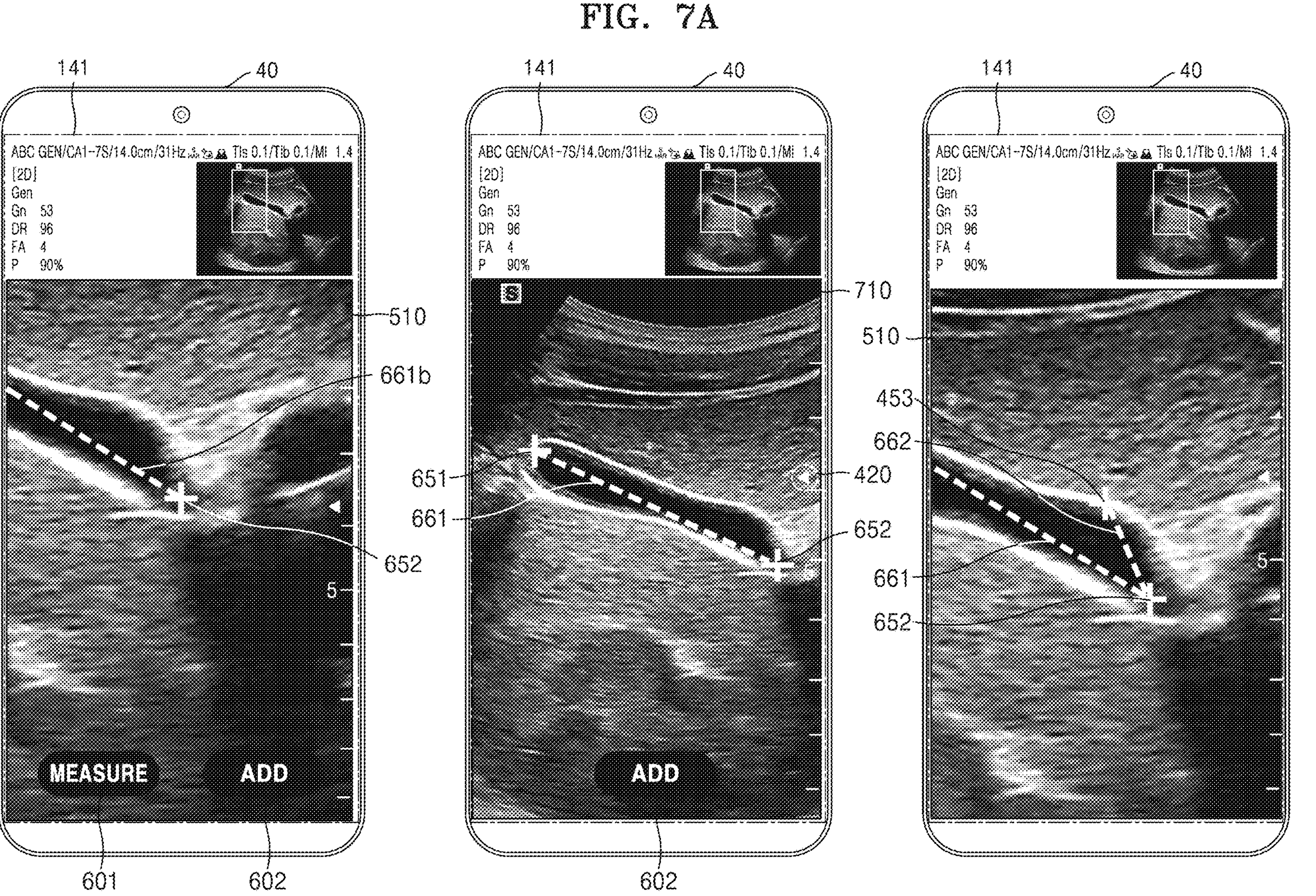
Figure 7B:
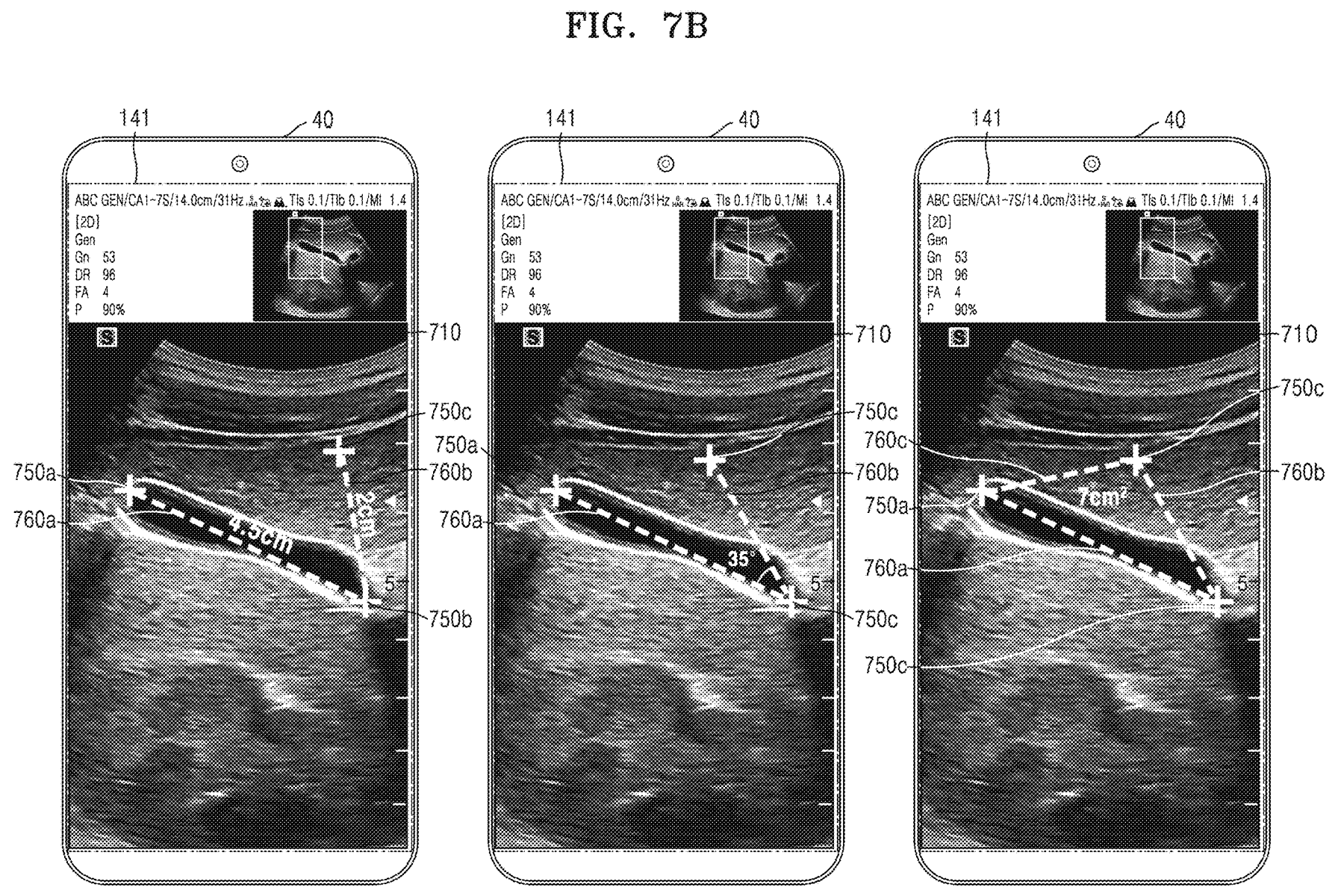

FIGS. 7A and 7B are diagrams for describing that the ultrasound imaging device 40 according to an embodiment performs preset measurement, based on a position of an indicator.

Referring to FIG. 7A, the ultrasound imaging device 40 may display a measurement execution UI 601 and an indicator addition UI 602 on the touch screen 141. While it is shown that the measurement execution UI 601 and the indicator addition UI 602 of FIG. 7A are displayed with the zoomed-in ultrasound image including the second indicator 652 placed at the second position of FIG. 6A, the disclosure is not limited thereto, and the measurement execution UI 601 and the indicator addition UI 602 may be displayed together with the zoomed-in ultrasound image including the first indicator 651 placed at the first position of FIG. 6A.

The measurement execution UI 601 may indicate a UI for obtaining a user input for performing preset measurement, based on a position of an indicator placed on an ultrasound image. In an embodiment, the ultrasound imaging device 40 may obtain a touch input of selecting the measurement execution UI 601, as the user input for performing preset measurement. However, the disclosure is not limited thereto, and the ultrasound imaging device 40 may obtain, via the input interface 170, the user input for performing preset measurement.

In an embodiment, when the ultrasound imaging device 40 obtains the user input for performing preset measurement, the ultrasound imaging device 40 may display a result of the preset measurement on the touch screen 141. In an embodiment, the ultrasound imaging device 40 may display a result output ultrasound image indicating a zoomed-in area around the indicator placed on the ultrasound image, in a display area 710 of the touch screen 141. In an embodiment, when the indicator for performing the preset measurement is plural in number, and positions of the plurality of indicators on the ultrasound image are all determined, the ultrasound imaging device 40 may display a result of the preset measurement on the touch screen 141. For example, as shown in FIG. 7A, the ultrasound imaging device 40 may display a result output ultrasound image including all of the first indicator 651 placed at the first position and the second indicator 652 placed at the second position, in the display area 710.

In an embodiment, the ultrasound imaging device 40 may adjust a position of a focal point to a position of an indicator placed on the result output ultrasound image, and may display the focal point indicator 420 to indicate the adjusted position of the focal point on the touch screen 141. In an embodiment, when the plurality of indicators are placed in the display area 710, the ultrasound imaging device 40 may adjust the position of the focal point to be a center among positions of the plurality of indicators placed on the result output ultrasound image, or may respectively adjust positions of a plurality of focal points to the positions of the plurality of indicators placed on the result output ultrasound image.

In an embodiment, the ultrasound imaging device 40 may display the result of the preset measurement to overlap on the result output ultrasound image. For example, the ultrasound imaging device 40 may display a line 661 and a text to overlap on the result output ultrasound image, the line 661 connecting between the first indicator 651 placed at the first position and the second indicator 652 placed at the second position, and the text indicating 4.5 cm as a length of the line 661.

The indicator addition UI 602 may indicate a UI for obtaining a user input of adding a position of an indicator. In an embodiment, the ultrasound imaging device 40 may obtain a touch input of selecting the indicator addition UI 602, as a user input of performing preset measurement. However, the disclosure is not limited thereto, and the ultrasound imaging device 40 may obtain the user input of performing preset measurement, via the input interface 170.

In an embodiment, the ultrasound imaging device 40 may display, in the display area 510 of the touch screen 141, a zoomed-in ultrasound image and a third indicator 453, in response to the user input of adding a position of an indicator. In an embodiment, the ultrasound imaging device 40 may display a line 662 to overlap on the zoomed-in ultrasound image, the line 662 connecting between the second indicator 652 at the second position and the third indicator 453. The method by which the ultrasound imaging device 40 moves a zoomed-in ultrasound image and determines a position of the third indicator 453 corresponds to a method of determining a position of the third indicator 453 of FIG. 6B, and thus, redundant descriptions are not provided here.

Referring to FIG. 7B, the ultrasound imaging device 40 may display a result output ultrasound image including a first indicator 750*a*, a second indicator 750*b*, and a third indicator 750*c* which are placed on an ultrasound image, in the display area 710 of the touch screen 141. In an embodiment, the ultrasound imaging device 40 may generate a line connected to different indicators placed on the ultrasound image, based on a first position of the first indicator 750*a*, a second position of the second indicator 750*b*, and a third position of the third indicator 750*c* which are placed on the result output ultrasound image. In an embodiment, the ultrasound imaging device 40 may obtain, as a result of the preset measurement, at least one of a length, an area, or an angle which is related to the display area 710, based on the line. In an embodiment, the result of the preset measurement may be displayed to overlap on the result output ultrasound image.

However, the disclosure is not limited thereto, and the result of the preset measurement may not be displayed to overlap on the result output ultrasound image but may be displayed in an area on the touch screen 141, not the display area 710.

In an embodiment, the ultrasound imaging device 40 may obtain information indicating that a length of a first line 760*a* connecting between the first indicator 750*a* and the second indicator 750*b* placed on the result output ultrasound image is 4.5 cm, and a length of a second line 760*b* connecting between the second indicator 750*b* and the third indicator 750*c* placed on the result output ultrasound image is 2 cm, and may display a text indicating the obtained information on the touch screen 141. However, the disclosure is not limited thereto, and although not illustrated, the ultrasound imaging device 40 may obtain information indicating that a length of a third line 760*c* connecting between the first indicator 750*a* and the third indicator 750*c* placed on the result output ultrasound image is 4 cm, and may display a text indicating the obtained information on the touch screen 141.

In an embodiment, the ultrasound imaging device 40 may obtain information indicating that an angle between the first line 760*a* and the second line 760*b* is 35°, and may display a text indicating the obtained information on the touch screen 141. However, the disclosure is not limited thereto, and although not illustrated, the ultrasound imaging device 40 may obtain information indicating that an angle between the second line 760*b* and the third line 760*c* is 115°, and an angle between the first line 760*a* and the third line 760*c* is 30°, and may display a text indicating the obtained information on the touch screen 141.

In an embodiment, the ultrasound imaging device 40 may obtain information indicating that an area of a triangle formed by the first line 760*a*, the second line 760*b*, and the third line 760*c* is 7 $cm^2$, and may display a text indicating the obtained information on the touch screen 141.

Figure 8:
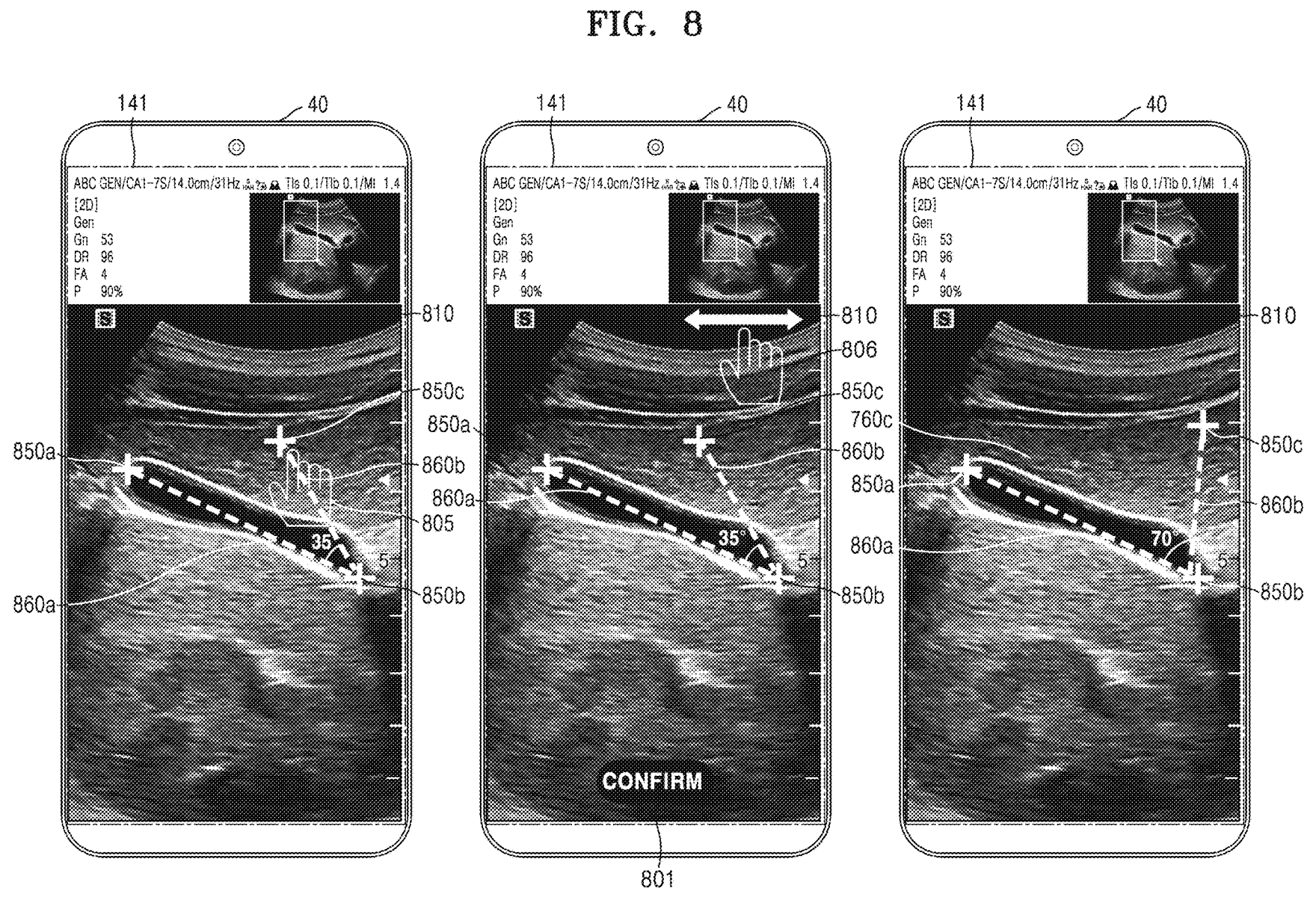

FIG. 8 is a diagram for describing that the ultrasound imaging device 40 adjusts an angle measurement line, according to an embodiment.

Referring to FIG. 8, the ultrasound imaging device 40 may display a first indicator 850*a* placed at a first position, a second indicator 850*b* placed at a second position, a reference line 860*a* which connect between the first indicator 850*a* and the second indicator 850*b*, and an angle measurement line 860*b* to overlap an ultrasound image displayed in a display area 810.

In an embodiment, the ultrasound image displayed in the display area 810 may include the result output ultrasound image displayed in the display area 710 of FIG. 7B. In this case, the reference line 860*a* and the angle measurement line 860*b* may correspond to the first line 760*a* and the second line 760*b* of FIG. 7B.

In an embodiment, the ultrasound image displayed in the display area 810 may be the result output ultrasound image displayed in the display area 710 of FIG. 7A to which the angle measurement line 860*b* is added. In this case, a line 661 connecting between the first indicator 651 and the second indicator 652 of FIG. 7A may correspond to the reference line 860*a*.

In an embodiment, the ultrasound imaging device 40 may obtain a user input for adjusting the angle measurement line 860*b*. For example, the user input for adjusting the angle measurement line 860*b* may include a touch input of selecting the angle measurement line 860*b* or a third indicator 850*c* which is displayed in the display area 810. However, the disclosure is not limited thereto, and the ultrasound imaging device 40 may obtain the user input for adjusting the angle measurement line 860*b*, via the input interface 170.

In an embodiment, when the ultrasound imaging device 40 obtains the user input for adjusting the angle measurement line 860*b*, until an angle between the reference line 860*a* and the angle measurement line 860*b* is determined, in other words, from a time when the user input for adjusting the angle measurement line 860*b* is obtained up to a time when the angle between the reference line 860*a* and the angle measurement line 860*b* is determined, the ultrasound imaging device 40 may obtain a touch input being input via the touch screen 141, as a touch input with respect to the angle measurement line 860*b*, not a touch input with respect to an ultrasound image.

In an embodiment, the ultrasound imaging device 40 may adjust the angle between the reference line 860*a* and the angle measurement line 860*b*, by moving a position at which the third indicator 850*c* overlaps on an ultrasound image displayed in the display area 810, based on an obtained touch input 806 with respect to the angle measurement line 860*b*. In this case, positions of the first indicator 850*a* and the second indicator 850*b* are not moved but are fixed on the ultrasound image, and only a position of the third indicator 850*c* is moved, such that the position at which the third indicator 850*c* overlaps on the ultrasound image displayed in the display area 810 may be moved.

In an embodiment, while the angle between the reference line 860*a* and the angle measurement line 860*b* is adjusted, the ultrasound imaging device 40 may determine the angle between the reference line 860*a* and the angle measurement line 860*b* to the adjusted angle, based on a user input of determining an angle. In an embodiment, the ultrasound imaging device 40 may display a measurement execution UI 801 on the touch screen 141, and may obtain a touch input of selecting the measurement execution UI 801 as the user input of determining an angle. In an embodiment, when the angle between the reference line 860*a* and the angle measurement line 860*b* is determined, the ultrasound imaging device 40 may display information of the determined angle on the touch screen 141. In an embodiment, after the angle between the reference line 860*a* and the angle measurement line 860*b* is determined, the ultrasound imaging device 40 may obtain, via the touch screen 141, a touch input with respect to the ultrasound image displayed in the display area 810.

Figure 9:
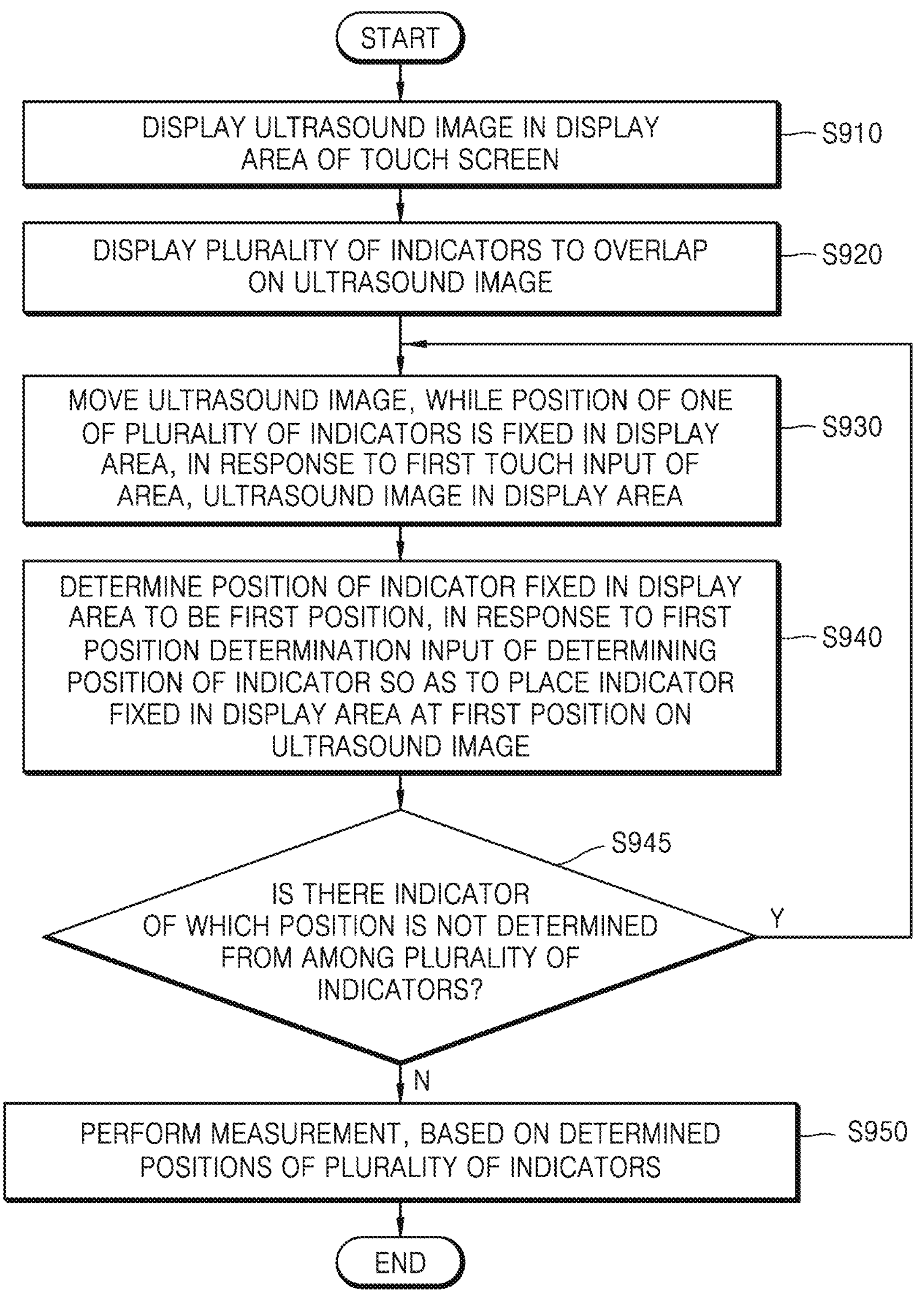
FIG. 9 is a flowchart for describing a control method of an ultrasound imaging device for displaying a plurality of indicators to overlap on an ultrasound image, according to an embodiment.

FIG. 9 is a flowchart for describing a control method of the ultrasound imaging device 40 for displaying a plurality of indicators to overlap on an ultrasound image, according to an embodiment. The control method of the ultrasound imaging device 40 to be described with reference to FIG. 9 may be substituted with the control method of the ultrasound imaging device 40 described with reference to FIGS. 1A and 1B and FIG. 3.

In operation S910, the ultrasound imaging device 40 may display an ultrasound image in a display area of the touch screen 141. Operation S910 may correspond to operation S310 of FIG. 3, and thus, redundant descriptions are not provided here.

In operation S920, the ultrasound imaging device 40 may display a plurality of indicators to overlap on the ultrasound image. In an embodiment, the ultrasound imaging device 40 may determine the number and placement of a plurality of indicators, based on preset measurement corresponding to a selected measurement mode, and may display the plurality of indicators according to the determined number and placement so as to overlap on the ultrasound image.

In an embodiment, the ultrasound imaging device 40 may determine positions at which the plurality of indicators overlap with the ultrasound image, by displaying the plurality of indicators at preset positions on the touch screen 141. For example, the ultrasound imaging device 40 may display a center of the plurality of indicators to be positioned at a very center on the touch screen 141 or at a very center of an ultrasound image displayed in a display area. However, the disclosure is not limited thereto, and the center of the plurality of indicators may be displayed at a random position on the touch screen 141.

In an embodiment, the ultrasound imaging device 40 may determine positions at which the plurality of indicators overlap with an ultrasound image, by applying the ultrasound image to an AI model. In an embodiment, the AI model may include a model trained to output, by receiving an input of at least one of an ultrasound image or a selected measurement mode, positions at which the plurality of indicators overlap with an ultrasound image. In an embodiment, the ultrasound imaging device 40 may display, on the touch screen 141, the plurality of indicators to overlap at the positions on the ultrasound image which are obtained from the AI model.

In operation S930, the ultrasound imaging device 40 may move the ultrasound image, while a position of one of the plurality of indicators is fixed in the display area, in response to a first touch input of moving the ultrasound image in the display area.

In an embodiment, the ultrasound imaging device 40 may select, from among the plurality of indicators, an indicator of which position is fixed in the display area. In an embodiment, the ultrasound imaging device 40 may determine, from among the plurality of indicators, the indicator of which position is fixed in the display area, based on a preset order, or may determine the indicator of which position is fixed in the display area, based on a user input of selecting one of the plurality of indicators. In operation S930, the indicator of which position is fixed in the display area from among the plurality of indicators may correspond to the first indicator described in operation S330 of FIG. 3, and thus, redundant descriptions are not provided here.

In an embodiment, based on the ultrasound image being moved in the display area, the ultrasound imaging device 40 may move a position at which an indicator of which position is not determined from among the plurality of indicators overlaps on the ultrasound image. In other words, the plurality of indicators that are displayed to overlap with the ultrasound image before positions thereof are not determined may have positions relative to other indicators, based on a preset placement scheme. In this case, when a position at which an indicator fixed in a display area overlaps an ultrasound image is changed based on the display area of the ultrasound image being moved, indicators of which positions are not determined may be moved together to maintain their positions relative to the indicator fixed in the display area, such that overlapping positions on the ultrasound image may be adjusted.

In operation S940, in response to a first position determination input of determining a position of an indicator so as to place the indicator fixed in the display area at a first position on the ultrasound image, the ultrasound imaging device 40 may determine the position of the indicator fixed in the display area to be the first position. In an embodiment, that an indicator is placed may mean that the indicator is fixed at a determined position and is displayed with an ultrasound image. In other words, before the indicator fixed in the display area is placed at the first position on the ultrasound image, when the ultrasound image is moved, the indicator may be fixed at the position in the display area, and thus, the position at which the indicator overlaps on the ultrasound image may be changed. On the other hand, after the indicator of which position is fixed in the display area is placed at the first position on the ultrasound image, even when the ultrasound image is moved, the indicator may be fixed at the first position, and thus, the position at which the indicator overlaps on the ultrasound image may not be changed. Accordingly, the indicator placed at the first position on the ultrasound image may be fixed at the first position and be moved together with the ultrasound image.

In operation S940, the indicator fixed in the display area from among the plurality of indicators may correspond to the first indicator described in operation S340 of FIG. 3, and thus, redundant descriptions are not provided here. In operation S945, the ultrasound imaging device 40 may identify whether there is an indicator of which position is not determined from among the plurality of indicators. Here, the indicator of which position is not determined may indicate an indicator that is not placed on the ultrasound image.

In an embodiment, when there is the indicator of which position is not determined from among the plurality of indicators (operation S945-Y), the ultrasound imaging device 40 may perform operations S930 and S940 on the indicator of which position is not determined. In an embodiment, when there are a plurality of indicators of which positions are not determined, the ultrasound imaging device 40 may determine an indicator to be fixed in the display area, from among the plurality of indicators of which positions are not determined.

In an embodiment, the ultrasound imaging device 40 may move the ultrasound image, while at least one indicator from among the plurality of indicators is placed on the ultrasound image and then a position of one of other indicators is fixed in the display area. In this case, when the display area of the ultrasound image is moved, a position of the at least one indicator placed on the ultrasound image is fixed and the at least one indicator is moved together with the ultrasound image, but a position of an indicator which is not determined and is fixed in the display area may be fixed and displayed in the display area.

In an embodiment, when there is no indicator of which position is not determined from among the plurality of indicators (operation S945-N), the ultrasound imaging device 40 may perform preset measurement, based on determined positions of the plurality of indicators (operation S950). A method by which the ultrasound imaging device 40 performs preset measurement, based on positions of the plurality of indicators is described above, and thus, redundant descriptions are not provided here.

FIGS. 10A to 10D are diagrams for describing that the ultrasound imaging device 40 measures a length with respect to an ultrasound image, according to an embodiment.

Figure 10A:
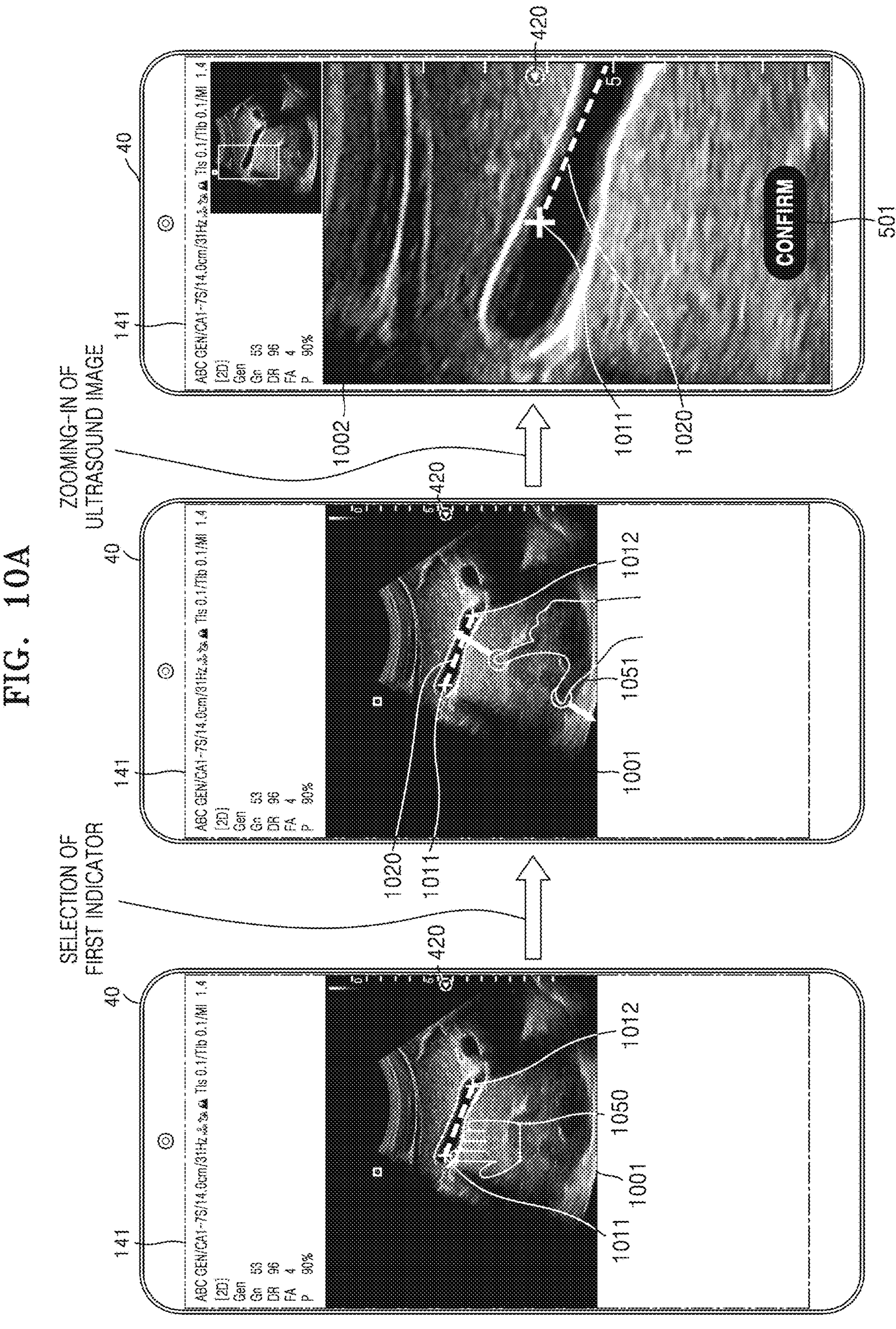
FIGS. 10A to 10D are diagrams for describing that an ultrasound imaging device measures a length with respect to an ultrasound image, according to an embodiment.

Referring to FIG. 10A, the ultrasound imaging device 40 may display an ultrasound image, and a first indicator 1011 and a second indicator 1012 which are overlapped on the ultrasound image, in a display area 1001 of the touch screen 141. In an embodiment, the ultrasound imaging device 40 may display a line 1020 to overlap on the ultrasound image, the line 1020 connecting between the first indicator 1011 and the second indicator 1012. In an embodiment, the ultrasound imaging device 40 may display the ultrasound image in the display area 1001 of the touch screen 141, and when a user input of selecting a measurement mode for measuring a length with respect to an ultrasound image is received, the ultrasound imaging device 40 may display the first indicator 1011 and the second indicator 1012 to overlap on the ultrasound image. In an embodiment, the ultrasound imaging device 40 may move the ultrasound image, while positions of the first indicator 1011 and the second indicator 1012 are fixed in the display area 1001, in response to a first touch input of moving the ultrasound image in the display area 1001.

In an embodiment, the ultrasound imaging device 40 may determine, from among the first indicator 1011 and the second indicator 1012, an indicator of which position is fixed in a display area 1002. For example, the ultrasound imaging device may determine the indicator of which position is fixed in the display area 1002 to be the first indicator 1011, based on a preset order or a user input 1050 of selecting the first indicator 1011, but the disclosure is not limited thereto.

In an embodiment, in response to a user input 1051 of zooming in the ultrasound image, the ultrasound imaging device 40 may display, in the display area 1002, the zoomed-in ultrasound image indicating a zoomed-in area around the first indicator 1011 fixed in the display area 1002. In an embodiment, when the zoomed-in ultrasound image is displayed in the display area 1002, the ultrasound imaging device 40 may display the first indicator 1011 to overlap the zoomed-in ultrasound image at a preset position on the touch screen 141.

In an embodiment, the ultrasound imaging device 40 may determine a position of a focal point to be a position at which the first indicator 1011 overlaps on the ultrasound image, may determine the position of the focal point to be a position at which the second indicator 1012 overlaps on the ultrasound image, or may determine the position of the focal point to be a center between the position at which the first indicator 1011 overlaps on the ultrasound image and the position at which the second indicator 1012 overlaps on the ultrasound image. In an embodiment, the ultrasound imaging device 40 may determine positions of two focal points to be respectively the position at which the first indicator 1011 overlaps on the ultrasound image and the position at which the second indicator 1012 overlaps on the ultrasound image. In an embodiment, the ultrasound imaging device 40 may display, on the touch screen 141, the focal point indicator 420 to correspond to the determined position of the focal point.

Figure 10B:
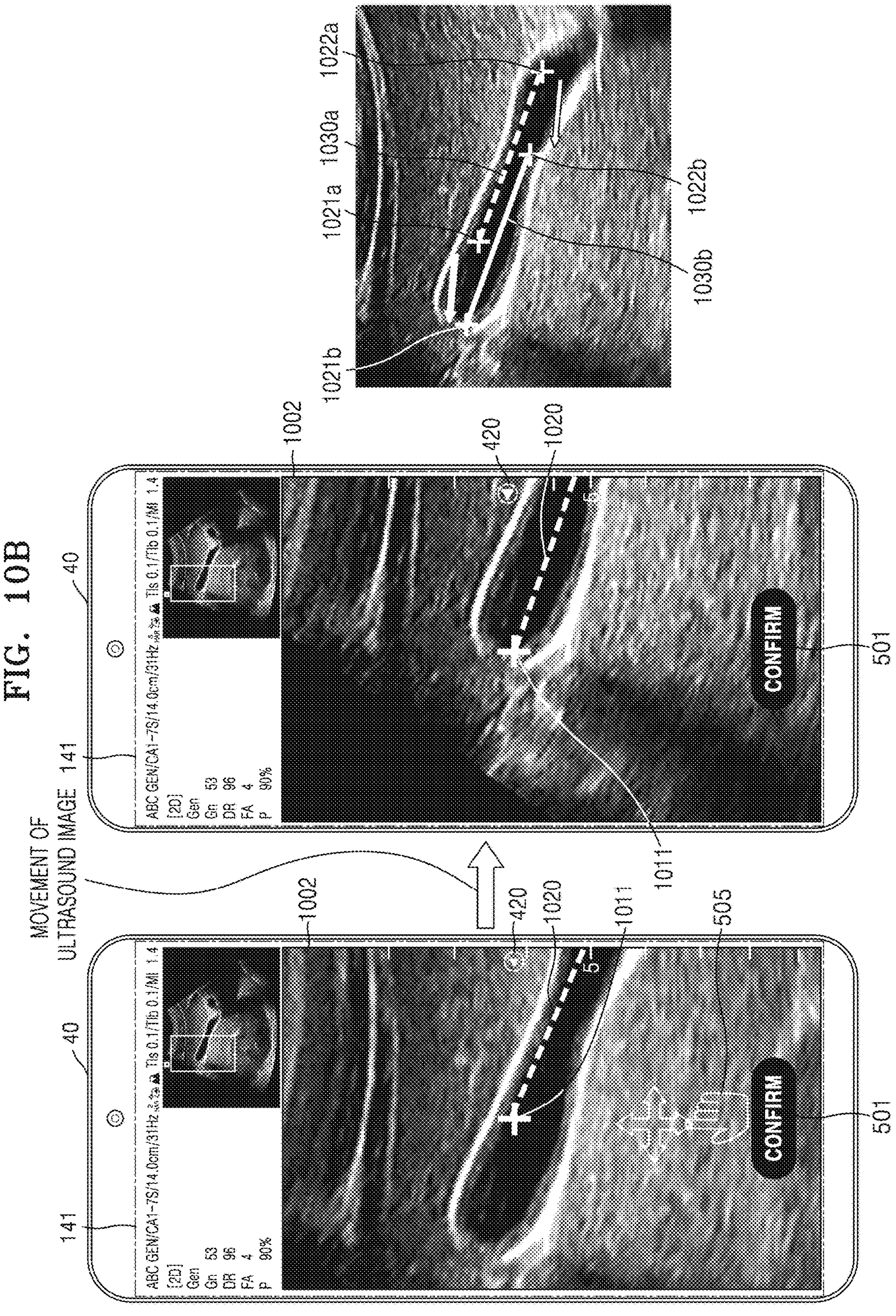

Referring to FIG. 10B, the ultrasound imaging device 40 may move the zoomed-in ultrasound image, in response to a first touch input 505 of moving the zoomed-in ultrasound image in the display area 1002, while the position of the first indicator 1011 is fixed in the display area 1002. In an embodiment, as the zoomed-in ultrasound image is moved, the ultrasound imaging device 40 may display the moved zoomed-in ultrasound image and the first indicator 1011 in the display area 1002.

In an embodiment, as the zoomed-in ultrasound image is moved while the position of the first indicator 1011 is fixed in the display area 1002, the ultrasound imaging device 40 may move the position at which the second indicator 1012 overlaps on the ultrasound image. In an embodiment, a position of the second indicator 1012 which is relative to the first indicator 1011 may be preset, and when the zoomed-in ultrasound image is moved while the position of the first indicator 1011 is fixed in the display area 1002, the ultrasound imaging device 40 may move the position at which the second indicator 1012 overlaps on the ultrasound image so as to maintain the position of the second indicator 1012 being relative to the first indicator 1011. In other words, when the zoomed-in ultrasound image displayed in the display area 1002 is moved to determine the position of the first indicator 1011, the position of the second indicator 1012 which is not yet determined may also be moved.

For example, as the zoomed-in ultrasound image displayed in the display area 1002 is moved, the position at which the first indicator 1011 overlaps on the ultrasound image may be moved from a first-overlapping position 1021*a* to a second-overlapping position 1021*b*. In this case, the ultrasound imaging device 40 may move the position at which the second indicator 1012 overlaps on the ultrasound image from a third-overlapping position 1022*a* to a fourth-overlapping position 1022*b*, based on the position of the second indicator 1012 being relative to the first indicator 1011. Also, as the position of the first indicator 1011 and the position of the second indicator 1012 are moved, the line 1020 connecting between the first indicator 1011 and the second indicator 1012 may be moved from a fifth-overlapping position 1030*a* to a sixth-overlapping position 1030*b*.

In an embodiment, when a user input of selecting the position determination UI 501 displayed on the touch screen 141 is obtained, the ultrasound imaging device 40 may determine a position of the first indicator 1011 to be a first position at which the first indicator 1011 overlaps on the zoomed-in ultrasound image displayed in the display area 1002, and may place the first indicator 1011 at the determined first position.

Figure 10C:
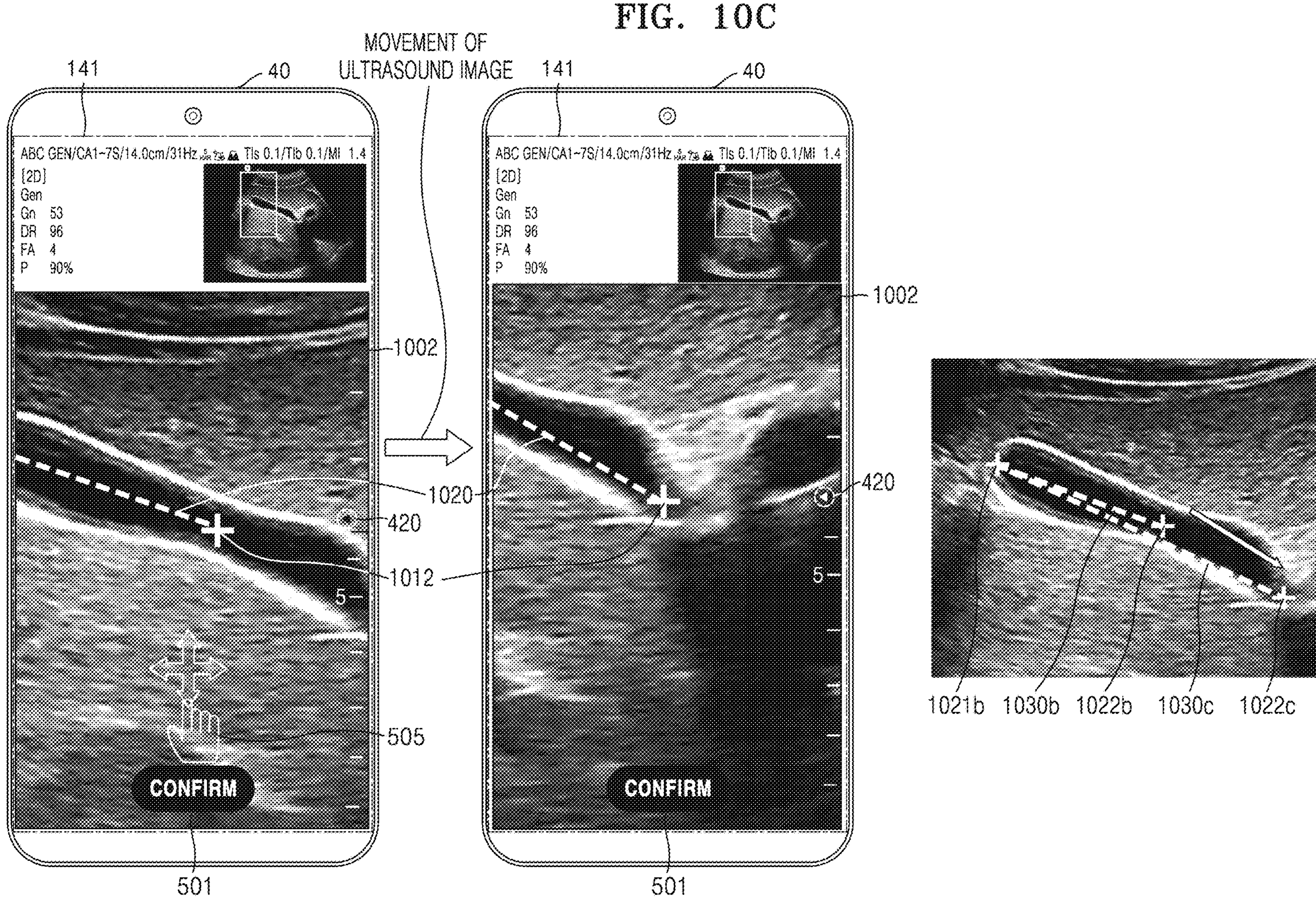

Referring to FIG. 10C, when the position of the first indicator 1011 is determined to be the first position on an ultrasound image, the ultrasound imaging device 40 may display, in the display area 1002, a zoomed-in ultrasound image indicating a zoomed-in area around the second indicator 1012 which overlaps on the ultrasound image, and the second indicator 1012.

In an embodiment, the ultrasound imaging device 40 may move the zoomed-in ultrasound image, in response to a first touch input 505 of moving the zoomed-in ultrasound image in the display area 1002, while the position of the first indicator 1011 is fixed in the display area 1002. In an embodiment, as the zoomed-in ultrasound image is moved, the ultrasound imaging device 40 may display the moved zoomed-in ultrasound image and the second indicator 1012 in the display area 1002.

In an embodiment, as the zoomed-in ultrasound image displayed in the display area 1002 is moved, the ultrasound imaging device 40 may fix, as the first position, a position at which the first indicator 1011 overlaps on the ultrasound image, and may move only a position at which the second indicator 1012 overlaps on the ultrasound image. In other words, when the zoomed-in ultrasound image is moved, the first indicator 1011 is fixed at a first position on an ultrasound image 1001 and thus is moved together with the ultrasound image 1001, but, the second indicator 1012 of which position is not determined may be fixed and displayed in the display area 1002, regardless of the ultrasound image.

For example, a position at which the first indicator 1011 overlaps on the ultrasound image may be fixed at the second-overlapping position 1021*b* and may not be moved. In this case, a position at which the second indicator 1012 overlaps on the ultrasound image may be moved from the fourth-overlapping position 1022*b* to a seventh-overlapping position 1022*c*. Also, as the position of the second indicator 1012 is moved, the line 1020 connecting between the first indicator 1011 and the second indicator 1012 may be moved from the sixth-overlapping position 1030*b* to an eighth-overlapping position 1030*c*.

In an embodiment, when a user input of selecting the position determination UI 501 is obtained, the ultrasound imaging device 40 may determine a position of the second indicator 1012 to be a second position at which the second indicator 1012 overlaps on the zoomed-in ultrasound image displayed in the display area 1002, and may place the second indicator 1012 at the determined second position.

Figure 10D:
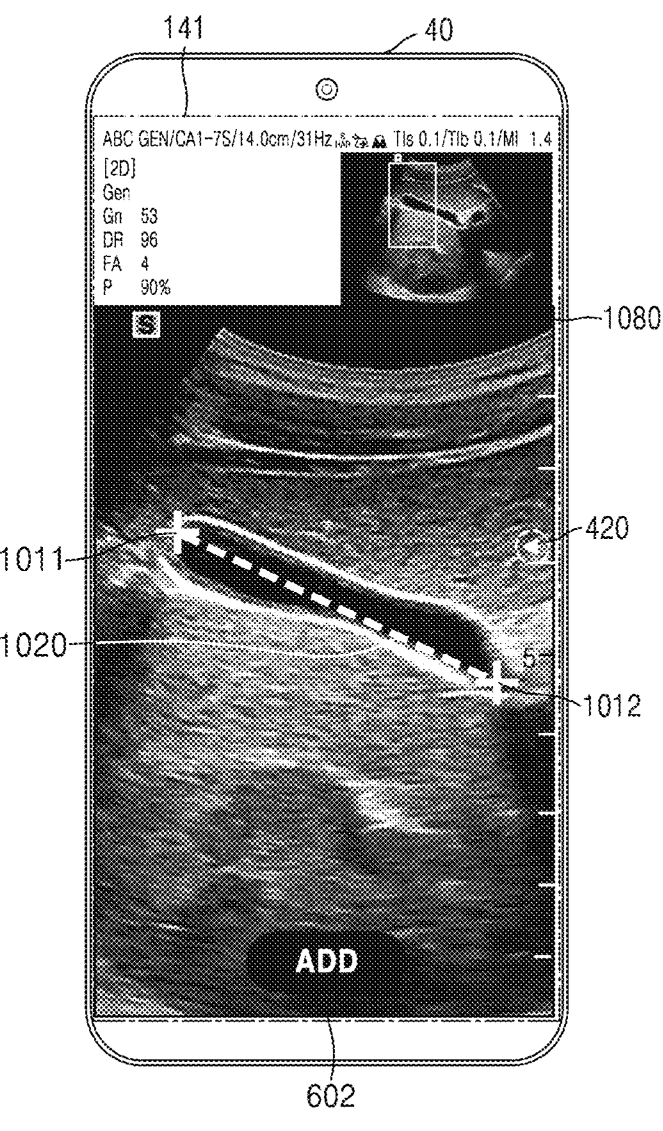

Referring to FIG. 10D, the ultrasound imaging device 40 may obtain, based on the first indicator 1011 placed at a first position and the second indicator 1012 at placed a second position on an ultrasound image, information indicating that a distance between the first indicator 1011 and the second indicator 1012 is 4.5 cm, as a result of preset measurement of a length measurement mode, and may display a text indicating the obtained result of the preset measurement, on the touch screen 141. In an embodiment, the ultrasound imaging device 40 may display, in a display area 1080, a result output ultrasound image indicating both the first indicator 1011 placed at the first position and the second indicator 1012 at placed the second position.

Figure 11A:
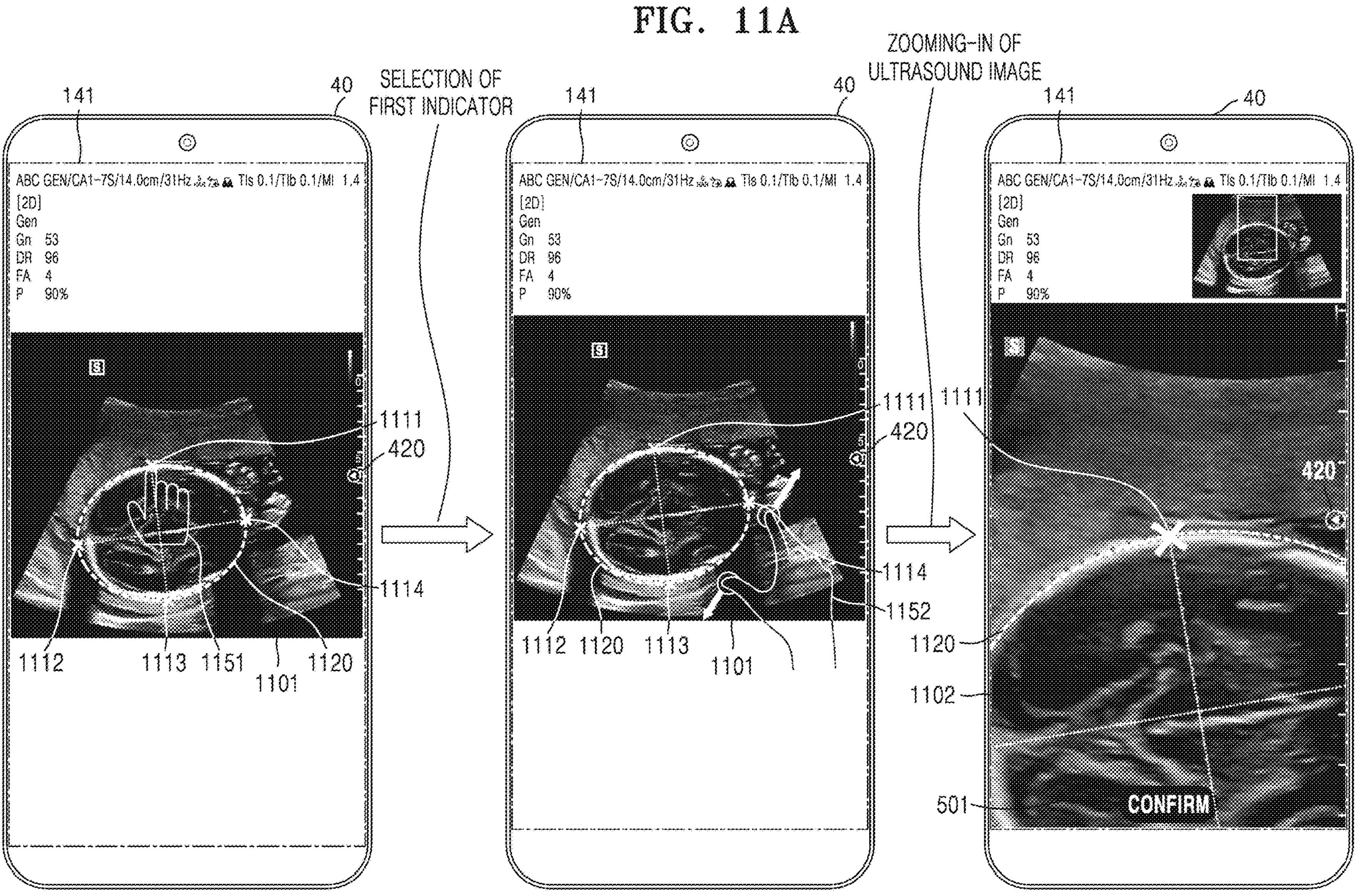
FIGS. 11A, 11B, and 11C are diagrams for describing that an ultrasound imaging device measures an area of an ultrasound image, according to an embodiment.
Figure 11B:
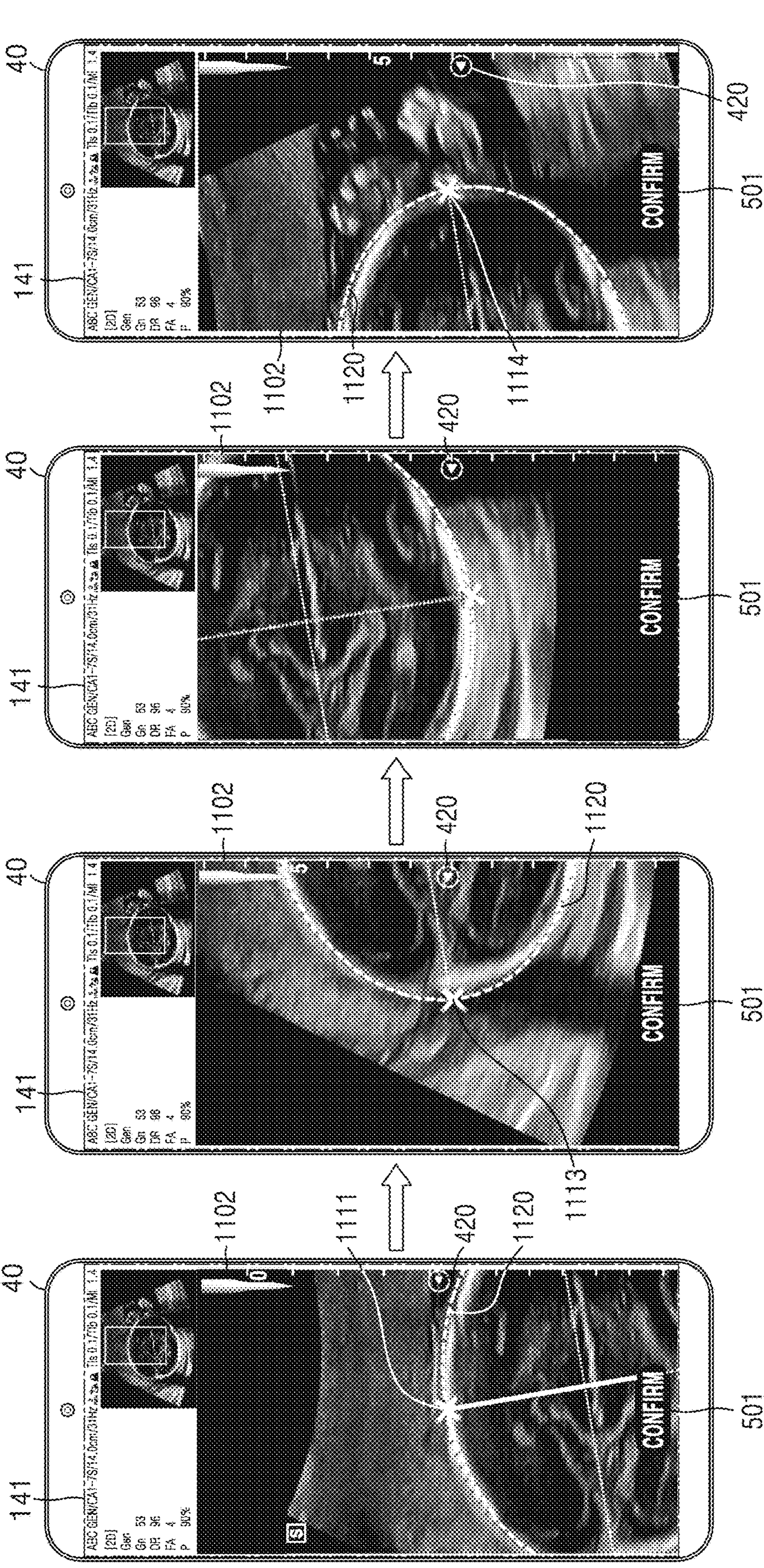
Figure 11C:
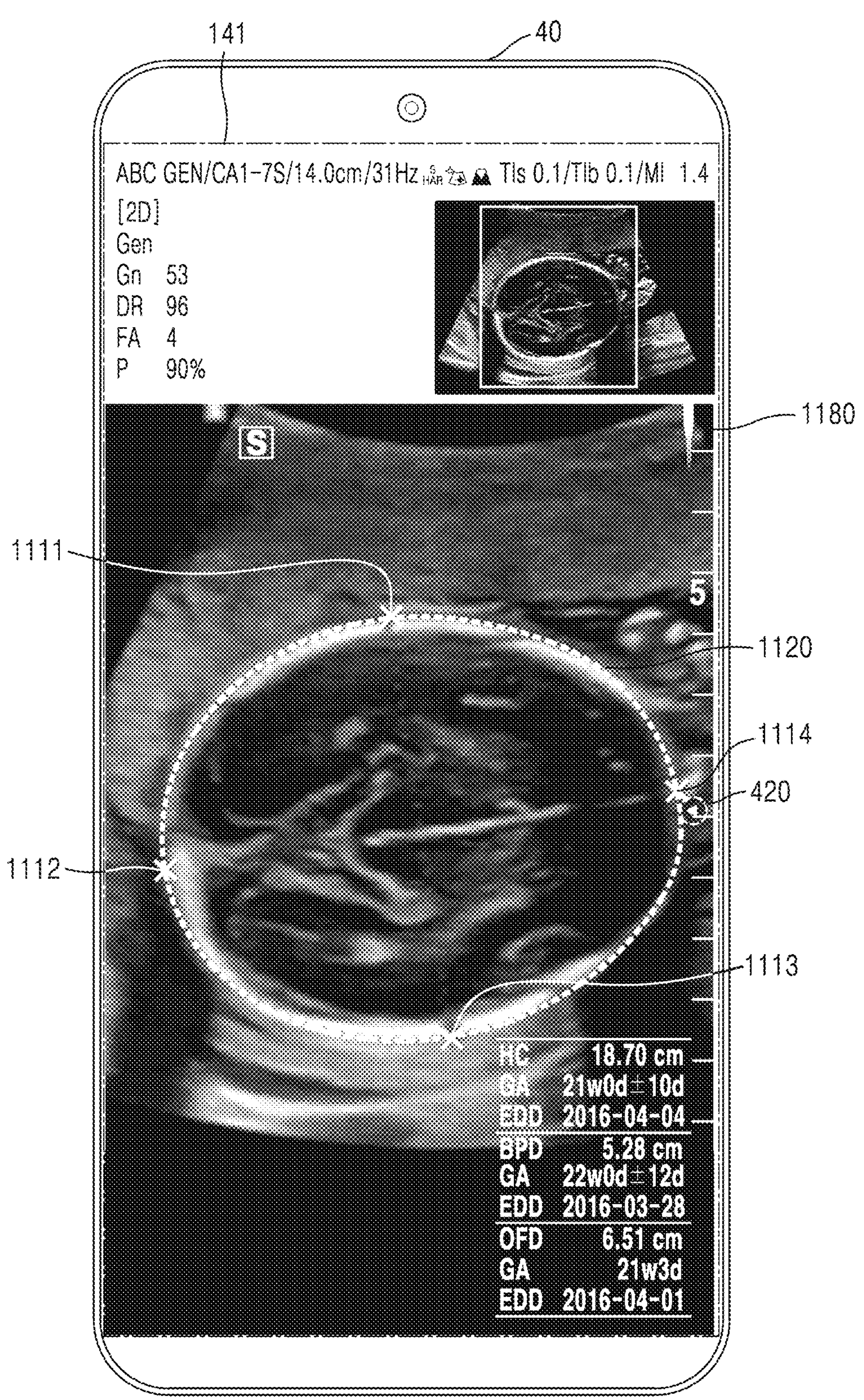

FIGS. 11A, 11B, and 11C are diagrams for describing that the ultrasound imaging device 40 measures an area of an ultrasound image, according to an embodiment. Descriptions of some operations among operations of the ultrasound imaging device 40 to be described via FIGS. 11A, 11B, and 11C may not be provided here as the descriptions are redundant to those provided with reference to FIGS. 10A, 10B, 10C, and 10D.

Referring to FIG. 11A, the ultrasound imaging device 40 may display, in a display area 1101 of the touch screen 141, an ultrasound image, and a first indicator 1111, a second indicator 1112, a third indicator 1113, and a fourth indicator 1114 which overlap on the ultrasound image. In an embodiment, the ultrasound imaging device 40 may display a line 1120 to overlap on the ultrasound image, the line 1120 connecting among the first indicator 1111, the second indicator 1112, the third indicator 1113, and the fourth indicator 1114.

In an embodiment, when the ultrasound imaging device 40 displays the ultrasound image in the display area 1101 and obtains a user input of selecting a measurement mode for measuring a width of an oval-shape area in the ultrasound image, the ultrasound imaging device 40 may display the first indicator 1111, the second indicator 1112, the third indicator 1113, and the fourth indicator 1114 to overlap on the ultrasound image. In an embodiment, in response to a user input 1151 of selecting the first indicator 1111 and a user input 1051 of zooming in the ultrasound image, the ultrasound imaging device 40 may display, in a display area 1102, a zoomed-in ultrasound image indicating a zoomed-in area around the first indicator 1111.

Referring to FIG. 11B, the ultrasound imaging device 40 may determine a position of the first indicator 1111 to be a first position at which the first indicator 1111 overlaps on the zoomed-in ultrasound image displayed in the display area 1102. Similarly, the ultrasound imaging device 40 may determine positions of the second indicator 1112, the third indicator 1113, and the fourth indicator 1114 to be a second position, a third position, and a fourth position. In an embodiment, the ultrasound imaging device 40 may move a position of a focal point to a position at which an indicator fixed in the display area 1102 overlaps on the zoomed-in ultrasound image, and may display, on the touch screen 141, the focal point indicator 420 to correspond to the moved position of the focal point.

Referring to FIG. 11C, the ultrasound imaging device 40 may obtain, as a result of preset measurement, area information of an object in the line 1120 connecting all of the first indicator 1111 placed at the first position, the second indicator 1112 placed at the second position, the third indicator 1113 placed at the third position, and the fourth indicator 1114 placed at the fourth position, and may display a text indicating the obtained result of preset measurement, on the touch screen 141. For example, the area information of the object may include at least one of a fetal biparietal diameter (BD), a fetal head circumference (HC), a fetal abdominal circumference (AC), a fetal femur length (AL), a fetal crown-rump length (CRL), a fetal nuchal translucency (NT) length, a fetal nasal bone (NB), a cervical length (CL), or an amniotic fluid (AF) space, but the disclosure is not limited to the example above.

In an embodiment, the ultrasound imaging device 40 may display, in a display area 1080, a result output ultrasound image indicating an area including all of the first indicator 1111 placed at the first position, the second indicator 1112 placed at the second position, the third indicator 1113 placed at the third position, and the fourth indicator 1114 placed at the fourth position. In an embodiment, the ultrasound imaging device 40 may obtain a user input of selecting at least one of a plurality of pieces of area information of a plurality of objects, and may display the selected area information of an object together the result output ultrasound image on the touch screen 141.

Figure 12A:
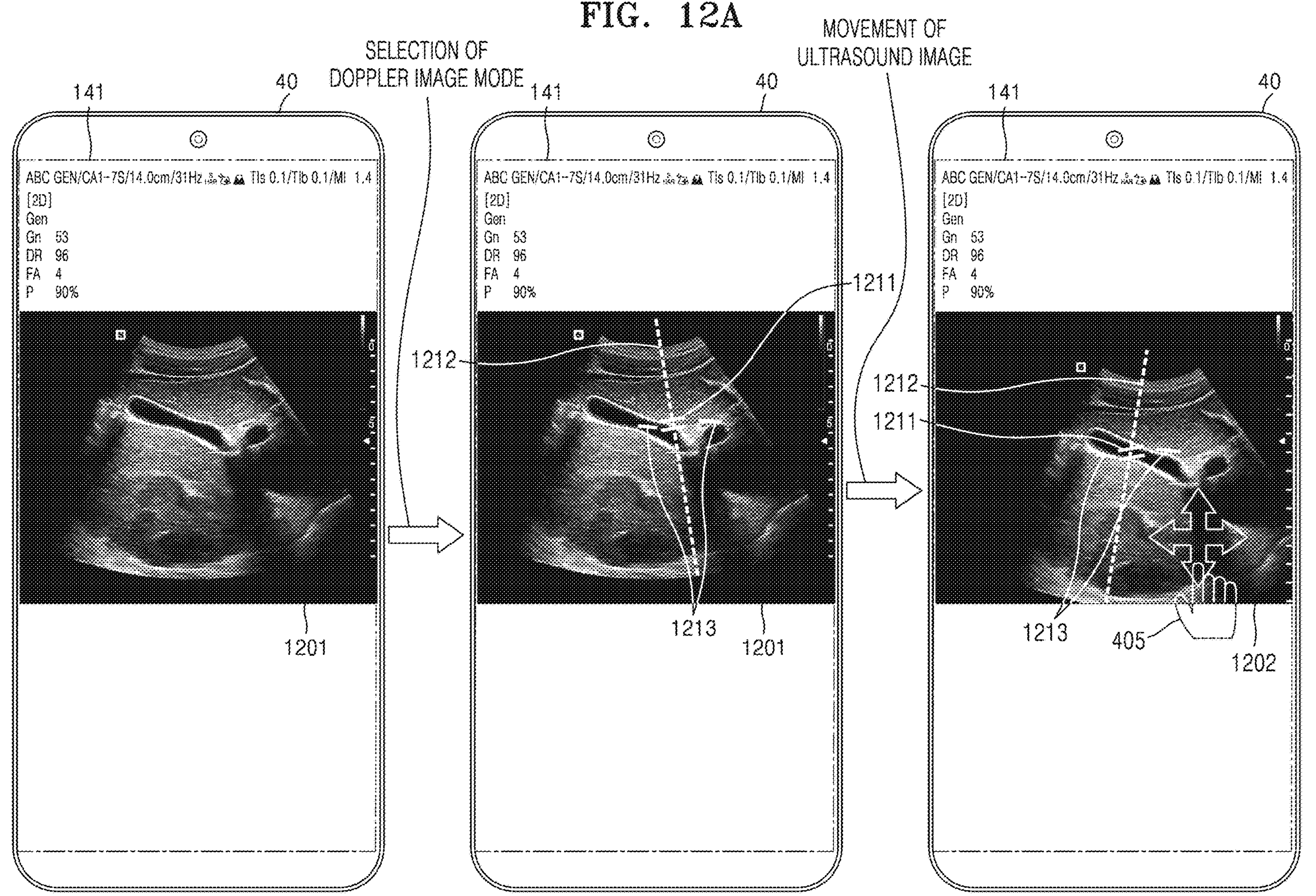
FIGS. 12A and 12B are diagrams for describing that an ultrasound imaging device according to an embodiment determines a position of a scan line and a position of a sample volume gate which are of a Doppler image.
Figure 12B:
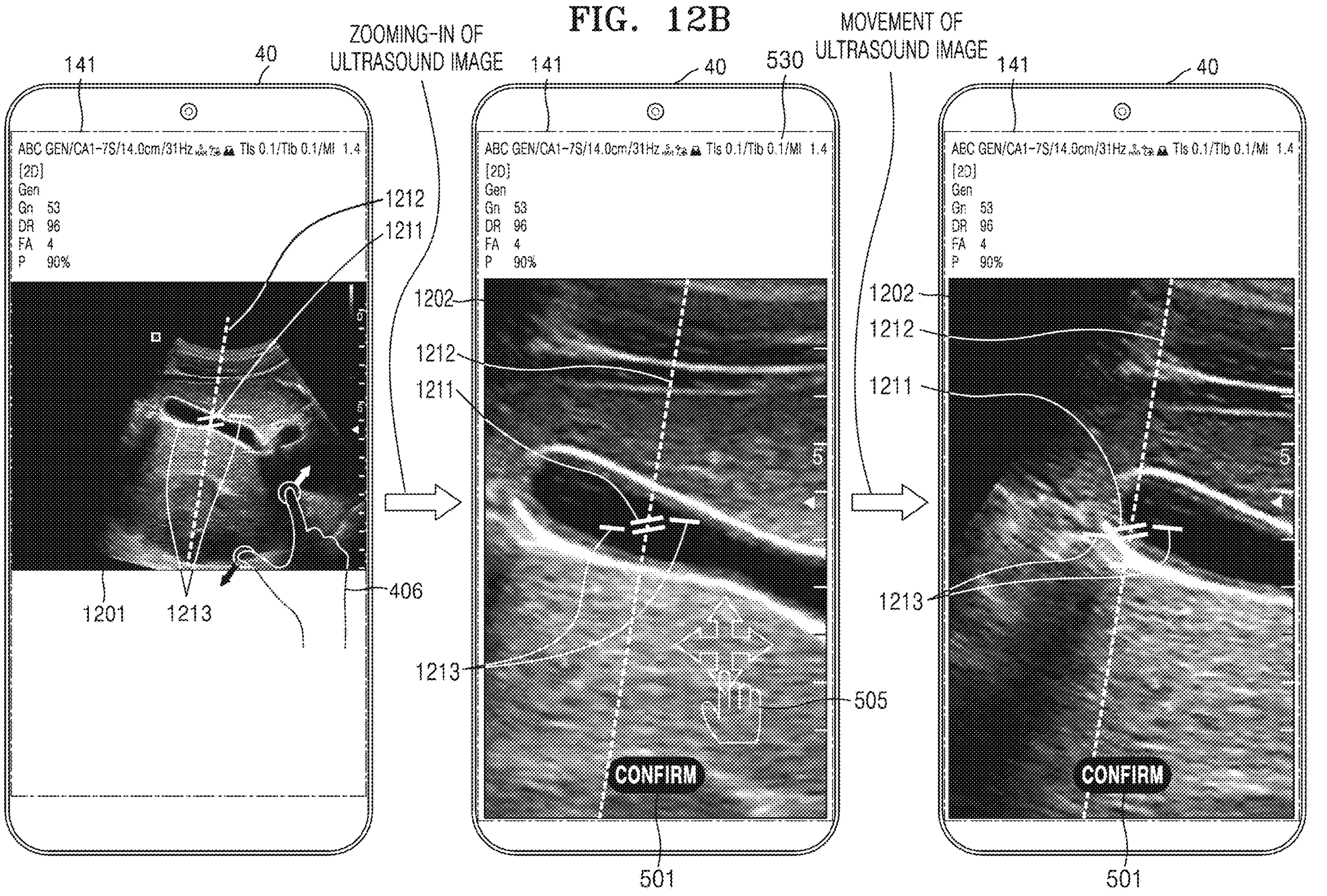

FIGS. 12A and 12B are diagrams for describing that the ultrasound imaging device 40 according to an embodiment determines a position of a scan line and a position of a sample volume gate which are of a Doppler image.

Referring to FIG. 12A, the ultrasound imaging device 40 may display an ultrasound image in a display area 1201 of the touch screen 141.

In an embodiment, the ultrasound imaging device 40 may display a first Doppler indicator 1211, a second Doppler indicator 1212, and a third Doppler indicator 1213 to overlap on a first ultrasound image, the first Doppler indicator 1211 being configured to determine a position of a sample volume gate of a Doppler image, the second Doppler indicator 1212 being configured to determine a position of a scan line of the Doppler image, and the third Doppler indicator 1213 being configured to determine an angle of the sample volume gate according to a stream line corresponding to a blood flow of an object in the Doppler image. The first Doppler indicator 1211, the second Doppler indicator 1212, and the third Doppler indicator 1213 may correspond to a first indicator described with reference to FIG. 3, and thus, redundant descriptions thereof are not provided here. While FIG. 12 shows that all of the first Doppler indicator 1211, the second Doppler indicator 1212, and the third Doppler indicator 1213 are displayed, some of them may not be displayed.

In an embodiment, when the ultrasound imaging device 40 displays an ultrasound image and obtains a user input of selecting a Doppler image measurement mode, the ultrasound imaging device 40 may display the first Doppler indicator 1211, the second Doppler indicator 1212, and the third Doppler indicator 1213 to overlap on the ultrasound image.

In an embodiment, the ultrasound imaging device 40 may determine a position of a sample volume gate of a Doppler image, based on a position of the first Doppler indicator 1211 placed on the ultrasound image. In an embodiment, the ultrasound imaging device 40 may determine a type of the sample volume gate, and may display the first Doppler indicator 1211 to overlap on the ultrasound image, the first Doppler indicator 1211 corresponding to the determined type of the sample volume gate. In an embodiment, a type of a sample volume gate may be determined based on a size and a shape of the sample volume gate, and the ultrasound imaging device 40 may determine a type of the sample volume gate, based on a user input of setting at least one of a size or a shape of the sample volume gate, or may determine a type of the sample volume gate, based on a user input of selecting one of preset types of the sample volume gate.

In an embodiment, the ultrasound imaging device 40 may determine a position of a scan line of the Doppler image, based on a position of the second Doppler indicator 1212 placed on the ultrasound image The second Doppler indicator 1212 may be positioned on a line that connects between a preset position on the ultrasound image and a position at which the first Doppler indicator 1211 overlaps on a first ultrasound image In an embodiment, the ultrasound imaging device 40 may determine an angle of the sample volume gate according to a stream line corresponding to a blood flow of an object, based on a position of the third Doppler indicator 1213 placed on the ultrasound image.

In an embodiment, the ultrasound imaging device 40 may move the ultrasound image, in response to a touch input 405 of moving the ultrasound image in the display area 1201, while the position of the first Doppler indicator 1211 and the position of the third Doppler indicator 1213 are fixed in the display area 1201. In an embodiment, as the ultrasound image is moved in the display area 1201, the ultrasound imaging device 40 may display the moved ultrasound image, and the first Doppler indicator 1211, the second Doppler indicator 1212, and the third Doppler indicator 1213 in the display area 1201.

In an embodiment, as the ultrasound image is moved, the ultrasound imaging device 40 may move a position at which the second Doppler indicator 1212 overlaps on the ultrasound image so as to allow the first Doppler indicator 1211 to be positioned on a line that connects between a preset position on the moved ultrasound image and a position at which the first Doppler indicator 1211 overlaps on the moved ultrasound image.

Referring to FIG. 12B, the ultrasound imaging device 40 may display a zoomed-in ultrasound image indicating a zoomed-in area around the first Doppler indicator 1211 overlapped on an ultrasound image, the first Doppler indicator 1211, the second Doppler indicator 1212, and the third Doppler indicator 1213 in a display area 1202, in response to a user input 406 of zooming in the ultrasound image. In an embodiment, the ultrasound imaging device 40 may display the first Doppler indicator 1211 and the third Doppler indicator 1213 at preset positions in the display area 1022.

In an embodiment, the ultrasound imaging device 40 may move the zoomed-in ultrasound image, in response to a first touch input 505 of moving the zoomed-in ultrasound image in the display area 1022, while positions of the first Doppler indicator 1211 and the third Doppler indicator 1213 are fixed in a display area 1201. In an embodiment, as the zoomed-in ultrasound image is moved, the ultrasound imaging device 40 may display, in the display area 1202, the moved zoomed-in ultrasound image, the first Doppler indicator 1211, the second Doppler indicator 1212, and the third Doppler indicator 1213.

In an embodiment, as the zoomed-in ultrasound image is moved, the ultrasound imaging device 40 may move a position at which the second Doppler indicator 1212 overlaps on the ultrasound image so as to allow the first Doppler indicator 1211 to be positioned on a line that connects between a preset position on the moved zoomed-in ultrasound image and a position at which the first Doppler indicator 1211 overlaps on the moved zoomed-in ultrasound image.

In an embodiment, when a user input of selecting a position determination UI 501 is input, the ultrasound imaging device 40 may determine respective positions at which the first Doppler indicator 1211, the second Doppler indicator 1212, and the third Doppler indicator 1213 overlap on the zoomed-in ultrasound image, to be a position of a sample volume gate of a Doppler image, a position of a scan line of the Doppler image, and an angle of the sample volume gate according to a stream line corresponding to a blood flow of an object in the Doppler image.

In an embodiment, the ultrasound imaging device 40 may obtain the Doppler image, based on the determined position of the sample volume gate, the determined position of the scan line of the Doppler image, and the determined angle of the sample volume gate according to the stream line corresponding to the blood flow of the object in the Doppler image, and may display the obtained Doppler image on the touch screen 141.

Figure 13:
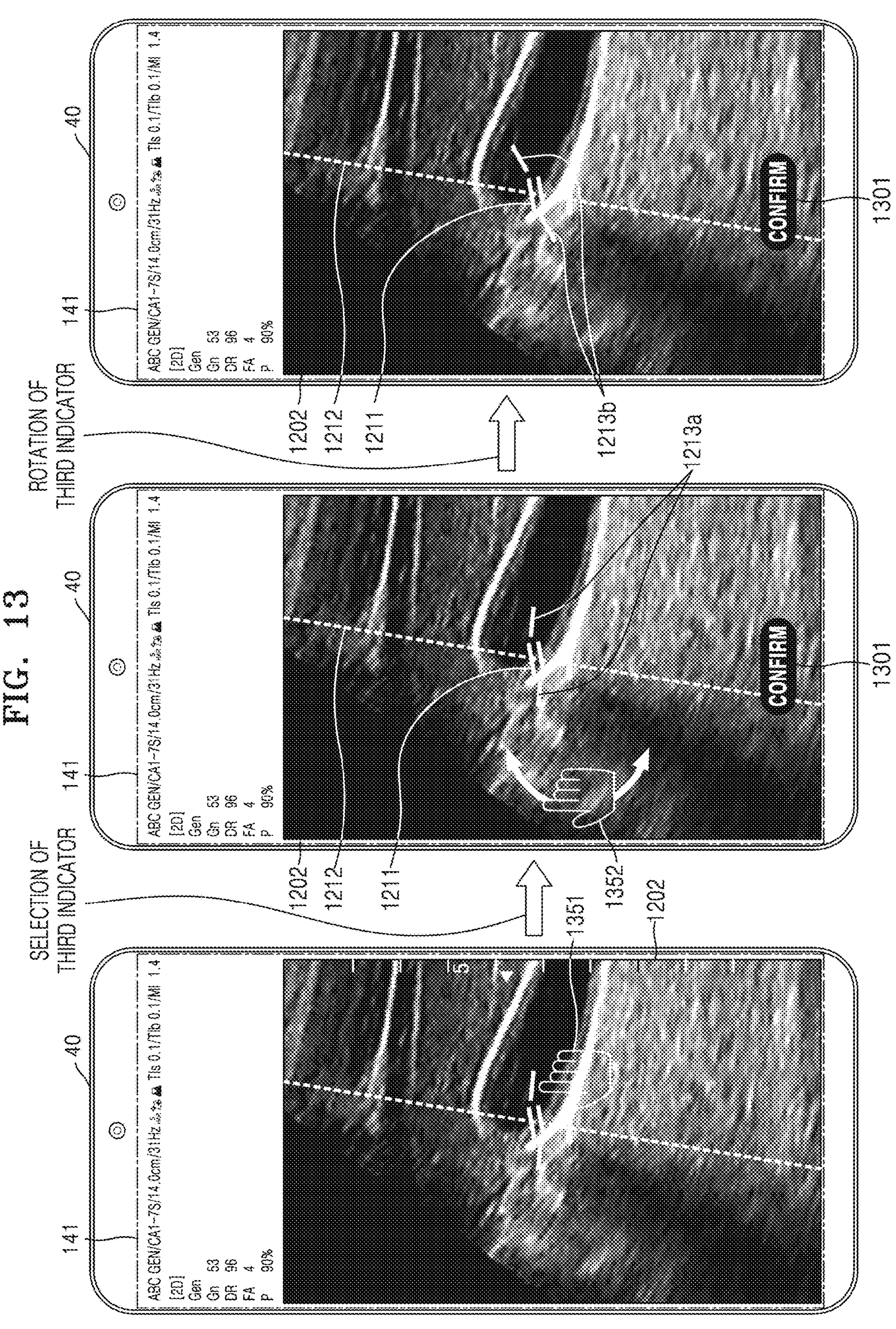
FIG. 13 is a diagram for describing that an ultrasound imaging device according to an embodiment adjusts an angle of a sample volume gate.

FIG. 13 is a diagram for describing that the ultrasound imaging device 40 according to an embodiment adjusts an angle of a sample volume gate.

Referring to FIG. 13, the ultrasound imaging device 40 may display a zoomed-in ultrasound image, the first Doppler indicator 1211, the second Doppler indicator 1212, and a third Doppler indicator 1213*a*, in a display area 1202 of the touch screen 141. Here, the third Doppler indicator 1213*a* may correspond to the third Doppler indicator 1213 of FIGS. 12A and 12B.

In an embodiment, the ultrasound imaging device 40 may obtain a user input for adjusting the third Doppler indicator 1213*a*. For example, a user input for adjusting an angle of a sample volume gate may include a touch input 1351 of selecting the third Doppler indicator 1213*a* overlapping on the zoomed-in ultrasound image. However, the disclosure is not limited thereto, and the ultrasound imaging device 40 may obtain, via the input interface 170, a user input for adjusting the third Doppler indicator 1213*a*.

In an embodiment, when a user input for adjusting the third Doppler indicator 1213*a* is obtained, the ultrasound imaging device 40 may obtain a touch input 1352 of changing an angle of a sample volume gate via the touch screen 141, until an angle of the third Doppler indicator 1213*a* is determined. In other words, from a time when the user input for adjusting the third Doppler indicator 1213*a* is obtained to a time when an angle of a sample volume gate is determined, the ultrasound imaging device 40 may obtain a touch input that is input via the touch screen 141, as the touch input 1352 of changing the angle of the sample volume gate, not as a touch input with respect to the zoomed-in ultrasound image.

In an embodiment, the ultrasound imaging device 40 may rotate the third Doppler indicator 1213*a* while the zoomed-in ultrasound image is fixed, in response to the touch input 1352 of changing the angle of the sample volume gate. In an embodiment, the ultrasound imaging device 40 may display, in the display area 1202, a third Doppler indicator 1213*b* whose angle is changed as the third Doppler indicator 1213*a* is rotated.

In an embodiment, when the ultrasound imaging device 40 displays an angle determination UI 1301 on the touch screen 141, and then obtains a user input of selecting the displayed angle determination UI 1301, the ultrasound imaging device 40 may determine the angle of the sample volume gate, based on a position at which the third Doppler indicator 1213*b* whose angle is changed overlaps on the zoomed-in ultrasound image.

Figure 14:
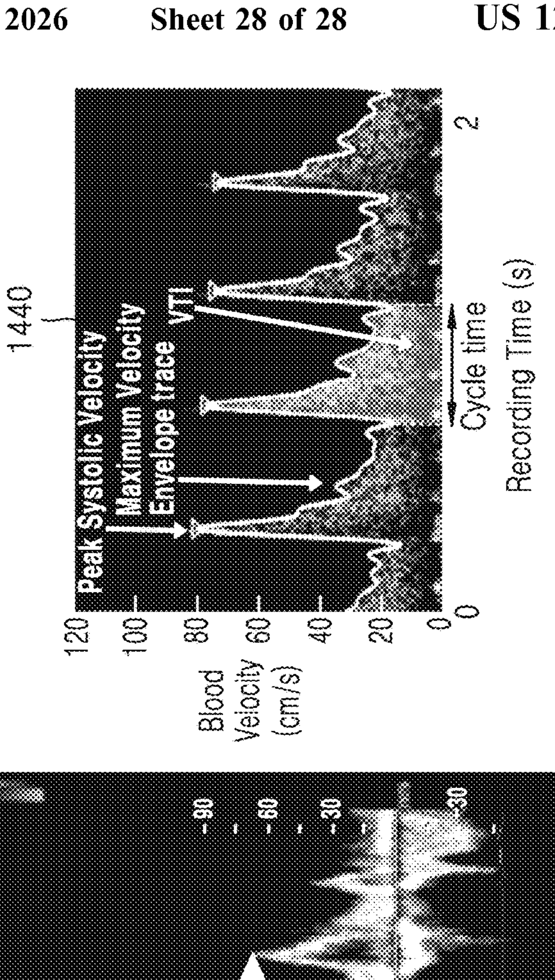
FIG. 14 is a diagram for describing a Doppler image, according to an embodiment.

FIG. 14 is a diagram for describing a Doppler image, according to an embodiment.

In an embodiment, the ultrasound imaging device 40 may obtain a Doppler image 1400, based on at least one of a position of a sample volume gate, a position of a scan line of the Doppler image, or an angle of the sample volume gate according to a stream line corresponding to a blood flow of an object in the Doppler image, and may display the obtained Doppler image 1400 on the touch screen 141.

In an embodiment, the Doppler image 1400 may include a color Doppler displayed to overlap on an ultrasound image 1410 with respect to an object 10. In an embodiment, the color Doppler may indicate a color map 1420 on which a direction and velocity of a blood flow of the object 10 positioned near the sample volume gate are visualized.

In an embodiment, the Doppler image 1400 may include a Doppler spectrum 1430.

The Doppler spectrum 1430 may indicate spectrum data including information about the velocity and direction of the blood flow of the object 10 positioned near the sample volume gate.

In an embodiment, the ultrasound imaging device 40 may obtain a touch input 1451 of dragging along the Doppler spectrum 1430. In an embodiment, when the touch input 1451 is obtained, the ultrasound imaging device 40 may extract an envelope on a time domain on which the touch input 1451 is performed on the Doppler spectrum 1430, and may display, on the touch screen 141, a blow-flow velocity graph 1440 including information about the extracted envelope.

Embodiments may be embodied as a computer-readable recording medium, e.g., a program module to be executed in computers, which includes computer-readable instructions. The computer-readable recording medium may include any usable medium that may be accessed by computers, volatile and non-volatile medium, and detachable and non-detachable medium. Also, the computer-readable recording medium may include a computer storage medium and a communication medium. The computer storage medium includes all volatile and non-volatile media, and detachable and non-detachable media which are technically implemented to store information including computer-readable instructions, data structures, program modules or other data. The communication medium includes computer-readable instructions, a data structure, a program module, or other data such as modulation-type data signals.

Also, the computer-readable recording medium may be provided in the form of a non-transitory recording medium. Here, the term "non-transitory storage medium" may mean that the storage medium is a tangible device and does not include signals (e.g., electromagnetic waves), and may mean that data may be permanently or temporarily stored in the storage medium. For example, the "non-transitory storage medium" may include a buffer in which data is temporarily stored.

It is obvious to one of ordinary skill in the art that the descriptions of the disclosure are exemplary and the disclosure may be easily embodied in many different forms without changing the technical concept or essential features of the disclosure. Thus, it should be understood that the embodiments described herein should be considered in a descriptive sense only and not for purposes of limitation. For example, configuring elements that are singular forms may be executed in a distributed fashion, and also, configuring elements that are distributed may be combined and then executed.

The scope of the disclosure is defined by the appended claims, rather than the detailed description, and all differences and modifications that can be derived from the meanings and scope of the claims and other equivalent embodiments therefrom will be construed as being included in the disclosure.

What is claimed is:

1. A control method of an ultrasound imaging device, the control method comprising:

displaying an ultrasound image in a display area of a touch screen;

displaying a first indicator to overlap on the ultrasound image;

determining a first movement degree and a first movement direction of the ultrasound image based on a first touch input on the touch screen to move the ultrasound image in the display area;

moving the ultrasound image corresponding to the first movement degree and the first movement direction while a position of the first indicator is fixed in the display area;

determining a position of the first indicator to be a first position, in response to a first position determination input of determining the position of the first indicator so as to place the first indicator at the first position on the ultrasound image;

determining a second movement degree and a second movement direction of the ultrasound image based on a second touch input on the touch screen to move the ultrasound image in the display area; and moving the ultrasound image corresponding to the second movement degree and the second movement direction while the first indicator is fixed at the first position and moves together with the ultrasound image.

2. The control method of claim 1, wherein the displaying of the first indicator to overlap on the ultrasound image comprises:

obtaining a user input of selecting a measurement mode; and displaying the first indicator to overlap on the ultrasound image, the first indicator corresponding to the selected measurement mode.

3. The control method of claim 1, further comprising displaying the ultrasound image indicating a zoomed-in area around the first indicator overlapped on the ultrasound image.

4. The control method of claim 1, further comprising displaying a second indicator to overlap on the ultrasound image; and wherein the moving of the ultrasound image in response to the second touch input comprises moving the ultrasound image, while a position of the second indicator is fixed in the display area, in response to the second touch input.

5. The control method of claim 4, further comprising determining the position of the second indicator to be a second position, in response to a second position determination input of determining the position of the second indicator so as to place the second indicator at the second position on the ultrasound image.

6. The control method of claim 4, further comprising, when the position of the first indicator is determined to be the first position, displaying the ultrasound image indicating a zoomed-in area around the second indicator overlapped on the ultrasound image.

7. The control method of claim 4, wherein the moving of the ultrasound image while the position of the second indicator is fixed in the display area comprises fixing the first indicator at the first position and moving the first indicator together with the ultrasound image.

8. The control method of claim 4, further comprising displaying a line to overlap on the ultrasound image, the line connecting between the first indicator and the second indicator.

9. The control method of claim 1, wherein the first indicator comprises an indicator configured to determine at least one of a position of a scan line of a Doppler image comprised in the ultrasound image or a position of a sample volume gate of the Doppler image.

10. The control method of claim 9, further comprising:

displaying a third indicator to overlap on the ultrasound image, the third indicator being configured to determine an angle of the sample volume gate according to a stream line corresponding to a blood flow of an object in the Doppler image; and rotating the third indicator, while the ultrasound image is fixed, in response to a third touch input of changing the angle of the sample volume gate.

11. A non-transitory computer-readable recording medium having recorded thereon a program for performing the control method of claim 1, on a computer.

12. An ultrasound imaging device comprising:

a touch screen;

a memory storing one or more instructions; and at least one processor configured to execute the one or more instructions stored in the memory, wherein the at least one processor is configured to execute the one or more instructions to display an ultrasound image in a display area of the touch screen, display a first indicator to overlap on the ultrasound image, determine a first movement degree and a first movement direction of the ultrasound image based on a first touch input on the touch screen to move the ultrasound image in the display area, move the ultrasound image corresponding to the first movement degree and the first movement direction while a position of the first indicator is fixed in the display area, determine a position of the first indicator to be a first position, in response to a first position determination input of determining the position of the first indicator so as to place the first indicator at the first position on the ultrasound image, determine a second movement degree and a second movement direction of the ultrasound image based on a second touch input on the touch screen to move the ultrasound image in the display area, move the ultrasound image corresponding to the second movement degree and the second movement direction while the first indicator is fixed at the first position and moves together with the ultrasound image.

13. The ultrasound imaging device of claim 12, wherein the at least one processor is configured to execute the one or more instructions to obtain a user input of selecting a measurement mode, and display the first indicator to overlap on the ultrasound image, the first indicator corresponding to the selected measurement mode.

14. The ultrasound imaging device of claim 12, wherein the at least one processor is configured to execute the one or more instructions to display the ultrasound image indicating a zoomed-in area around the first indicator overlapped on the ultrasound image.

15. The ultrasound imaging device of claim 12, wherein the at least one processor is configured to execute the one or more instructions to display a second indicator to overlap on the ultrasound image, and move the ultrasound image, while a position of the second indicator is fixed in the display area, in response to the second touch input.

16. The ultrasound imaging device of claim 15, wherein the at least one processor is configured to execute the one or more instructions to determine the position of the second indicator to be a second position, in response to a second position determination input of determining the position of the second indicator so as to place the second indicator at the second position on the ultrasound image.

17. The ultrasound imaging device of claim 15, wherein the at least one processor is configured to execute the one or more instructions to, when the position of the first indicator is determined to be the first position, display the ultrasound image indicating a zoomed-in area around the second indicator overlapped on the ultrasound image.

18. The ultrasound imaging device of claim 15, wherein the at least one processor is configured to execute the one or more instructions to fix the first indicator at the first position and move the first indicator together with the ultrasound image.

19. The ultrasound imaging device of claim 15, wherein the at least one processor is configured to execute the one or more instructions to display a line to overlap on the ultrasound image, the line connecting between the first indicator and the second indicator.

20. The ultrasound imaging device of claim 12, wherein the first indicator comprises an indicator configured to determine at least one of a position of a scan line of a Doppler image comprised in the ultrasound image or a position of a sample volume gate of the Doppler image.

* * * * *